United States Patent
Draghici et al.

(10) Patent No.: US 10,529,451 B2
(45) Date of Patent: Jan. 7, 2020

(54) PINS: A PERTURBATION CLUSTERING APPROACH FOR DATA INTEGRATION AND DISEASE SUBTYPING

(71) Applicant: Wayne State University, Detroit, MI (US)

(72) Inventors: Sorin Draghici, Detroit, MI (US); Tin Chi Nguyen, Detroit, MI (US)

(73) Assignee: WAYNE STATE UNIVERSITY, Detroit, MI (US)

( * ) Notice: Subject to any disclaimer, the term of this patent is extended or adjusted under 35 U.S.C. 154(b) by 745 days.

(21) Appl. No.: 15/068,048

(22) Filed: Mar. 11, 2016

(65) Prior Publication Data

US 2016/0267235 A1 Sep. 15, 2016

Related U.S. Application Data

(60) Provisional application No. 62/132,263, filed on Mar. 12, 2015, provisional application No. 62/221,727, filed on Sep. 22, 2015.

(51) Int. Cl.
*G16H 50/20* (2018.01)
*G06K 9/62* (2006.01)
*G16H 40/63* (2018.01)
*G06F 19/00* (2018.01)

(52) U.S. Cl.
CPC .............. *G16H 50/20* (2018.01); *G06F 19/00* (2013.01); *G06K 9/6223* (2013.01); *G16H 40/63* (2018.01)

(58) Field of Classification Search
None
See application file for complete search history.

(56) References Cited

PUBLICATIONS

Weber, "Robust perron cluster analysis for various applications in computational life science" in International Symposium on Computational Life Science, Springer, Berlin, Heidelberg, LNBI 3695, pp. 57-66, 2005.*
Chen, Gengxin, et al. "Evaluation and comparison of clustering algorithms in analyzing ES cell gene expression data." Statistica Sinica (2002): 241-262.
Monti, S., Tamayo, P., Mesirov, J., and Golub, T., "Consensus clustering: a resampling-based method for class discovery and visualization of gene expression microarray data," Machine learning, vol. 52, No. 1-2, pp. 91-118, 2003.
Wang, B., A. M. Mezlini, F. Demir, M. Fiume, Z. Tu, M. Brudno, B. Haibe-Kains, and A. Goldenberg, "Similarity network fusion for aggregating data types on a genomic scale," Nature Methods, vol. 11, No. 3, pp. 333-337, 2014.
Wilkerson, M. and Hayes, D., "ConsensusClusterPlus: a class discovery tool with confidence assessments and item tracking," Bioinformatics, vol. 26, No. 12, pp. 1572-1573, 2010.

* cited by examiner

*Primary Examiner* — G Steven Vanni
(74) *Attorney, Agent, or Firm* — Harness, Dickey & Pierce, P.L.C.

(57) ABSTRACT

Disease subtyping is accomplished by a computer-implemented algorithm that manipulates a first genetic dataset to construct a set of first connectivity matrices. To this set of matrices Gaussian noise is introduced to generate a perturbed dataset. The computer-implemented algorithm assesses which of the set of first connectivity matrices was least affected by introduction of noise and that matric is used to define the optimal clustering. Once the optimal clustering is determined, computer-implemented supervised classification is performed to determine, for a particular patient, with which disease subtype cluster that person's genetic data most closely aligns. Armed with this knowledge, the treatment regimen is specified with much higher likelihood of success.

1 Claim, 48 Drawing Sheets

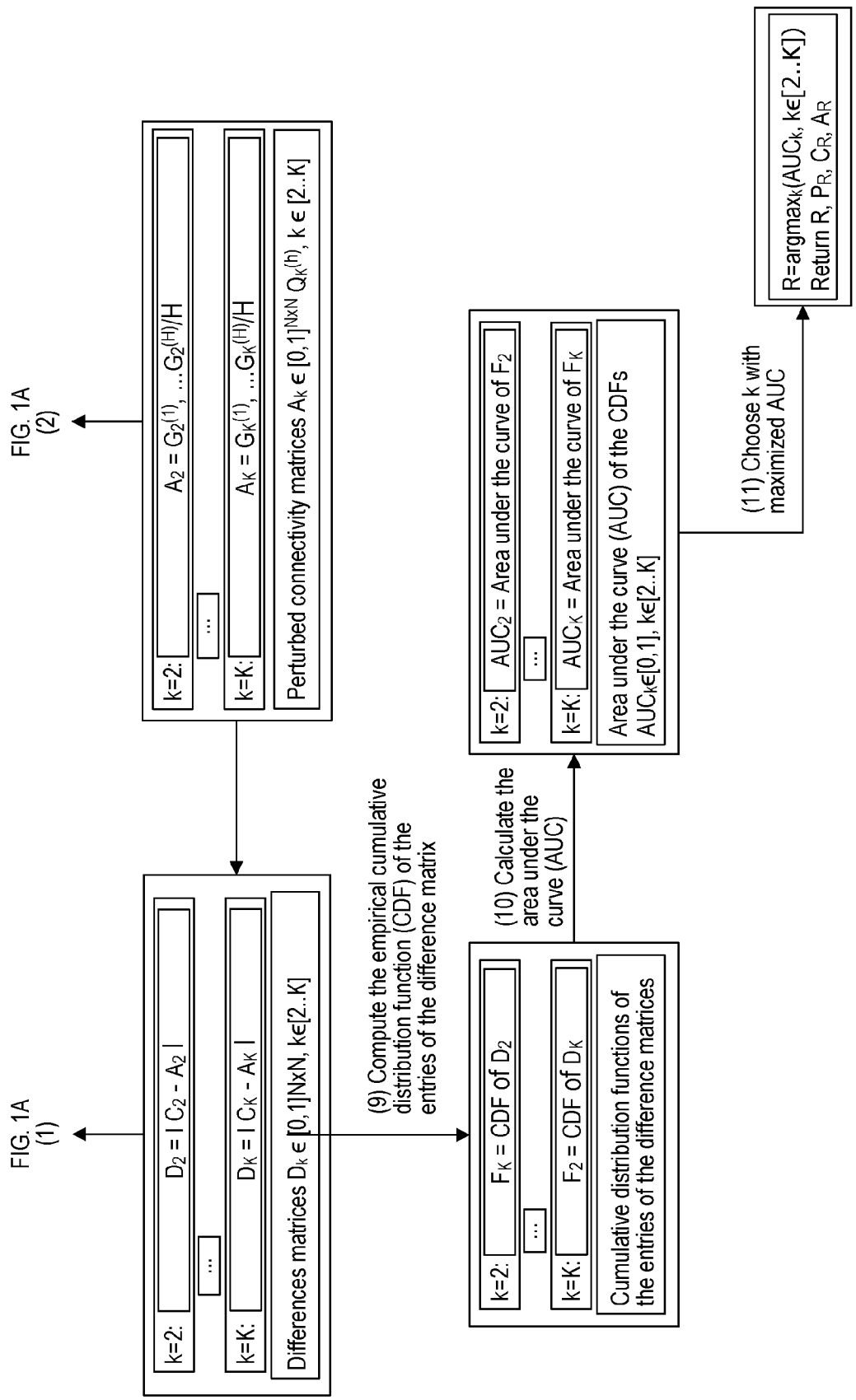

PINS: A PERTURBATION CLUSTERING APPROACH FOR DATA INTEGRATION AND DISEASE SUBTYPING

CROSS-REFERENCE TO RELATED APPLICATIONS

This application claims the benefit of U.S. Provisional Application No. 62/132,263 filed on Mar. 12, 2015 and U.S. Provisional Application No. 62/221,727 filed on Sep. 22, 2015. The entire disclosure of each of the above applications is incorporated herein by reference.

FIELD

The present disclosure relates to disease diagnosis using genetic analysis.

BACKGROUND

The advent of high-throughput genomics technologies has resulted in massive amounts of diverse genome-scale data. Gene expression data, measured by microarrays or next generation sequencing platforms, are the most prevalent data type available for biological data analysis. Gene Expression Omnibus stores thousands of datasets with independent experimental series of similar patient cohorts and experiment design. As technologies advance, other data types become available and together they offer complementary information on the same disease or biological phenomenon. The Cancer Genome Atlas (TCGA) has already gathered genome, transcriptome, and epigenome information for over 20 cancers for thousands of patients. The challenge is to interpret the massive amounts of high-dimensional and heterogeneous data types to gain insights into biological processes.

Disease subtyping is often the first step to better understand a disease or biological phenomenon. The goal is to detect unknown groups of patients based on intrinsic features without external information. The disease subtyping problem includes the following fundamental issues: 1) how to determine the number of clusters and assign patients to each group, 2) how to combine complementary information to determine the final partitioning. The former problem often involves clustering mRNA expression where the data has small sample size but very high dimension. This is still an important problem since gene expression is one of the most prevalent data type available. The latter problem includes integration of multi-omics data, such as mRNA expression, DNA methylation, and miRNA, for class discovery. With the rapidly advancing technologies, more and more data types are available for the same set of patients, making the increasing need for combining multi-omics data.

In functional genomics, agglomerative hierarchical clustering (HC) is a frequently used approach for clustering genes or samples that show similar expression patterns. HC provides for a structural view of the data that makes it appealing in exploratory data analysis. However, classical HC imposes a tree structure on the data that might not reflect the underlying structure, and is highly sensitive to the metric used to assess similarity among elements. Divisive clustering methods, such as k-means, global k-means, fuzzy modification of k-means, have been applied for the same application. These methods provide clear cluster boundaries and tighter clusters, but they lack the visual appeal of HC. Another group of methods are neural network clustering, such as self-organizing maps (SOM), Self-Organizing Tree Algorithm (SOTA), and Dynamically Growing Self-Organizing Tree (DGSOT). Neural networks can be modeled as a collection of nodes with weighted interconnections, which can be adaptively learned. The common drawbacks of both k-means based methods and neural networks based methods is the need to specify the number of clusters beforehand.

Resampling-based methods have been proposed to determine the number of clusters. They assess the stability of the clustering results with respect to resampling variability. Arguably the state-of-the-art approach in this area is Consensus Clustering (CC). It develops a general, model independent resampling-based methodology of class discovery, cluster validation, and visualization. CC calculates the pair-wise similarities (frequency of how often the elements are grouped together) and their empirical cumulative distribution function (CDF) using sub-sampling. The pair-wise similarities are then used for visualization and for estimating the cluster number. This approach has been widely used and gained laudable results. The main assumption of CC is that if the samples were drawn from K distinct sub-populations that truly exist, different sub-samples would show the greatest level of stability at the true K. Unfortunately, this makes CC claim apparent structure when there is none, or declare cluster stability when the stability is subtle.

The goal of an integrative analysis is to identify subgroups of samples that are similar not only at one level (e.g., mRNA), but from a holistic perspective, that can take into consideration phenomena at various other levels (e.g., DNA methylation, miRNA, etc.). One strategy is to analyze each data type independently before combining them. One of the drawbacks of this approach is that it might lead to inconsistent conclusions that are hard to integrate. Another approach is to use machine learning techniques. However, these methods are not scalable to the full spectrum of measurements, making them sensitive to gene selection step. One recent approach, Similarity Network Fusion (SNF), creates a network of patients for each data type before fusing the network using a metric fusion technique developed for image processing applications. The fused network is then partitioned using spectral clustering. The unstable nature of the spectral clustering and the metric fusion technique makes the method sensitive to its parameters. In addition, this method is not designed to solve the clustering when only one data type is available.

SUMMARY

Here we present a new approach to address both of the mentioned issues. Our framework is divided into two stages. In the first stage, we solve the classical clustering problem given a single data type. Although several specific high-dimensionality data types are illustrated in our examples here, our technology is general enough to be applicable for any high-dimensional genetic or life science data. The second stage combines the partitionings of individual data types to determine the final partitioning. In our experimental study, we evaluate the first stage by clustering 8 gene expression datasets of different diseases. For all the 8 datasets, PINS outperforms its competitors in recovering the true classes. To evaluate the second stage, we downloaded mRNA, DNA methylation, and miRNA data of 6 difference cancers from TCGA: kidney renal clear cell carcinoma (KIRC), glioblastoma (GBM), lung squamous cell carcinoma (LUSC), breast invasive carcinoma (BRCA), acute myeloid leukemia (LAML), and colon adeno-carcinoma (COAD) with survival and clinical data. PINS substantially outperforms other methods in identifying subtypes and in predicting survival using the multi-omics data.

BRIEF DESCRIPTION OF THE DRAWINGS

FIG. 2A—also referred to as FIG. 2, Panel (A)—is a graphical plot of the gene expression profile of the exemplary dataset;

FIG. 2B—also referred to as FIG. 2, Panel (B)—is a series of connectivity matrices, comparing original data vs perturbed data for different values of k;

FIG. 2C—also referred to as FIG. 2, Panel (C)—is a graph of the empirical cumulative distribution functions (CDF) of the difference matrix $D_k$;

FIG. 2D—also referred to as FIG. 2, Panel (D)—is a graph of the area under the curve (AUC) of the CDFs for each value of k;

FIG. 8A—also referred to as FIG. 8, Panel (A)—is a set of connectivity matrices, comparing original data vs perturbed data for k=3 and k=6;

FIG. 8B—also referred to as FIG. 8, Panel (B)—depicts the cumulative distribution functions (CDF) for different values of k;

FIG. 8C—also referred to as FIG. 8, Panel (C)—depicts the area under the curve (AUC) graph for dataset GSE19188 and dataset Gaussian1;

FIG. 8D—also referred to as FIG. 8, Panel (D)—depicts the clustering result in the first two principal components, where the circles represent the LCC samples; the triangles represent the ADC samples; the crosses represent the SCC samples;

DESCRIPTION OF PREFERRED EMBODIMENTS

Figure 1A:
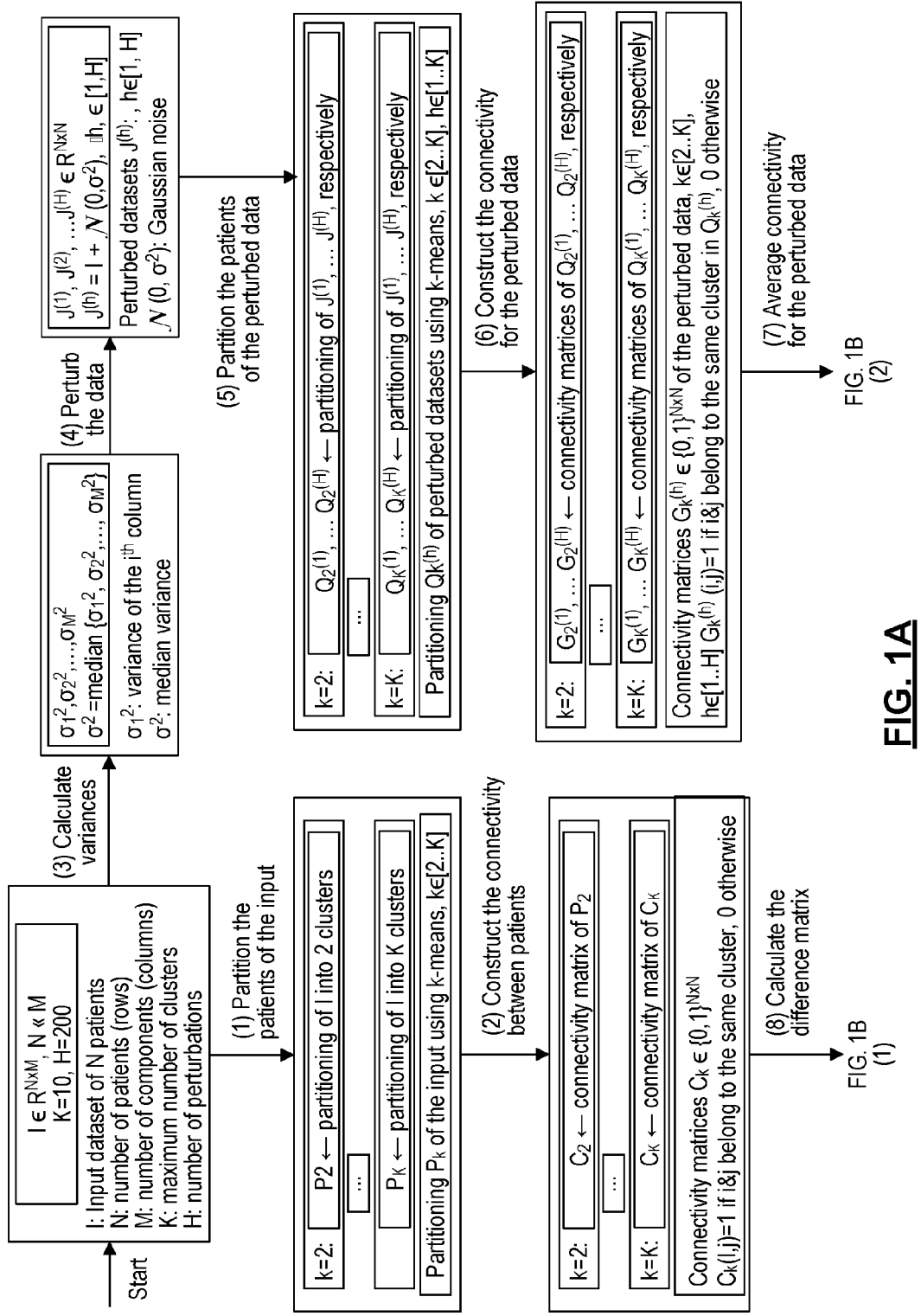
FIG. 1 is a flowchart diagram depicting the Stage I process for perturbation clustering for high dimensional data.

In this disclosure, we present a new technological approach to address both of the mentioned issues. We refer to our new technological approach by the acronym PINS (Perturbation clustering approach for data INtegration and disease Subtyping). Our technology is divided into two stages. In the first stage, we solve in a new way the classical clustering problem given a single data type. While particularly well suited to analyzing genetic data, our approach is general enough to be applicable for any high-dimensional data. The second stage combines the partitionings of individual data types to determine the final partitioning.

In our experimental study described here, we evaluate the first stage by clustering 8 gene expression datasets of different diseases. For all the 8 datasets, PINS outperforms its competitors in recovering the true classes. To evaluate the second stage, we downloaded mRNA, DNA methylation, and miRNA data of 6 difference cancers from TCGA: kidney renal clear cell carcinoma (KIRC), glioblastoma (GBM), lung squamous cell carcinoma (LUSC), breast invasive carcinoma (BRCA), acute myeloid leukemia (LAML), and colon adenocarcinoma (COAD) with survival and clinical data. PINS substantially outperforms other methods in identifying subtypes and in predicting survival using the multi-omics data.

II. METHODS

Here we describe the perturbation clustering for a single data type and data integration for multiple data type. This section is organized as follows. Section II-A describes the perturbation clustering (stage I), in which the patients are partitioned using one data type. This first stage outputs the clustering and the pair-wise connectivity of the patients. Section II-B describes the data integration and disease subtyping (stage II) using multi-omics data. This second stage consists of 2 phases. In phase 1, the pair-wise connectivity (between patients) for multiple data types are combined to form the network between patients. This network is then partitioned to determine the grouping using the integrated data. In phase 2, we further split each group into sub-groups if possible. The output of the phase 2 is then reported as the output of PINS using the multi-omics data.

A. Perturbation Clustering (Stage I)

In stage I of PINS, we solve the classical clustering problem, i.e., we focus on clustering samples (patients) using one data type. The approach is based on the observation that small changes in any kind of quantitative assay will be inherently present between individuals, even in a truly homogeneous population in the absence of any subtypes. Here, the hypothesis is that if well-defined subtypes of disease do exist, these have to be stable with respect to small changes in the measured values. Hence, we are not interested in any clusters that form or disappear due to small changes in the data, but rather we are looking for those groupings that remain stable across many clusterings built in the presence of small changes. In order to find such clusters, we add Gaussian noise to the data and reconstruct the clustering many times. The stability is assessed by the discrepancies in the clustering results between the original and the perturbed data. Based on this, we extract the "true" number of clusters as being the one that is least affected by such perturbations. In the absence of any true subtypes, the repeated clusterings will show lack of stability thus allowing us to avoid the discovery of false subtypes.

The framework will be described here using k-means clustering as the basic building block of our subtype discovery approach, but a number of other classical clustering approaches could be used instead. It is well-known that the k-means algorithm may converge to a local minimum depending on the initialization. To overcome this problem, we use the "modified version" of k-means, i.e., we run k-means many times with different random initialization and then choose the result that gives the least residual sum of squares (RSS). In the rest of this manuscript, the term k-means refers to the "modified version" of k-means.

The high-level algorithm can be briefly described as follows: i) For a given number of clusters k, we cluster the original data using k-means and then construct the connectivity between patients (original connectivity). ii) We add noise to the data and re-cluster the perturbed data many times to determine the average connectivity between patients when the data are perturbed (perturbed connectivity). iii) We calculate the discrepancy between the original clustering and the perturbed clustering for each k. iv) We repeat the above steps for all values of k in a range of interest (e.g., 2 . . . 10). v) We choose the k which gives the least discrepancy between the original and perturbed connectivity. The corresponding clustering is then returned as the most stable one.

Our approach differs from the existing methods in the following aspects: i) we accept the noisy nature of the biological measurement and use the data as they are (without data pre-processing) and therefore do not suffer from information loss and do not require a preliminary feature selection, nor a dimensionality reduction; ii) our stability metric is expected to deterministically and reliably identify the number of clusters present in the data.

FIG. 1 shows the detailed workflow of the perturbation clustering algorithm (stage I). The input of the algorithm is a dataset (matrix) $I \in R^{N \times M}$, where N is the number of patients and M is the number of measurements for each patient. In the example of gene expression, N is the number of samples and M is the number of genes (or probes) measured in each sample. In short, the rows of the matrix I represents the patients and the columns represents the components (features). The algorithm parameters are K (default 10) and H (default 200) where K is the maximum number of clusters and H is the number of perturbation H. The algorithm consists of 11 steps, which will be described step-by-step in the following sections.

1. Construction of Original Connectivity Matrices (Steps 1-2)

In step (1), we partition the patients using all possible number of clusters k=[2 . . . K]. Formally, the input I can be presented as a set of N patients I={$e_1, e_2, \ldots, e_N$} where each element $e_i$ is in a $M^{th}$ dimensional space and represents the molecular profile of the $i^{th}$ patient (i∈[1 . . . N]). A partitioning $P_k$ (k clusters) of I can be written in the form $P_k$={$P_1, P_2, \ldots, P_k$} where $P_i$ is a set of patients, such that $\cup_{i=1}^{k} P_i = I$ and $P_i \cap P_j = \emptyset$, ∀i, j∈[1, . . . k], i≠j. After step (1), we have (K−1) partitionings: {$P_2, \ldots, P_K$}, one for each value of k∈[2 . . . K].

In step (2), we build the pair-wise connectivity between the patients using the partitionings obtained from step (1). For a partitioning $P_k$, two patients are connected if they are clustered together. We build the connectivity matrix $C_k \in \{0, 1\}^{N \times N}$ from the partitioning $P_k$={$P_1, P_2, P_k$} as follows:

$$C_k(i,j) = \begin{cases} 1 & \text{if } \exists t \in [1..k]: i, j \in P_t \\ 0 & \text{otherwise} \end{cases} \quad (1)$$

In other words, the connectivity between two patients is 1 if and only if they belong to the same cluster. Let us consider one example. We cluster a set of 5 elements into 2 clusters with the resulted partitioning $P_2$={{1, 2},{3, 4, 5}}. In this case, element 1 is connected to element 2 and is not connected to other elements {3, 4, and 5}. Similarly, elements {3, 4, 5} are all connected to each other, but not to elements {1, 2}. Using equation (1), we construct the connectivity matrix for $P_2$ is as follows:

$$C_2 = \begin{bmatrix} 1 & 1 & 0 & 0 & 0 \\ 1 & 1 & 0 & 0 & 0 \\ 0 & 0 & 1 & 1 & 1 \\ 0 & 0 & 1 & 1 & 1 \\ 0 & 0 & 1 & 1 & 1 \end{bmatrix}$$

Intuitively, a partitioning can be presented as a graph in which each patient is a node and the connectivity between two patients is an edge, such that the edge exists if and only if the two patients have similar gene expression profile and thus are clustered together. Any two patients of a cluster are connected by an edge, and any two patients of different clusters are not connected. The connectivity matrix of is exactly the adjacency matrix of the graph.

We construct one connectivity matrix for each value of k∈[2 . . . K]. After step (2), we have (K−1) connectivity matrices $C_2, \ldots, C_K$. We refer to these matrices as original connectivity matrices because they are constructed from the original data without perturbation or resampling.

2. Generating Perturbed Datasets (steps 3-4)

In order to assess the stability of the partitionings obtained in steps (1-2), we generate H new datasets by adding Gaussian noise to the original data I. In step (3), we calculate the noise variance from the input. We first calculate the variances of the M components (columns). For example, for gene expression assay of 20,000 genes, we will get 20,000 variances, each variance for a gene represents the variability of that gene among the individuals. We then choose the median of the M variances to be the noise variance. Our reasoning is that the majority of the genes should have similar expression across individuals. The difference between individuals for those genes is due to technical variability and individual heterogeneity. By choosing the median variance, we hope that our noise setting is automatically adjusted to the noise of the system. Formally, the noise variance is calculated as follows:

$$\begin{cases} \forall j \in [1..M]: \sigma_j^2 = \text{var}\{I(i,j), i \in [1..N]\} \\ \sigma^2 = \text{median}\{\sigma_1^2, \ldots, \sigma_M^2\} \end{cases} \quad (2)$$

In step (4), we generate new datasets $J^{(h)} \in R^{N \times M}$ (h∈ [1 . . . H]) by adding Gaussian noise to the original data as follows:

$$J^{(h)} = I + N(0, \sigma^2) \quad (3)$$

where $\sigma^2$ is calculated in equation (2). After this step, we have Hperturbed datasets $J^{(1)}, J^{(2)}, \ldots, J^{(H)}$. We refer to these datasets as perturbed datasets because they are generated by perturbing the original data. The perturbed datasets will be used to compute the perturbed connectivity matrices in the following section.

3. Construction of Perturbed Connectivity Matrices (Steps 5-7)

In step (5), we cluster each of the H perturbed datasets using k-means with varying values of k∈[2 . . . A]. For example, for k=2, we partition the dataset $J^{(1)}$ into 2 clusters and get the $Q_2^{(1)}$ partitioning. We perform k-means with k=2 for all the H perturbed datasets and get H different partitionings $Q_2^{(1)}, Q_2^{(2)}, \ldots, Q_2^{(H)}$ for k=2. Please note that all these perturbed datasets were generated by adding small noise to the same input I. In the ideal case, $Q_2^{(1)}, Q_2^{(2)}, \ldots, Q_2^{(H)}$ are all identical to $P_2$. The more difference between them, the less reliable the $P_2$ partitioning.

After step (5), we have H different partitionings $Q_k^{(1)}, Q_k^{(2)}, \ldots, Q_k^{(H)}$ for each value of k∈[2 . . . K]. In step (6), we construct a connectivity matrix for each partitioning created in step (5). Specifically, for the partitioning $Q_k^{(h)}$ (h∈[1 . . . H], k∈[2 . . . K]), we construct the connectivity matrix $G_k^{(h)} \in \{0,1\}^{N \times N}$ as follows:

$$G_k^{(h)}(i,j) = \begin{cases} 1 & \text{if } i,j \text{ belong to the same cluster} \\ 0 & \text{otherwise} \end{cases} \quad (4)$$

After this step, we have H connectivity matrices $G_k^{(1)}, G_k^{(2)}, \ldots, G_k^{(H)}$ for a value of k. In the context of graph, each connectivity matrix can be considered as the presentation of the network between patients. For a given value of k, $C_k$ represents the network for the original data while $G_k^{(h)}$ represents the network between patients each time we perturb the data. The stability of the clustering is assessed based on the discrepancy between these altered networks and the original network. We first combine the altered networks before comparing the combined network to the original network. In step (7), we calculate the perturbed connectivity matrix by averaging the connectivity from $G_k^{(1)}, G_k^{(2)}, \ldots, G_k^{(H)}$ as follows:

$$A_k = \frac{1}{H} \sum_{h=1}^{H} G_k^{(h)} \quad (5)$$

where $A_k \in [0,1]^{N \times N}$, k∈[2 . . . K]. We refer to these matrices as perturbed connectivity matrices. For each value of k∈[2 . . . K], we have one original connectivity matrix and one perturbed connectivity matrix. The discrepancy between the two matrix reflects the stability of the partitioning $P_k$.

4) Stability Assessment (Step 8-10)

Given the number of cluster k, we would like to quantify the discrepancy between the $C_k$ and $A_k$. We calculate the difference matrix $D_k \in [0,1]^{N \times N}$ as follows:

$$D_k = |C_k - A_k| \quad (6)$$

$D_k(i,j)$ represents the change in connectivity between i and j when the data are perturbed. $D_k$ consists of numbers falling into the interval [0,1]. The distribution of the entries of $D_k$ reflects the stability of the clustering. The more this distribution shifts towards 1, the less robust the clustering. To quantify the discrepancy, we compute the empirical cumulative distribution function (CDF) of the for the entries of $D_k$. In step (9) we compute the function $F_k$ as follows:

$$F_k(c) = \frac{|\{D_k(i,j) \le c \wedge i, j \in [1..N]\}|}{N^2} \quad (7)$$

where the numerator represents the number of elements in $D_k$ that are smaller than or equal to c while the denominator represents the total number of elements in the matrix $D_k$.

In step (10), we calculate the area under the curve $AUC_k$ of the CDFs. When $C_k$ and $A_k$ are identical (i.e., data perturbation do not change the clustering result), the difference matrix $D_k$ consists of only 0's. In this case, $F_k(0)=1$, and thus the area under the curve $AUC_k$ to be maximized, i.e., $AUC_k=1$. If $C_k$ and $A_k$ differ from each other, then the entries of $D_k$ shift towards 1, making $AUC_k$ smaller than 1. The more different between $C_k$ and $A_k$, the smaller the $AUC_k$. The smaller the $AUC_k$, the more stable the partitioning. Therefore, we choose the optimal k for which the area under the curve (AUC) is maximized.

$$\hat{k} = \underset{k}{\operatorname{argmax}}(AUC_k, k \in [2..K]) \quad (8)$$

At the end of stage I, we return the optimal value of $\hat{k}$, the partitioning $P_{\hat{k}}$, the original connectivity matrix $C_{\hat{k}}$, and the perturbed connectivity matrix $A_{\hat{k}}$. The connectivity matrices $C_{\hat{k}}$, $A_{\hat{k}}$ represent the network between patients for one data type. These matrices will be used to combine multi-omics data for the final clustering in stage II of PINS.

To illustrate the workflow of the algorithm, we simulate 10 simulated datasets named Gaussian1, Gaussian2, . . . , Gaussian10. The number in each name is the number of classes of the dataset. Each dataset has 100 samples and 1,000 genes. The samples are equally divided among the classes. For example Gaussian2 has 2 classes of size 50 and Gaussian3 has 3 classes of size 33 and 34. We will show that the AUC values are notably low for Gaussian1 dataset, which suggests that any partitioning of this dataset is very unstable against data perturbation (FIG. 2). For the other 9 datasets, we will show that the partitioning is stable when the number of cluster equals the true number of classes (FIGS. 3, 4, 5, 6, 7).

FIG. 2 shows the workflow of PINS for the simulated dataset Gaussian1. The dataset consists of 100 samples and 1,000 genes. The expression values of each gene follow the Gaussian distribution N(0,1) as shown in panel (A). From the data, we calculate the variance of each gene. We have $\sigma_i^2 \approx 1, \forall i \in [1 \ldots 1000]$, and therefore $\sigma^2 \approx 1$. We note that the variance of the distribution has no impact on the result of PINS because the noise variance is set to be the median variance of the genes.

Figure 2A:
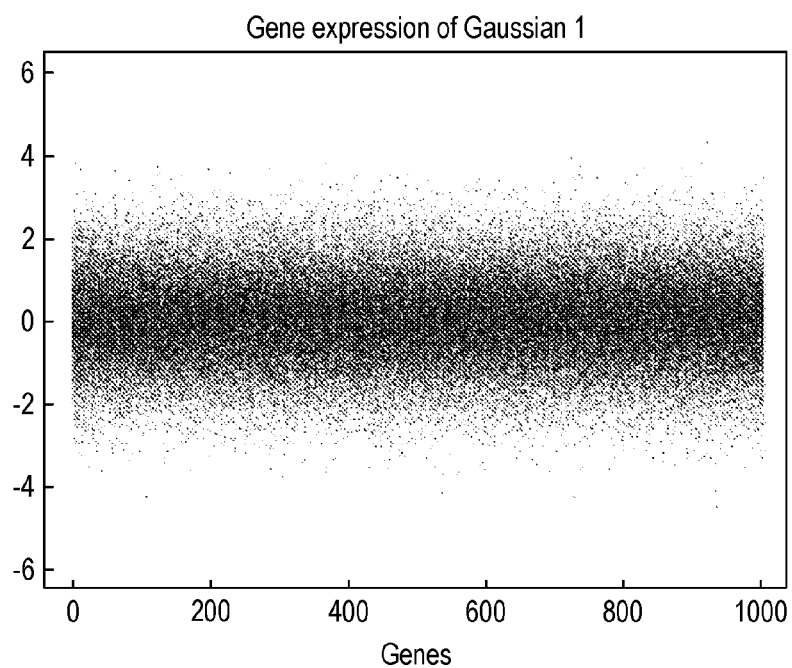
FIGS. 2A-2D (collectively referred to as FIG. 2) depicts a first exemplary dataset (Gaussian1-1 class) associated with the perturbation clustering process of FIG. 1, specifically.
Figure 2B:
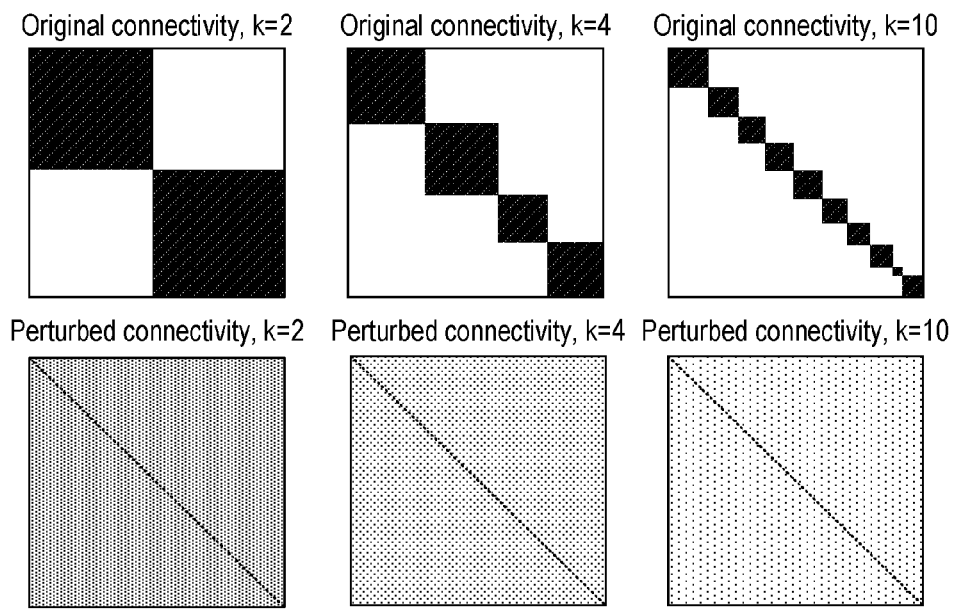

FIG. 2B shows the original connectivity matrices (upper row) and perturbed connectivity matrices (lower row). For each value of k, PINS partitions the original data and then builds the connectivity matrix. The elements in one cluster are all connected to each other and are disconnected to elements of other clusters. For example, when k=2, PINS forms 2 clusters of approximately equal sizes from the original data. However, when the data are perturbed, each data point randomly moves around its original location and thus it can be grouped together with any other point with the same probability. By perturbing the data, we construct 200 connectivity matrices $G_2^{(h)}, h \in [1 \ldots 200]$. The perturbed connectivity matrix is then calculated as the average of these 200 matrices:

$$A_2 = \frac{\sum_{h=1}^{200} G_2^{(h)}}{200}$$

Visually, the perturbed connectivity matrix $A_2$ in panel (B) shows that data points are randomly connected. This is also true for any other value of $k \in [2 \ldots 10]$. In summary, the original connectivity greatly disagree with the perturbed connectivity, which reflects the real structure of the data.

Figure 2C:
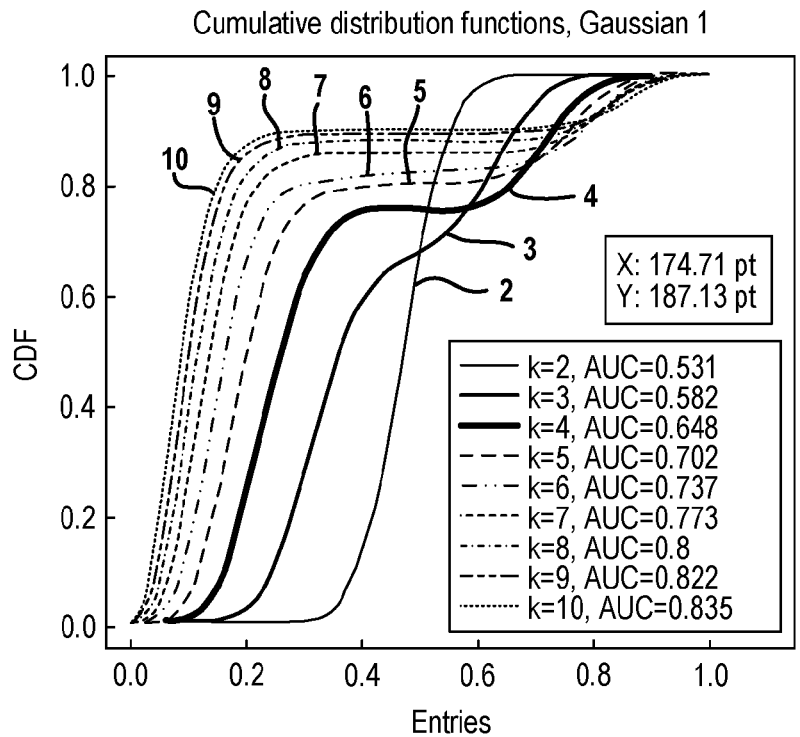
Figure 2D:
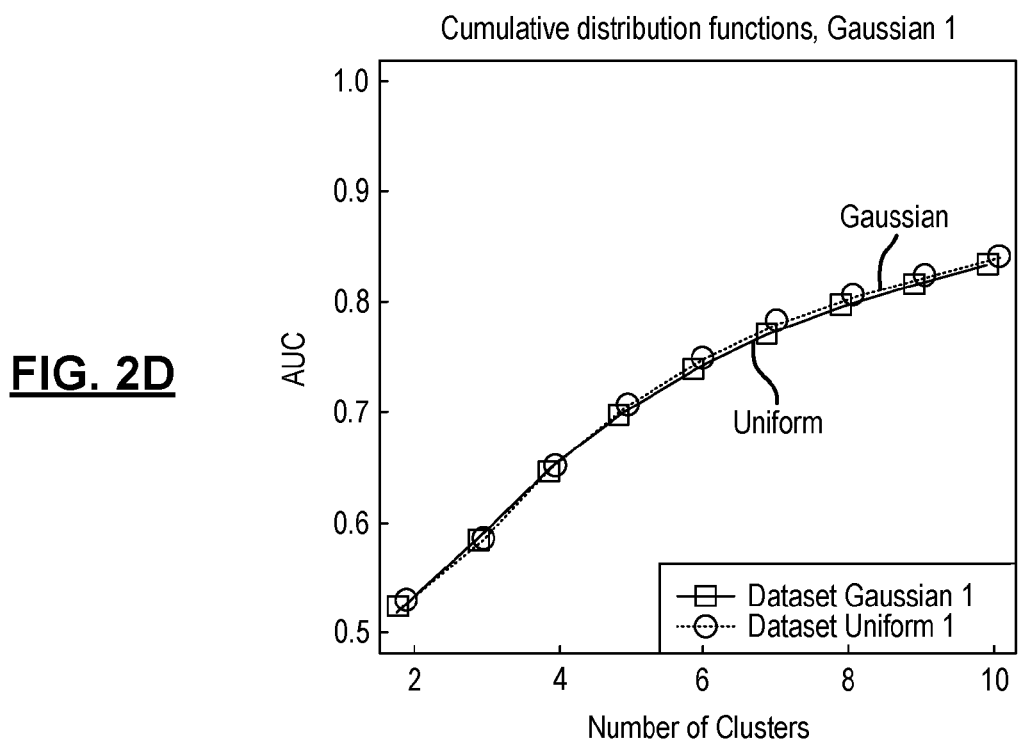

FIG. 2C displays the CDFs of the entries of the difference matrices for all values of $k \in [2 \ldots 10]$. The horizontal axis represents the entries of the difference matrix while the vertical axis represents the values of the CDFs. Panel (D) shows the area under the curve (AUC) of the CDFs. The horizontal axis shows the number of clusters and the vertical axis shows the AUC values. To understand the variability of the AUC values, we repeat the whole process 20 times with different simulated datasets having normally distributed gene expression. The vertical lines show the 95% confidence interval of the AUCs at each value of k. The AUC values barely change when the data change. We also plot the AUC values for a simulated dataset with uniformly distributed expression values. The figure shows that when the data are random, regardless of their distribution, the AUC values vary only slightly. In addition, these AUC values monotonically increase with k, and range from 0.5 to 0.85, which is notably smaller than 1.

As we understand the behavior of PINS for random data, we would like to know how PINS works on datasets that have separable classes. FIG. 3 displays the workflow of PINS for the simulated dataset Gaussian2 (2 classes). The dataset consists of 100 samples and 1,000 genes. Panel (A) shows the gene expression of the 2 cluster, in which each cluster has 50 samples. The samples of the first cluster has the genes 1-100 up-regulated while the second cluster has the genes 101-200 up-regulated. These up-regulated genes are normally distributed with mean 2 and variance 1 (N(2, 1)). Other genes are normally distributed with mean 0 and variance 1 (N(0, 1)).

Figure 3A:
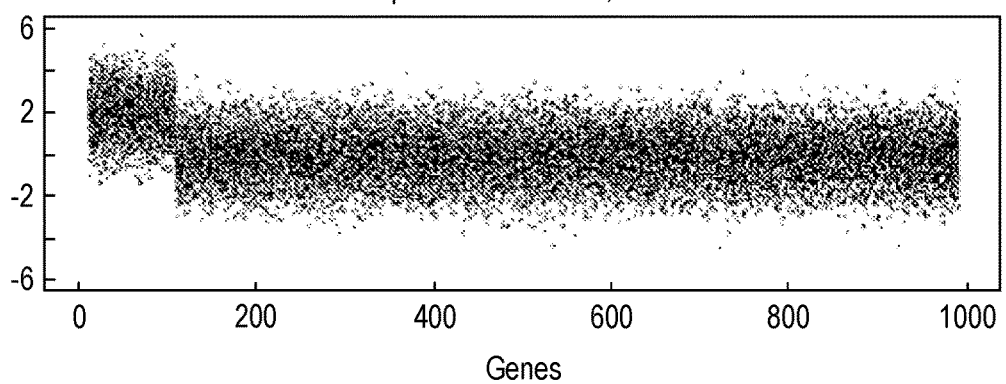
FIGS. 3A-3D (collectively referred to as FIG. 3) depicts a second exemplary dataset (Gaussian2-2 classes) associated with the perturbation clustering process of FIG. 1, the individual FIG. 3 Panels (A)-(D) displaying comparable information as described in connection with FIG. 2.
Figure 3A:
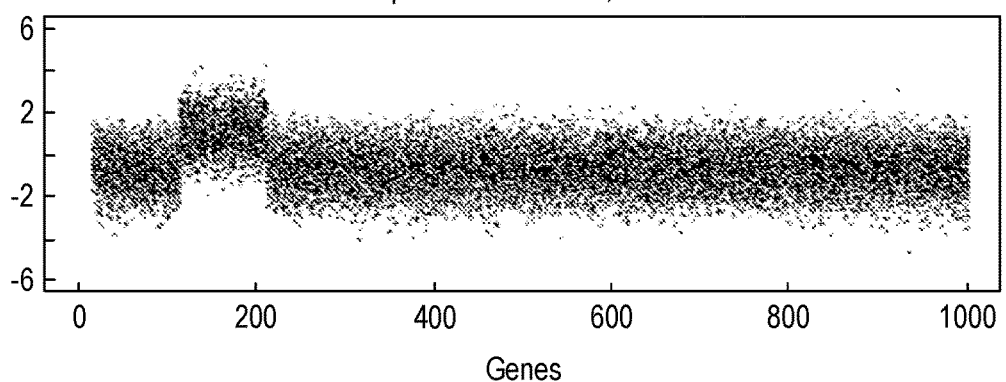
Figure 3B:
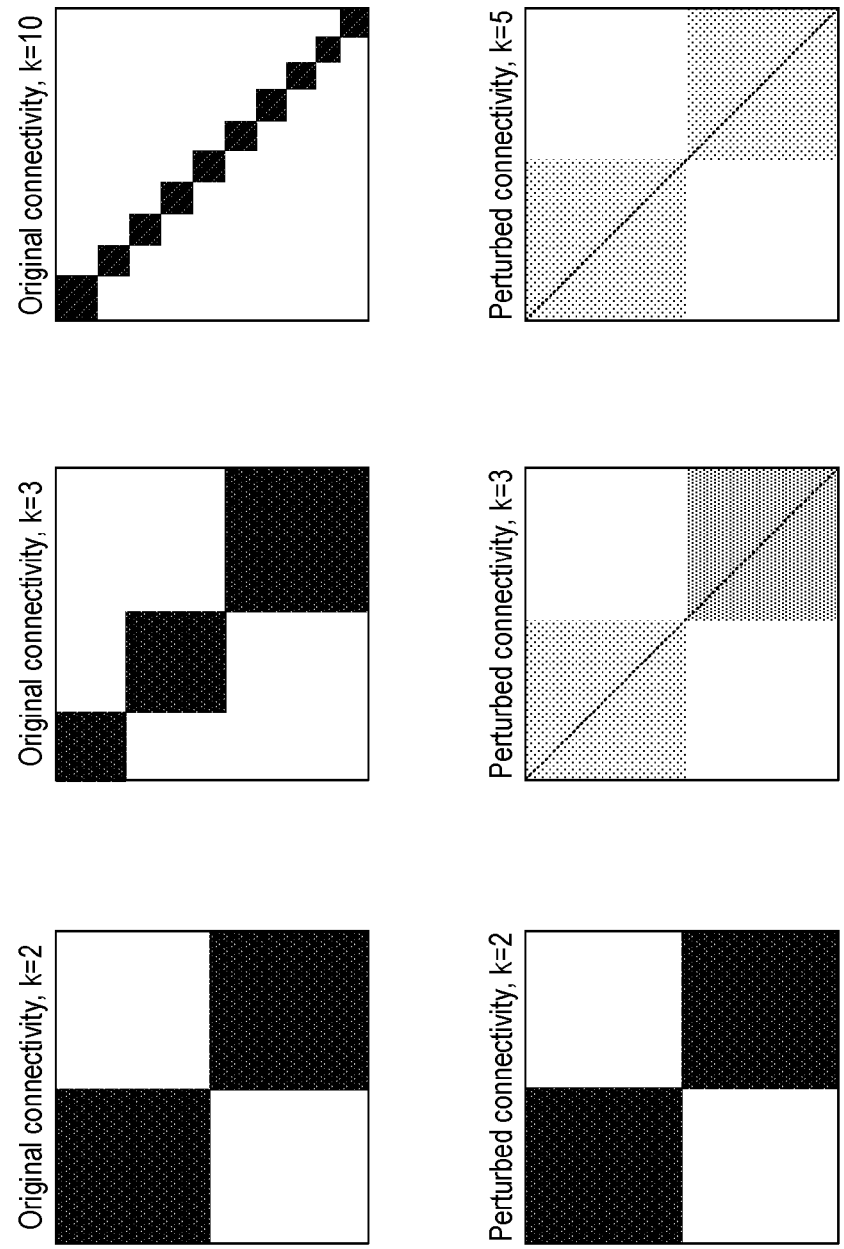
Figure 3C:
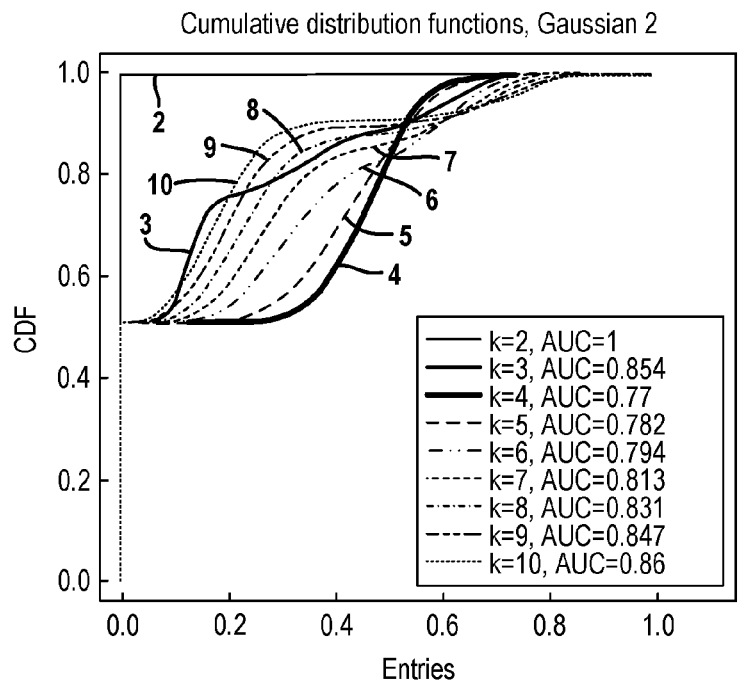
Figure 3D:
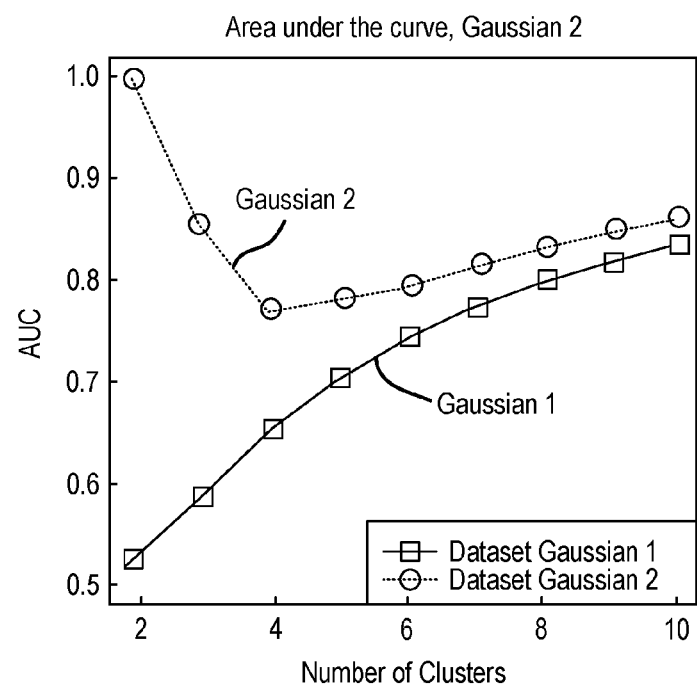

FIG. 3B shows the original connectivity matrices (upper row) and the perturbed connectivity matrices (lower row) of the simulated dataset Gaussian2. Using the original data, the basic k-means algorithm correctly separate the 2 classes when k=2. As we perturb the data, each data point moves around its original position but still stays close to its own cluster. Therefore, samples of the same cluster are still grouped together, making the perturbed connectivity matrix identical to the original connectivity matrix when k=2.

When k>2, the original connectivity matrices show that the k-means algorithm further split the data into smaller groups. However, when the data are perturbed, the connectivity between data points of the same cluster, which were mistakenly separated, tend to recover. Regardless of the value of k being used, the perturbed connectivity matrices clearly show that the data consists of 2 clusters, which is the true structure of the dataset Gaussian2. Panel (C) shows the CDFs of the difference matrix while panel (D) shows the AUC values of the CDFs. Since the original and perturbed connectivity matrices are identical for k=2, we have $F_2(0)=1$ and $AUC_2=1$. In other words, $P_2$ is the only partitioning that is stable against data perturbation, and therefore $\hat{k}=2$ is the optimal number of clusters for the dataset Gaussian2. PINS correctly and deterministically discovers the true classes of the dataset Gaussian2.

FIG. 4 displays the workflow of PINS for the simulated dataset Gaussian3. Panel (A) shows the expression of the 3 classes. Each of the first and second classes have 33 samples while the third class has 34 samples (totally 100 samples). The first class has the genes 1-100 up-regulated; the second class has the genes 101-200 up-regulated; the third class has the genes 200-300. These up-regulated genes are normally distributed with mean 2 and variance 1 (N(2, 1)). Other genes are normally distributed with mean 0 and variance 1 (N(0, 1)).

Figure 4A:
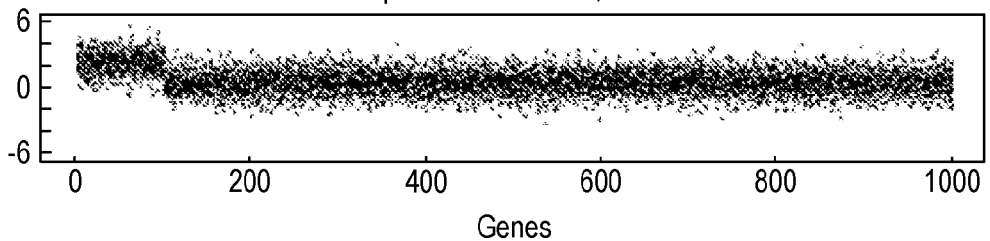
FIGS. 4A-4D (collectively referred to as FIG. 4) depicts a second exemplary dataset (Gaussian3-3 classes) associated with the perturbation clustering process of FIG. 1, the individual FIG. 4 Panels (A)-(D) displaying comparable information as described in connection with FIG. 2.
Figure 4A:
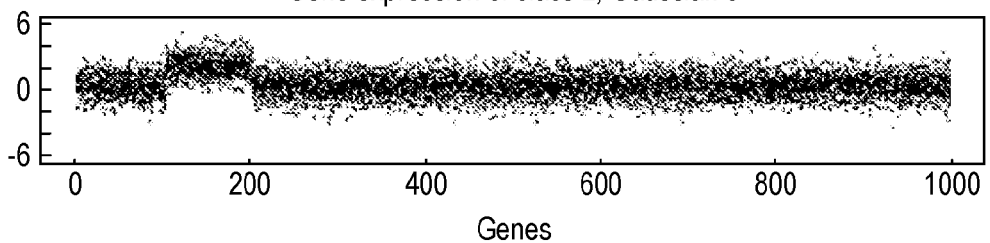
Figure 4A:
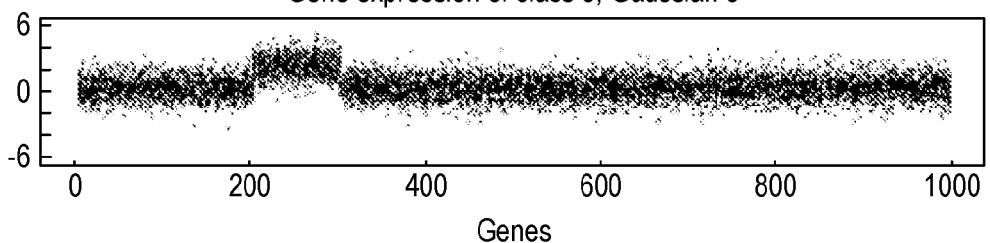
Figure 4B:
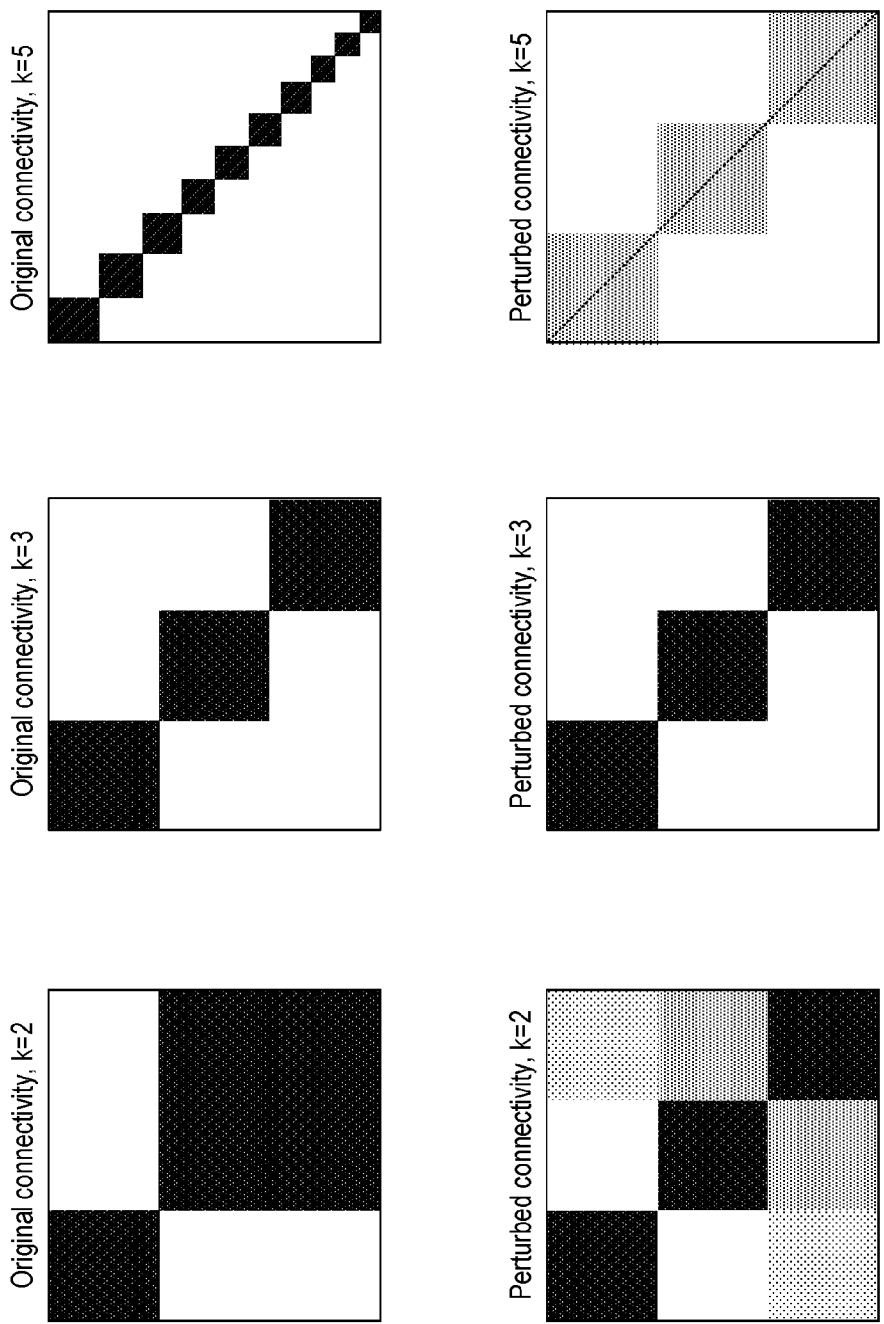

FIG. 4B shows the original connectivity matrices (upper row) and perturbed connectivity matrices (lower row). For k=3, the basic k-means algorithm correctly separate the 3 classes using the original data. As we perturb the data, samples of the same class are still grouped together, making the perturbed connectivity matrix identical to the original connectivity matrix. For k>3, the k-means algorithm further splits each class into smaller groups. However, when the data are perturbed, samples of the same class tend to connect to each other. For k=2, the original connectivity matrix $C_2$ shows that 2 of the 3 classes are merged but the connectivity between them is not stable when the data are perturbed. The perturbed connectivity matrices clearly suggest that the data consists 3 groups of samples, which is the true structure of Gaussian3.

Figure 4C:
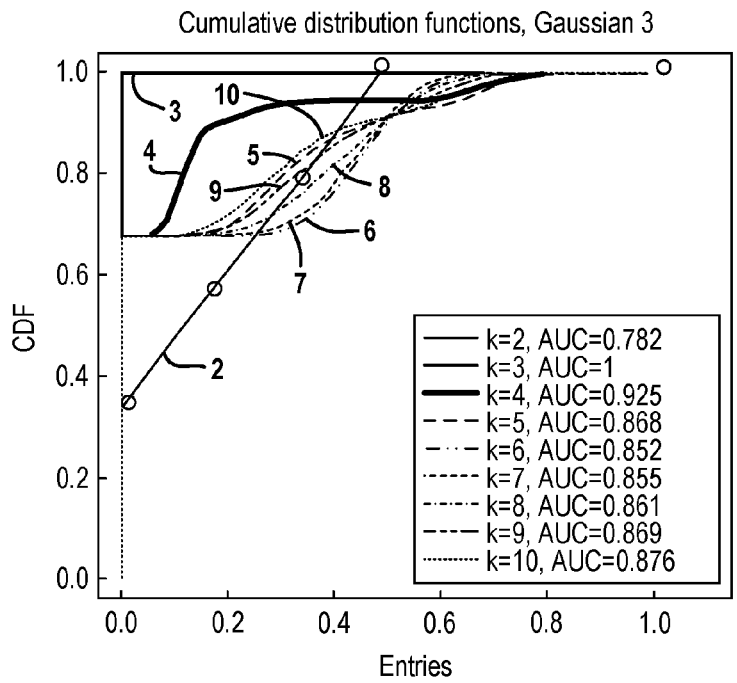
Figure 4D:
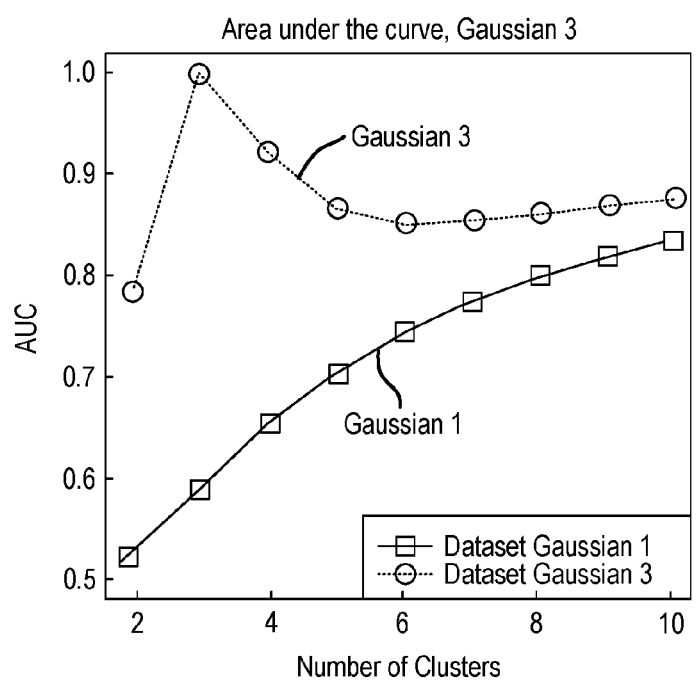
Figure 5A:
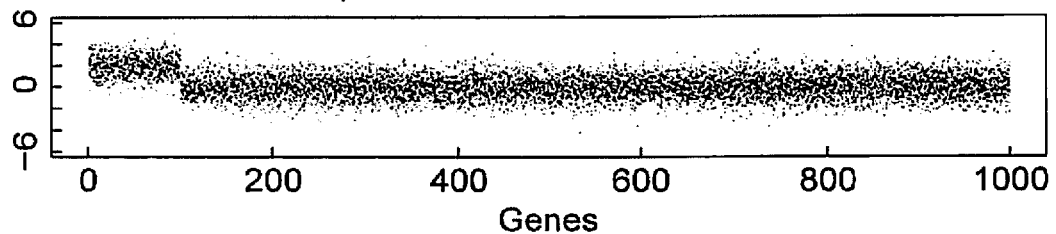
FIGS. 5A-5D (collectively referred to as FIG. 5) depicts a second exemplary dataset (Gaussian5-5 classes) associated with the perturbation clustering process of FIG. 1, the individual FIG. 5 Panels (A)-(D) displaying comparable information as described in connection with FIG. 2.
Figure 5A:
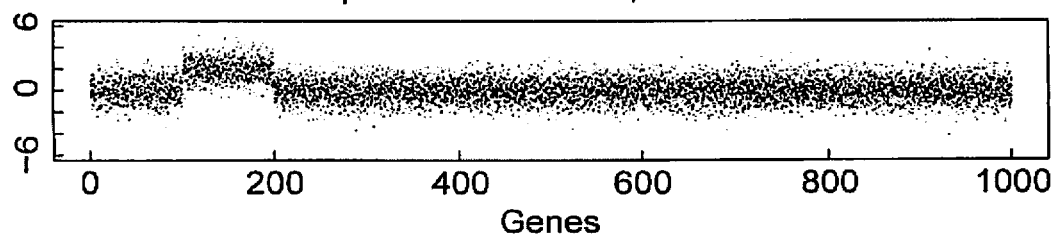
Figure 5A:
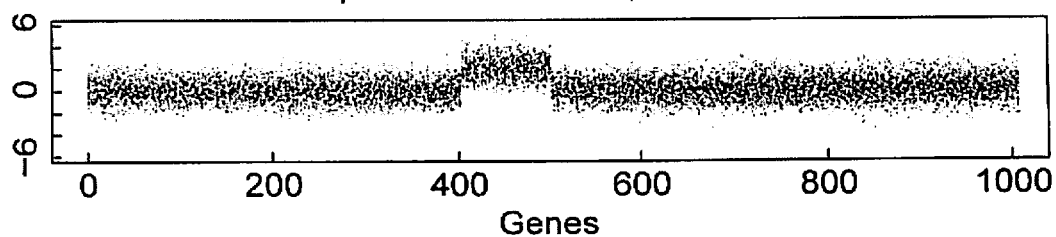
Figure 5B:
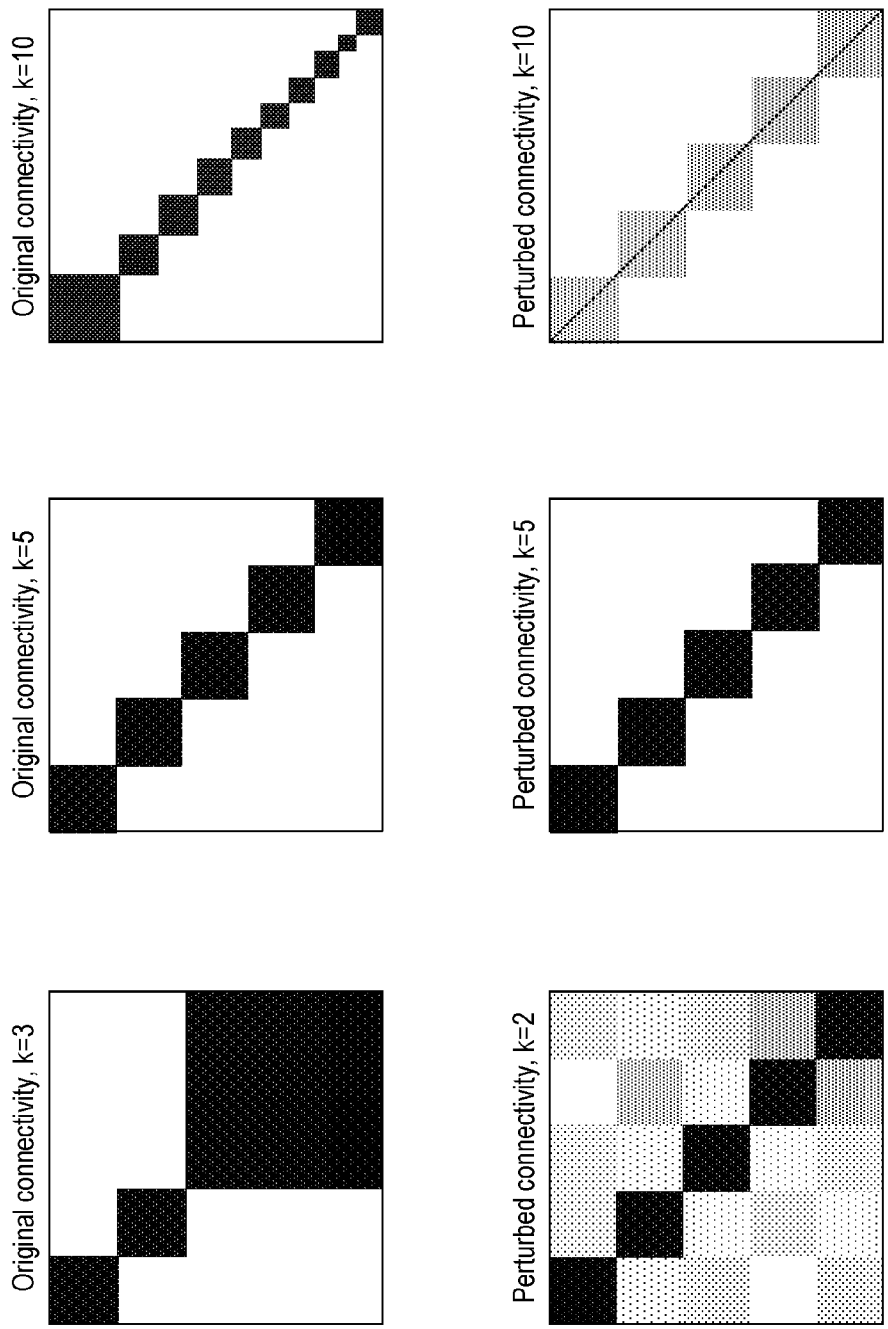
Figure 5C:
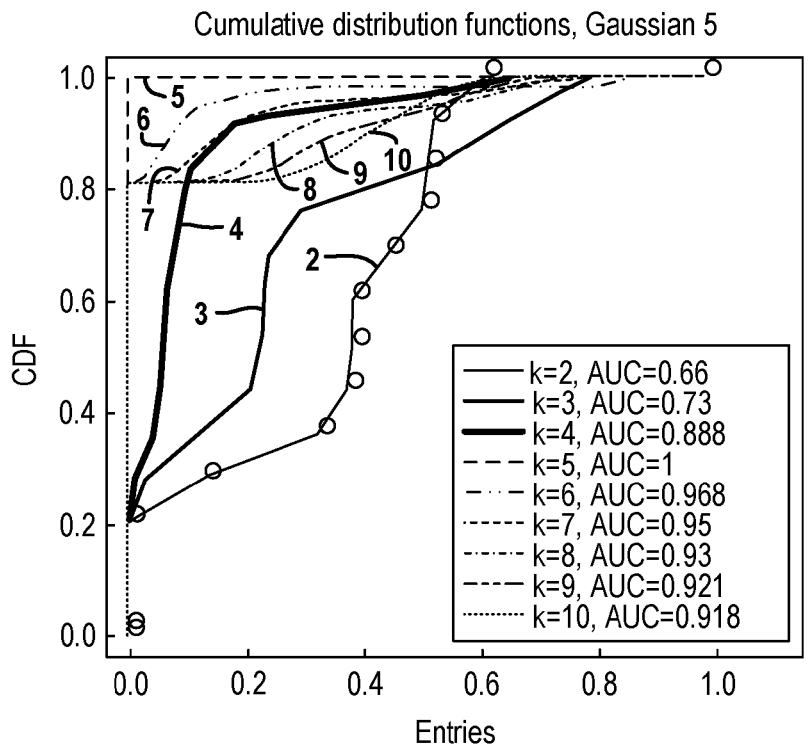
Figure 5D:
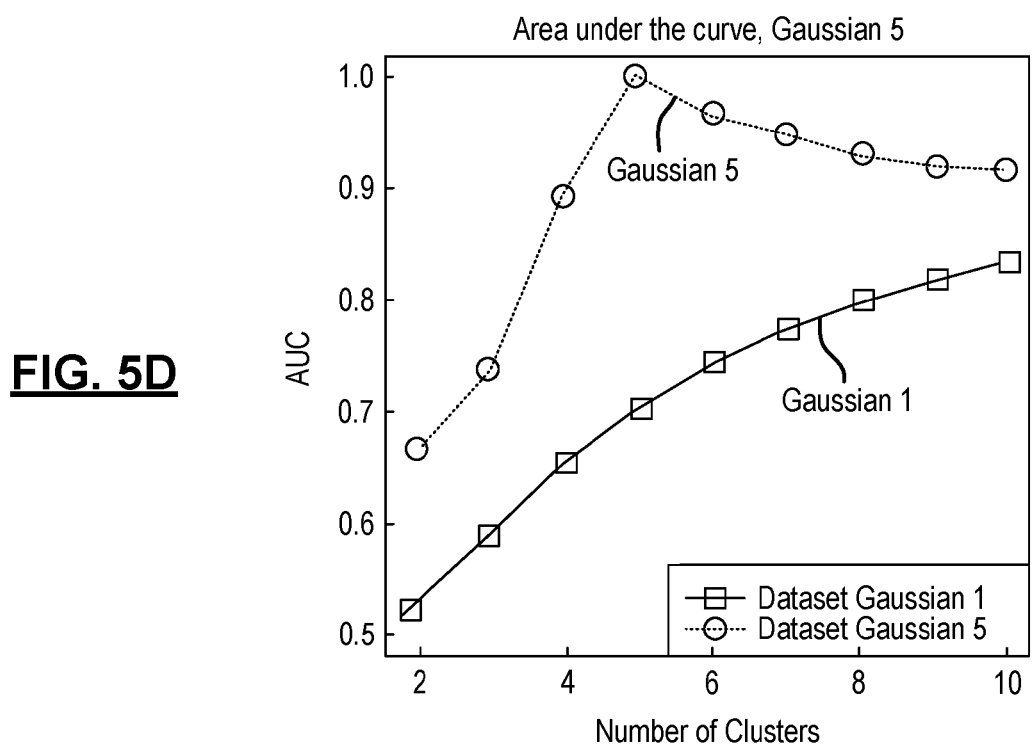
Figure 6A:
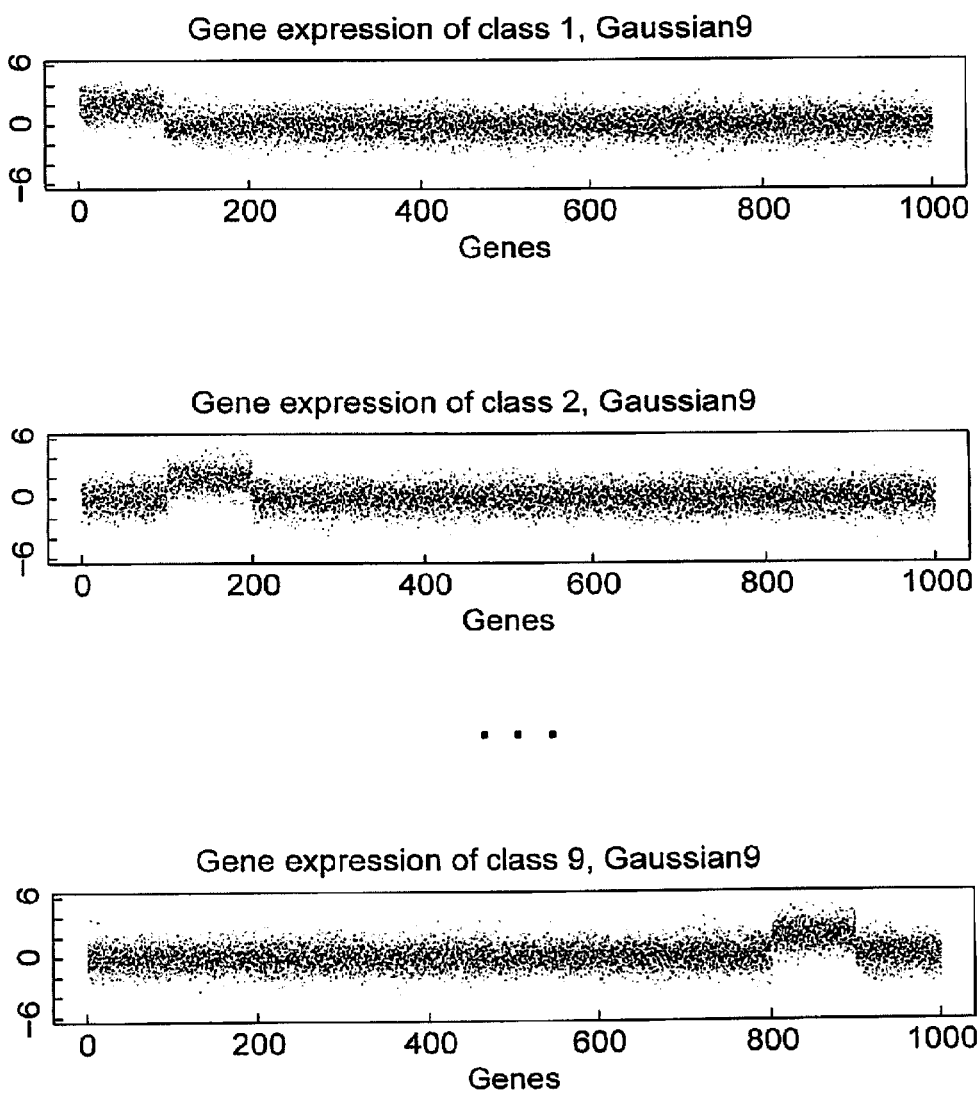
FIGS. 6A-6D (collectively referred to as FIG. 6) depicts a second exemplary dataset (Gaussian9-9 classes) associated with the perturbation clustering process of FIG. 1, the individual FIG. 6 Panels (A)-(D) displaying comparable information as described in connection with FIG. 2.
Figure 6B:
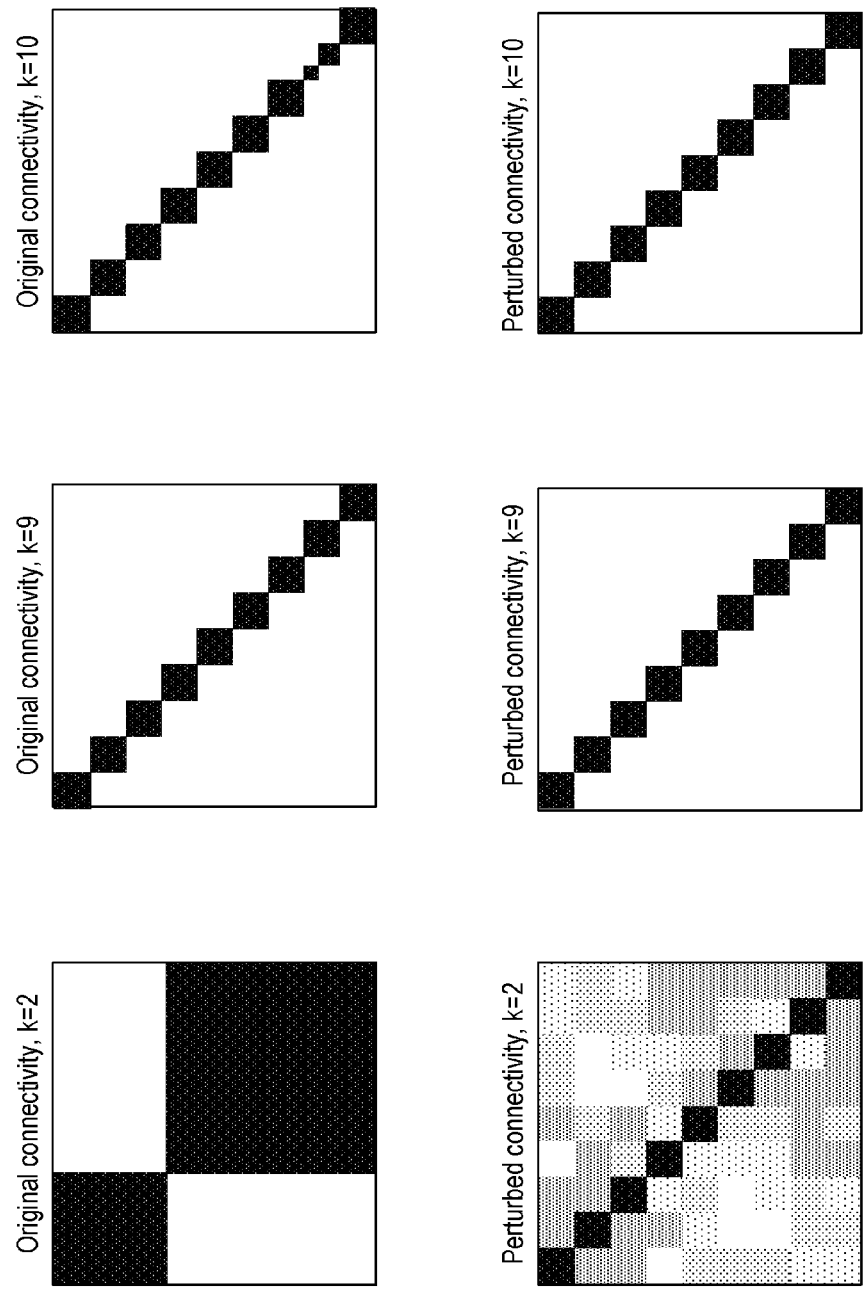
Figure 6C:
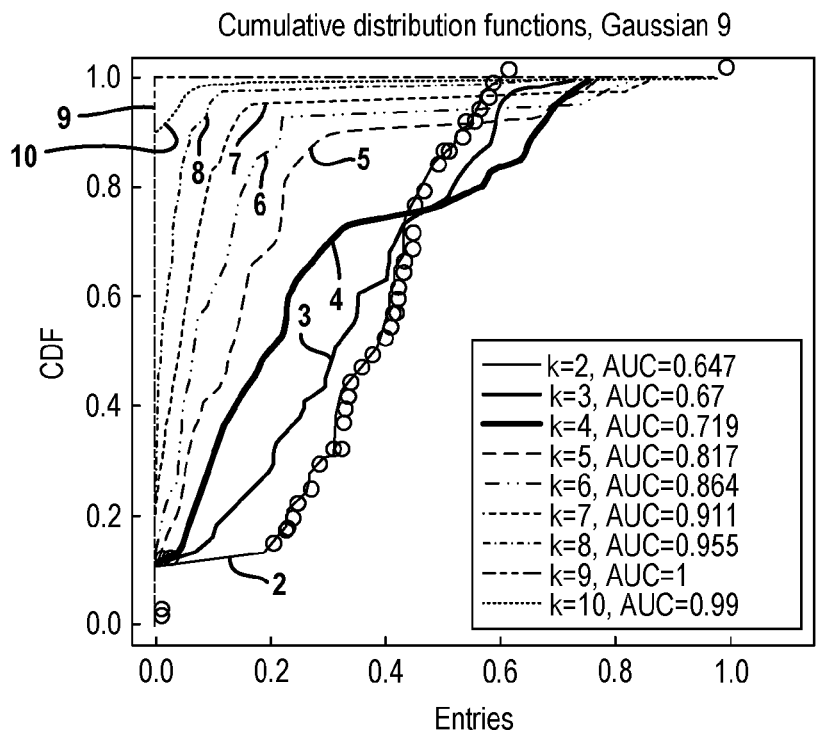
Figure 6D:
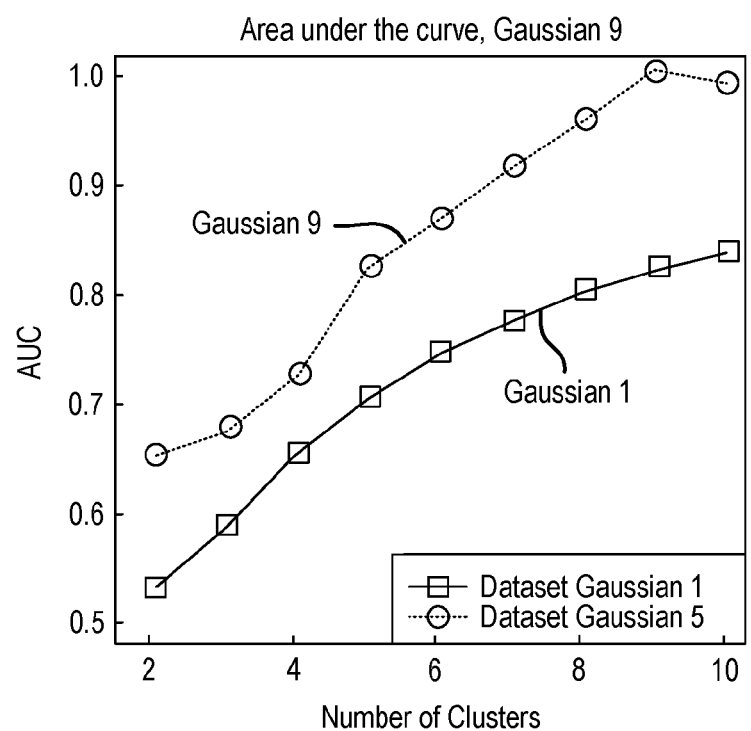

FIG. 4C displays the empirical cumulative distribution functions (CDF) $F_k$ of the difference matrix $D_k$, $K \in [2 \ldots 10]$. The horizontal axis represents the entries of the difference matrix while the vertical axis displays the values of the function (the number of elements in $D_k$ smaller or equal to each entry). Panel (D) shows the area under the curve (AUC) of the CDFs. The horizontal axis shows the number of clusters and the vertical axis shows the AUC values. The AUC curve shows that only the partitioning $P_3$ is stable against data perturbation, i.e., $\hat{k}=3$. PINS correctly and deterministically discovers the true classes of the dataset Gaussian3.

Similarly, FIGS. 5 and 6 display the workflow of PINS for the simulated datasets Gaussian5 (5 classes) and Gaussian9 (9 classes). In both cases, the perturbed connectivity matrices clearly show the true structure of the data, regardless of the value of k being used. We note that for these two datasets, the noise variance is set to the median variance of the genes, which can be higher than the real noise. For example with Gaussian9, only that last 100 genes have variance equal to the noise variance. The other 900 genes have variance higher than the noise variance because there is at least one cluster having those genes up-regulated. Even in these cases, PINS still correctly identify the number of clusters with the optimal AUC equals to 1.

Figure 7:
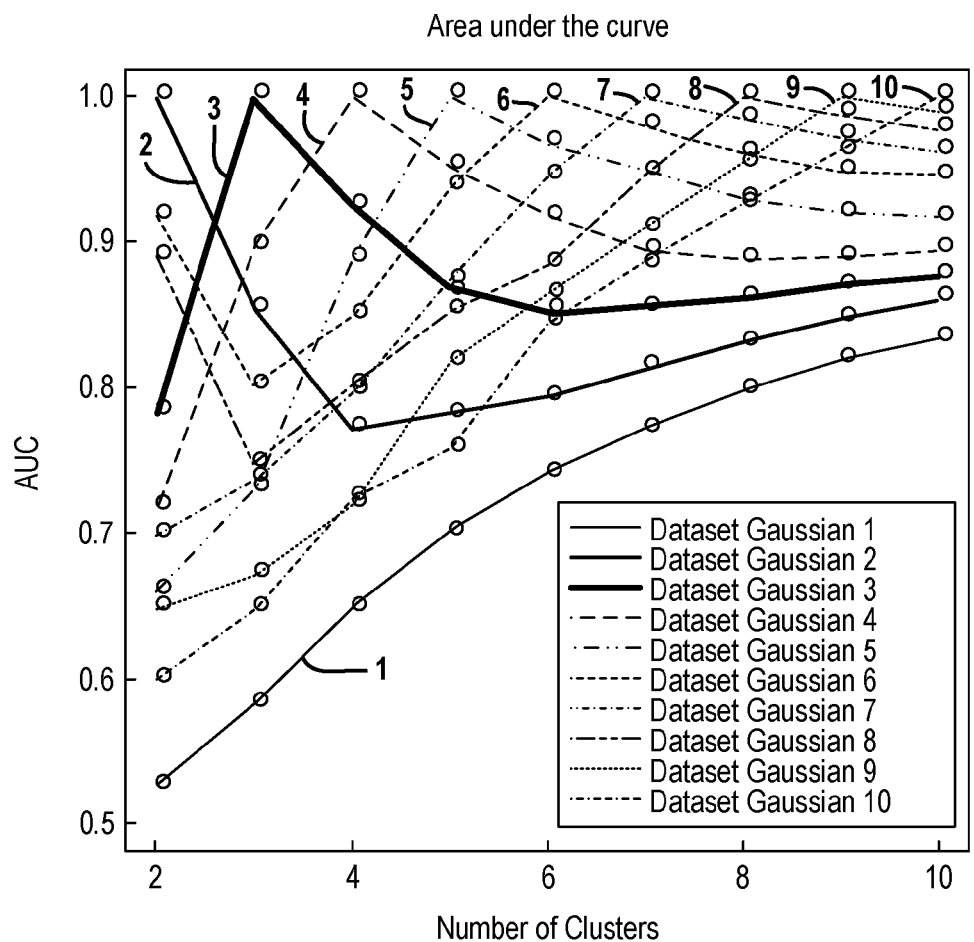
FIG. 7 is an area under the curve (AUC) graph for ten (10) simulated datasets.
Figure 8A:
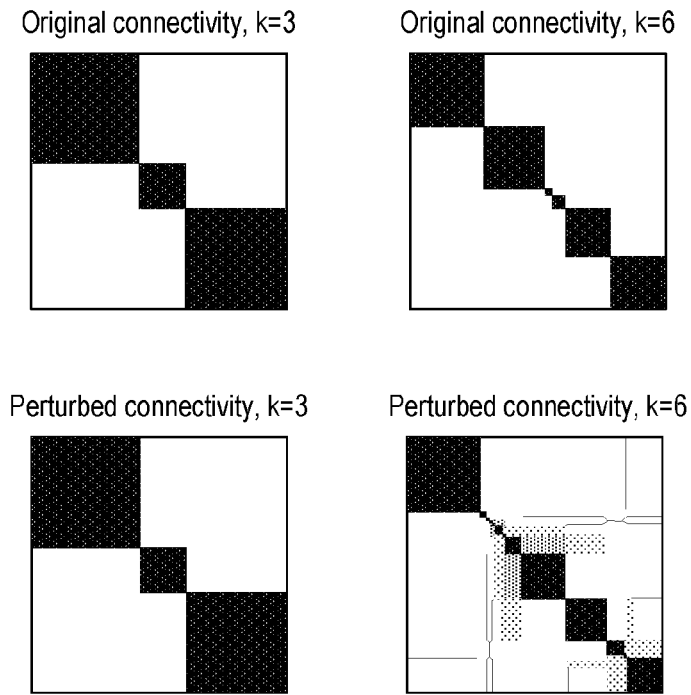
FIGS. 8A-8D (collectively referred to as FIG. 8) depict data for the lung cancer dataset GSE19188, useful in understanding the disclosed clustering technique, specifically.
Figure 8B:
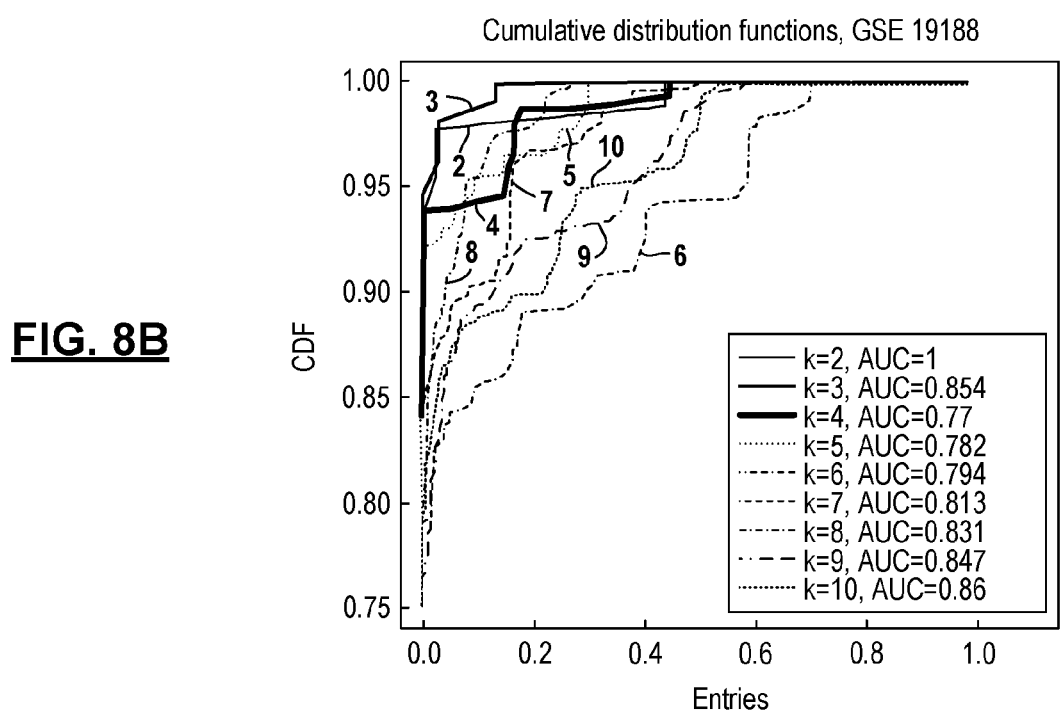
Figure 8C:
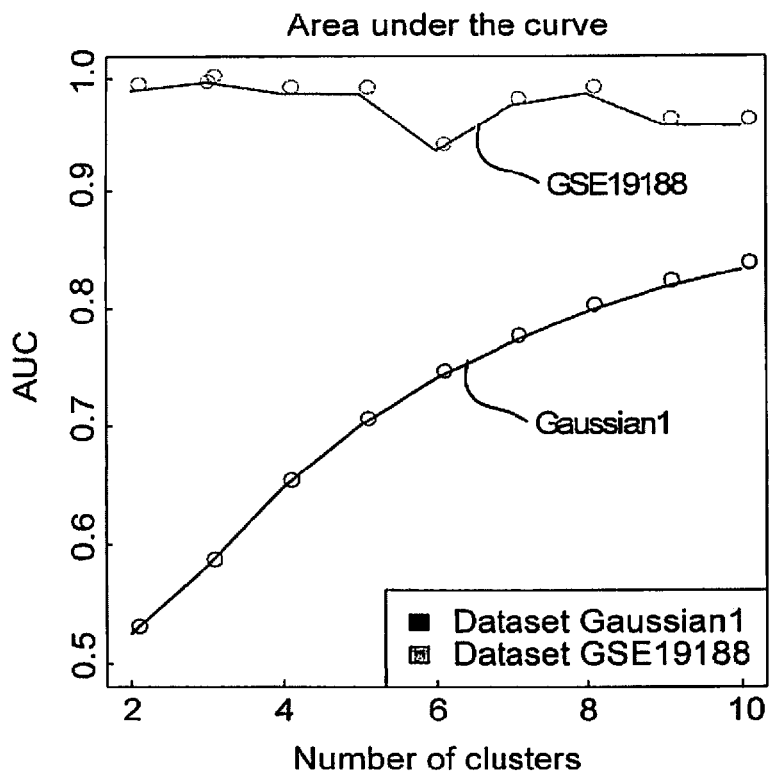
Figure 8D:
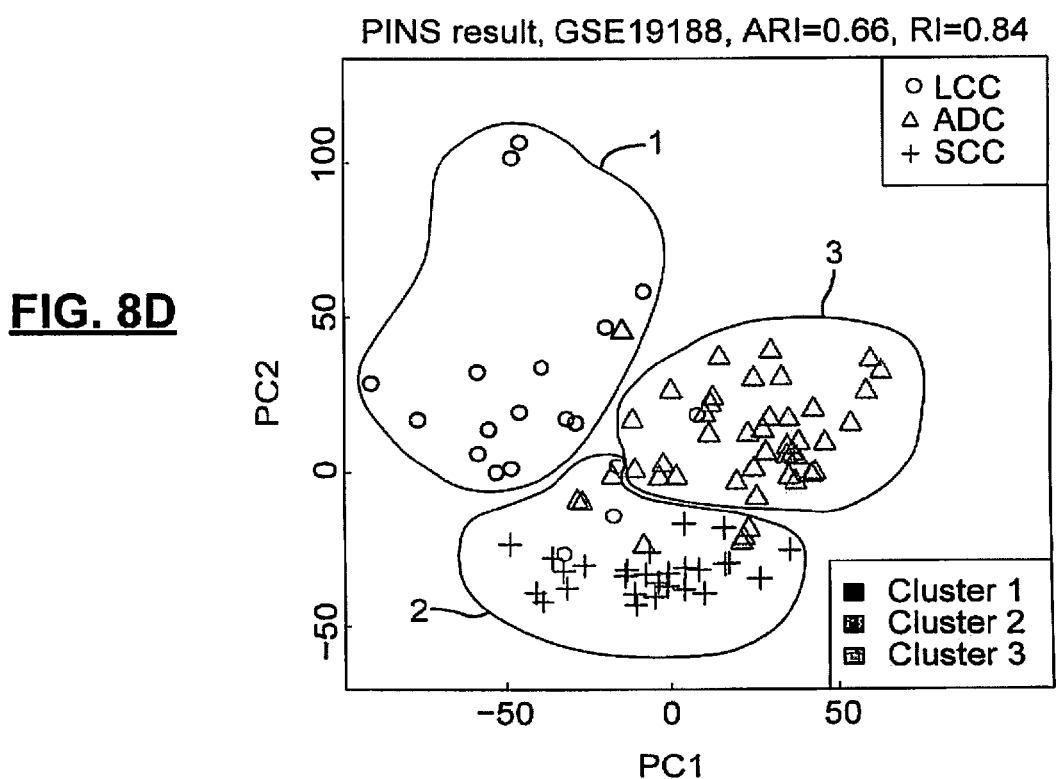

As a summary, we display the AUC values of all the 10 simulated datasets from Gaussian1 to Gaussian10 in FIG. 7. The number in the name of each simulated dataset is the number of classes in that dataset. When the data have no structure as in Gaussian1, the AUC values monotonically increase with k, and range from 0.5 to 0.85. These AUC values vary only slightly regardless of the gene expression variance or distribution (FIG. 2). In addition, for any value of k, the AUC value of Gaussian1 is always smaller than the AUC value of any other dataset that has a clear structure. When the data consist of more than 1 class, the AUC values greatly increase and reach the maximum value when the number of cluster equals to the number of classes. PINS correctly identify the optimal number of clusters k with $AUC_{\hat{k}}=1$ for all these 9 simulated datasets.

FIG. 8 shows and example of the real dataset GSE19188PINS result for the real dataset GSE19188, which consists of 91 lung cancer samples and 19,851 genes. The dataset has 3 subtypes: 45 adenocarcinomas (ADC), 19 large cell carcinoma (LCC), and 27 squamous cell carcinomas (SCC). The goal is to cluster the samples according to their subtypes using the gene expression. Panel (A) shows the connectivity matrices for k=3 and k=6. Visually, the perturbed and original connectivity matrices are almost identical for k=3 and are greatly different for k=6. Panel (A) displays the CDF of the different matrices for $k \in [2 \ldots 10]$. The CDF for k=3 reaches its maximum quickly, which reflects the fact that the partitioning $P_3$ is the most stable among other partitionings. Panel (C) displays the AUC values, in which $AUC_3$ has the highest value and thus k=3. Panel (D) displays the clustering result in the first two principal components. The circles represent the LCC samples; the triangles represent the ADC samples; the crosses represent the SCC samples. PINS correctly identifies the number of the subtypes and separate most of the samples accordingly with high Rand index (RI) and adjusted Rand index (ARI). More details about the real datasets will be explained in the Experimental Results section below.

Figure 30:
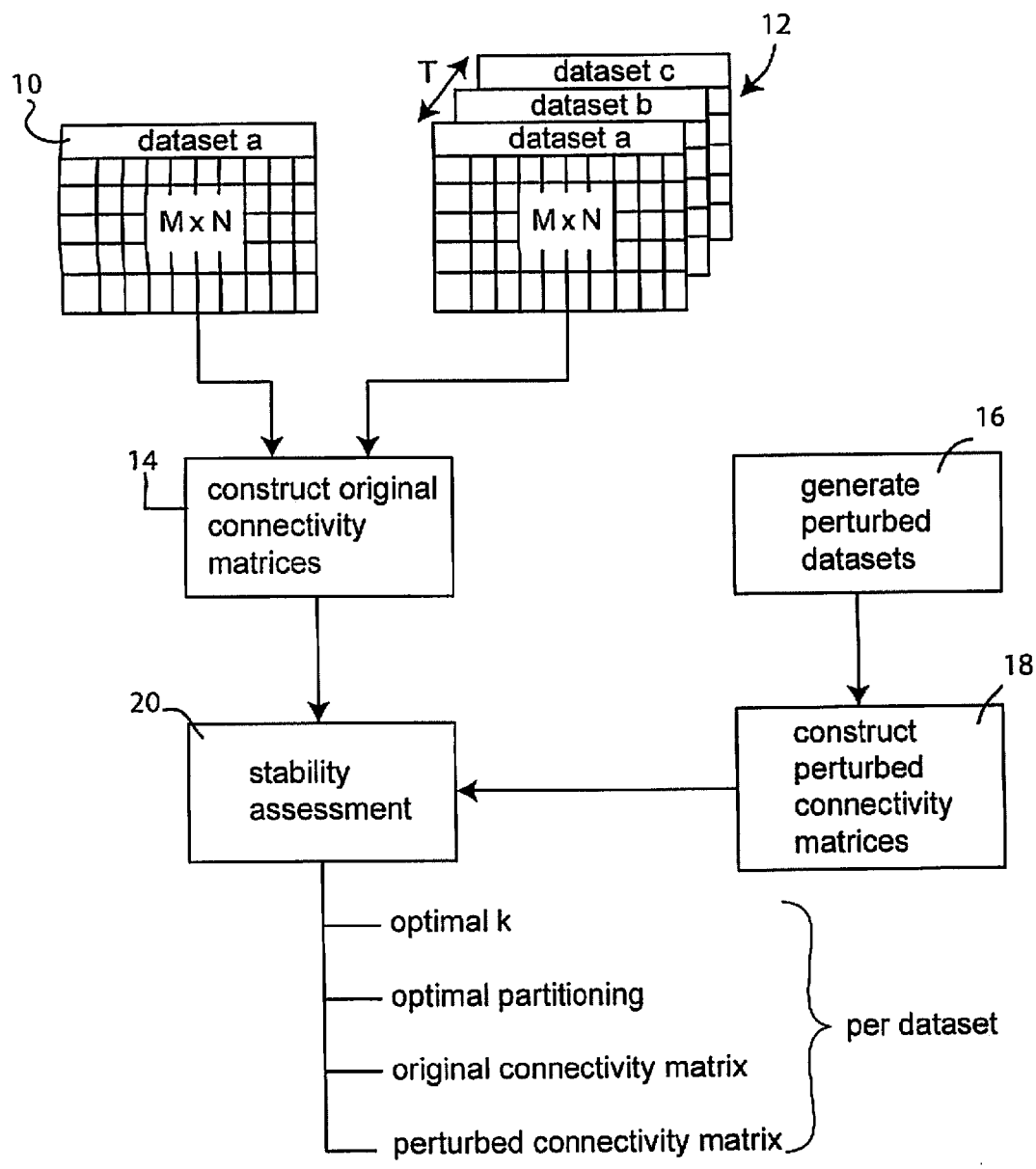
FIG. 30 is a simplified flow diagram depicting the major steps of the disclosed PINS technique.

Before moving to a detailed discussion of how subtyping of multi-omics data are processed, FIG. 30 will be used to summarize what has been described in detail above and also to illustrate how multi-omics data can be introduced into the analysis. The process begins by supplying a dataset, such as dataset 10, which represents a single data type (such as mRNA data), or dataset 12, which represents a collection of plural datasets, each of a different data type (such as mRNA, DNA methylation, and miRNA). The dataset can be generated by collecting human tissue samples, analyzing those samples using a laboratory genetic analyzer and storing in a MxN array in non-transitory computer memory, where M represents an element of the data type and N represents the individual person from whom the sample was collected. Suitable datasets can be obtained from previously developed sources available commercially and/or from the Internet.

Whether a single dataset 10 or a multi-omics dataset 12 is being used, the dataset is processed to construct the original connectivity matrices 14, as described in detail above. In parallel with the original connectivity matrices construction, perturbed datasets are generated as at 16. This is done, as described above by injecting a suitably configured Gaussian noise into the data. The perturbed datasets are then used to construct perturbed connectivity matrices 18.

With original and perturbed connectivity matrices now both constructed, a stability assessment is performed at 20. As a result of this assessment, the computer-implemented algorithm identifies several important data values that describe the optimal clusters for the given datasets. These data values include, the optimal value of k, designating the optimal number of clusters; and the optimal partitioning of the dataset, indicating to which cluster each person's data belongs. In addition, the algorithm stores the original connectivity matrix and the perturbed connectivity matrix, for use in subsequent processing steps. Note that the stability assessment step defines these data values for each dataset supplied. Thus if the dataset 10 was used, a single optimal k value and single optimal partition would be generated. If dataset 12 were instead used, the stability assessment step would generate a separate optimal k value for each data type (e.g., mRNA, DNA methylation, and miRNA) and a separate optimal partition for each data type as well.

Note that the process illustrated in FIG. 30 represents unclassified clustering. The process finds the optimal clusters without requiring any a priori knowledge of how the individual subjects may have been classified (if at all) prior to performing the process. Essentially, the process describe in FIG. 30 and above, uses the raw dataset data to find the optimal clusters, without any requirement that a k value be selected in advance.

B. Subtyping Multi-Omics Data

In this section, we describe the workflow of PINS for multi-omics data. Let us denote T as the number of data types. The input of PINS is a set of T matrices where $\|=\{I_1, I_2, \ldots, I_T\}$ where $I_i \in R^{N \times M_i}$ represents the measurements of the $i^{th}$ data type, N is the number of patients, and $M_i$ is the number of measurements per patient for the $i^{th}$ data type. The T matrices have the same number of rows (patients) but might have different number of columns.

Our disclosed workflow consists of two stages: i) integrate the data and cluster the patients, ii) further split each group into subgroups if possible. In stage I, we construct the combined similarity matrix between patients using the connectivity information from individual data types. We then combine 3 similarity-based algorithms to determine the final partitioning of the multi-omics data. In stage II, we further split each discovered subtype if possible.

1) Stage I—Data Integration and Subtyping:

The algorithm starts by clustering each data type using the perturbation clustering (as described above). Consider the $i^{th}$ data type with the data matrix $I_i$. The perturbation clustering estimates $\hat{k}_i$ as the number of clusters and then partitions the data into $\hat{k}_i$ clusters. The algorithm returns the original connectivity matrix $C_i$, in which the connectivity between elements of the same clusters is 1 and the connectivity between elements of different clusters is 0. Please note that the index i here denotes the index of the data type. For T data types, we have T original connectivity matrices $C_1$; $C_2; \ldots; C_T$. We combine the connectivity matrices for the original data as follows:

$$S_C = \frac{\sum_{i=1}^{T} C_i}{T} \tag{9}$$

We refer to $S_C$ as the original similarity matrix because it is constructed from the original connectivity matrices. If we consider each patient as a node, and the connectivity between two patients is an edge, then each connectivity matrix for each data type represents a graph. Our goal is to identify subgraphs that are strongly connected across all data types.

We then measure the agreement between the T data types using the concept similar to the pair-wise agreement of Rand index (RI). Given two partitionings of the same set of items, the RI is calculated as the number of pairs that "agree", divided by the total number of possible pairs. A pair "agrees" if the two samples are either grouped together in both partitionings or they are separated in both partitionings. We extend this concept to T partitionings of T data types. First we defined that the connectivity between two patients is consistent if it does not change across data types. We then define the agreement of T data types as the number of pairs having consistent connectivity, divided by the total number of possible pairs. In other words, the agreement between the data types can be calculated as follows:

$$\text{agree}(S_C) = \frac{|\{S_C(i,j) = 0 \vee S_C(i,j) = 1\}|}{N^2} \tag{10}$$

If the majority of pairs are consistent, i.e., agree($S_C$) >50%, we say that the T data types have strong agreement. In this case, we define a strong similarity matrix $\hat{S}_C$ as follows:

$$\hat{S}_C(i,j) = \begin{cases} 1 & \text{if } S_C(i,j) = 1 \\ 0 & \text{otherwise} \end{cases} \tag{11}$$

where $\hat{S}_C(i,j)=1$ if and only if i and j are clustered together in all data types and 0 otherwise. A hierarchical clustering is then applied on this matrix and the resulting tree is cut at the height that provides maximum cluster separation.

When the data types do not have strong agreement, we perform a cluster ensemble of 3 different methods as will be explained as follows. The matrix $\{S_C(i,j)\}$ represents the similarity between patients, and therefore $\{1-S_C(i,j)\}$ represents the pair-wise distance between patients, which can be directly used by similarity-based clustering algorithms, such as hierarchical clustering, partitioning around medoids, or dynamic tree cut. Here we use all the 3 algorithms to partition the patients and then choose the partition that agrees the most with the partitionings of individual data types. The dynamic tree cut algorithm can automatically determines the number of clusters, but the other two algorithms, hierarchical clustering (HC) and partitioning around medoids (PAM), need us to provide the number of clusters.

To determine the number of clusters for HC and PAM, we introduce the perturbed similarity matrix, which can be calculated as follows:

$$S_A = \frac{\sum_{i=1}^{T} A_i}{T} \tag{12}$$

where $A_i$ is the perturbed connectivity matrix of the $i^{th}$ data type. Please note that $S_C$ is constructed by averaging the original connectivity of T data types while $S_A$ is constructed by averaging the perturbed connectivity of T data types. We use this both matrices to assess the stability of HC and PAM.

For hierarchical clustering, we first build the $H_1$ tree using the original similarity matrix $S_C$, and then we build the $H_2$ tree using the perturbed similarity matrix $S_A$. For each value of k, we cut $H_1$ to get k clusters and then build the connectivity matrix. We do the same for $H_2$ and then calculate the instability $d_k$ as the sum of absolute difference between the two connectivity matrices. We choose $\hat{k}$ for which the $d_k$ is the smallest, i.e., $\hat{k} = \text{argmax}_k(d_k, k \in [2 \ldots K])$.

Similarly for PAM, we partition the patients using both original and perturbed similarity matrices. For each value of k, we have one partitioning using the original similarity matrix $S_C$ and one partitioning using the perturbed similarity matrix $S_A$. We build the connectivity matrices from the two partitioning and then calculate the instability $d_k$ as the absolute difference between the two connectivity matrices. We choose $\hat{k}$ for which the $d_k$ is the smallest, i.e., $\hat{k}=\text{argmax}_k (d_k, k \in [2 \ldots K])$ After having the 3 partitionings using the 3 similarity-based clustering algorithms, we calculate the agreement between each partitioning and the T data types. Again, we use the agreement concept introduced in Equation (10). For each algorithm, we calculate the agreement between its partitioning and the T partitionings for the T data types. We then choose the result of the algorithm that has the highest agreement with the T data types.

2) Stage II—Splitting Groups into Subgroups

In stage II, we further split one discovered group of patients at a time, if possible. We check each group independently. If a group has more than ⅔ of the total samples, we run the procedure described in stage I again, but this time the input consists of only the patients belonging to the group we are working on. The goal is to separate samples of this group, that would not be possible with the presence of samples from other groups.

If a group has less than ⅔ but more than ⅓ of the total samples, we need to check the agreement between the T data types. We take into consideration only the samples belonging to this group. We cluster each data type and build the T connectivity matrices. Here we calculate the agreement between the data types using Equation (10). If the agreement is more than 50% (i.e., the majority of pairs agree across all data types), we further split the group. Otherwise, the group is not split.

Figure 9:
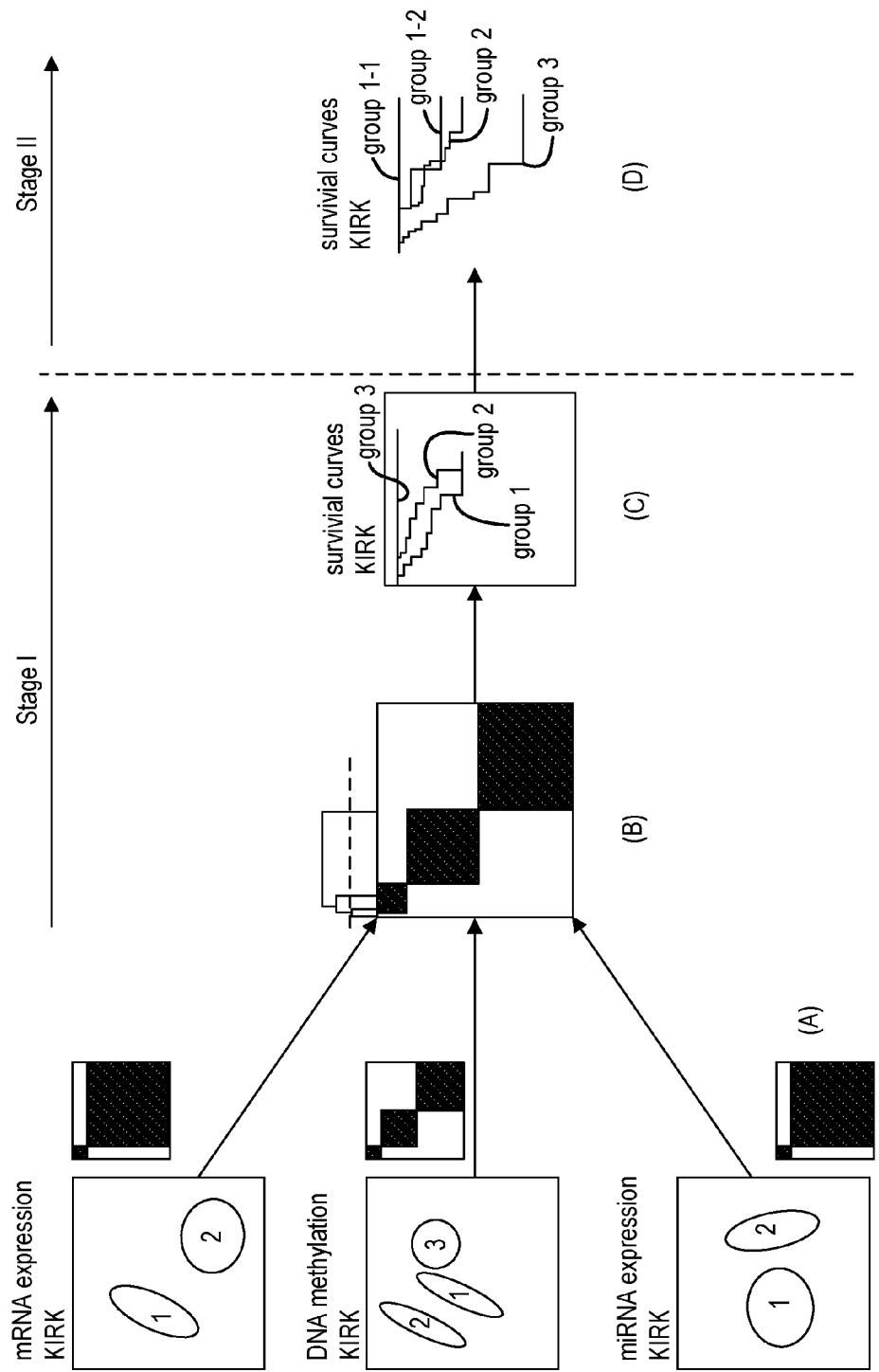
FIG. 9 is a data flow diagram illustrating data integration and disease subtyping for a kidney renal clear cell carcinoma (KIRC)

FIG. 9 displays the subtyping of where the workflow goes through both stages. In stage I, we first cluster each data type independently and then build the corresponding connectivity matrices (panel 9A). We then compute the combined similarity matrix, which is the average connectivity across all the data types. For this dataset, the data types have strong connectivity (>50% agreement) and thus we use the strong similarity matrix to determine the final partitioning (panel 9B). We perform a hierarchical clustering on the strong connectivity matrix. The structure of the data is well defined, so using any linkage would return the same tree. As customary, the tree is cut where the height is the most different (dashed line in panel 9B) yielding 3 groups.

The Kaplan-Meier survival curves for these groups are shown in FIG. 9C. In stage II we check if the discovered groups can be further split into subgroups. Group 1 has more than ⅓ of total samples and thus can be considered for further splitting. The connectivity matrices of samples belonging to group 1 also have strong agreement (>50% agreement). Therefore, this group is further split into 2 subgroups. Group 2 also has more than ⅓ of total samples, but the connectivity matrices do not have strong agreement and thus this group is not split further.

The survival curves of the final partitioning is displayed in FIG. 9D. We note that although the subtype discovery was done on molecular data alone, with no use of clinical information, the 4 groups identified have significantly different clinical profiles: groups 1-1 contains short-term survival women, group 1-2 contains longer survival women, group 2 contains only men, and group 3 survival (all patients that were still alive at the end of the study). The survival analysis indicates that these groups have very significantly different survival profiles (Cox p—value $1.3 \times 10^{-4}$)

Remarkably, the significantly different groups can be obtained only when the 3 types of data are integrated and analyzed together. PINS cannot find subgroups with significantly different survival for any one of the single data types: mRNA, methylation, and miRNA (more details in Table IV in section III-B). However, when all types of data are integrated by our approach, the p-value of the obtained subtypes becomes 4 orders of magnitude more significant.

Figure 31A:
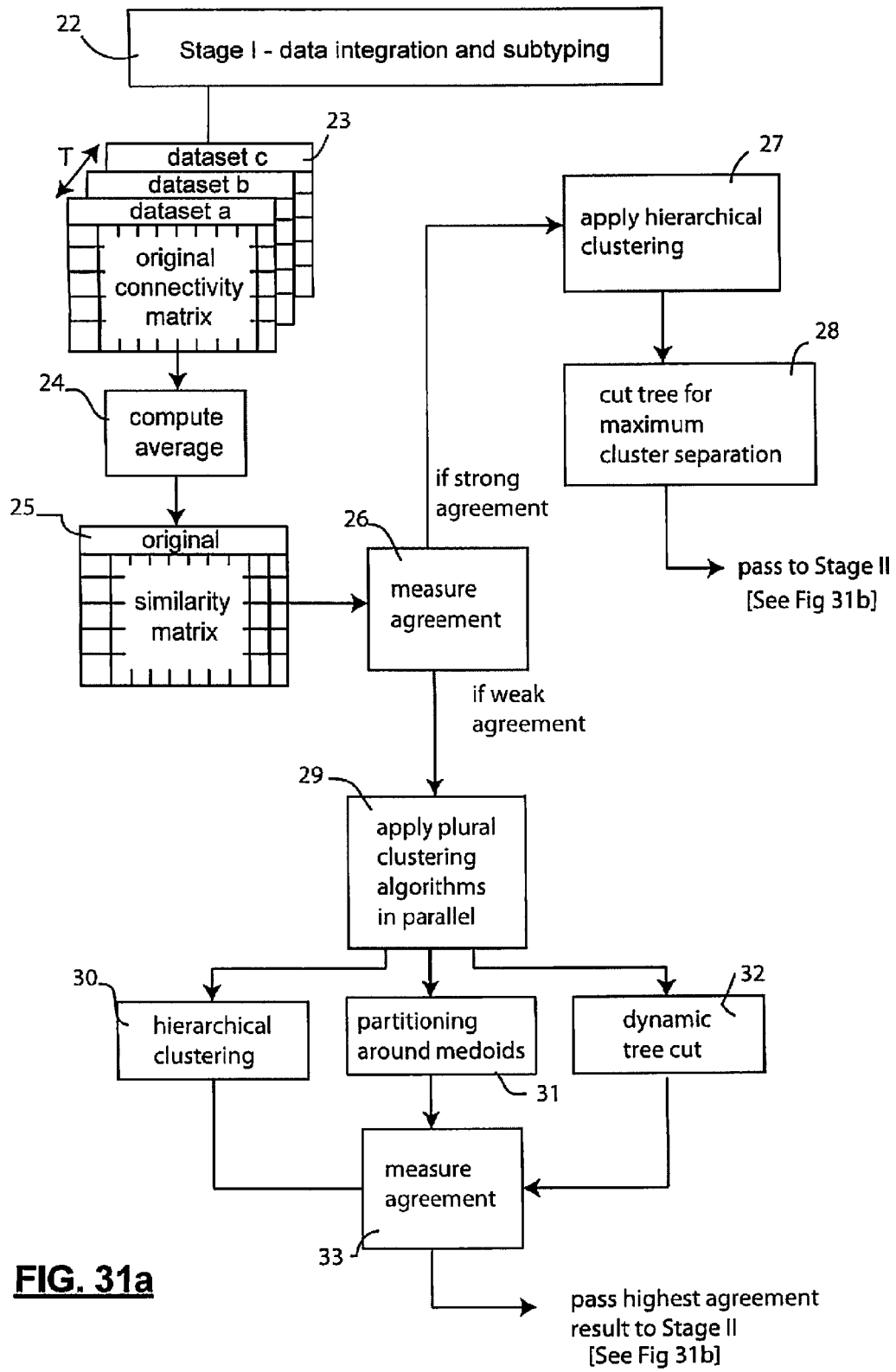
FIGS. 31a and 31b are simplified flow diagrams depicting the major steps of the disclosed technique for subtyping multi-omics data.
Figure 31B:
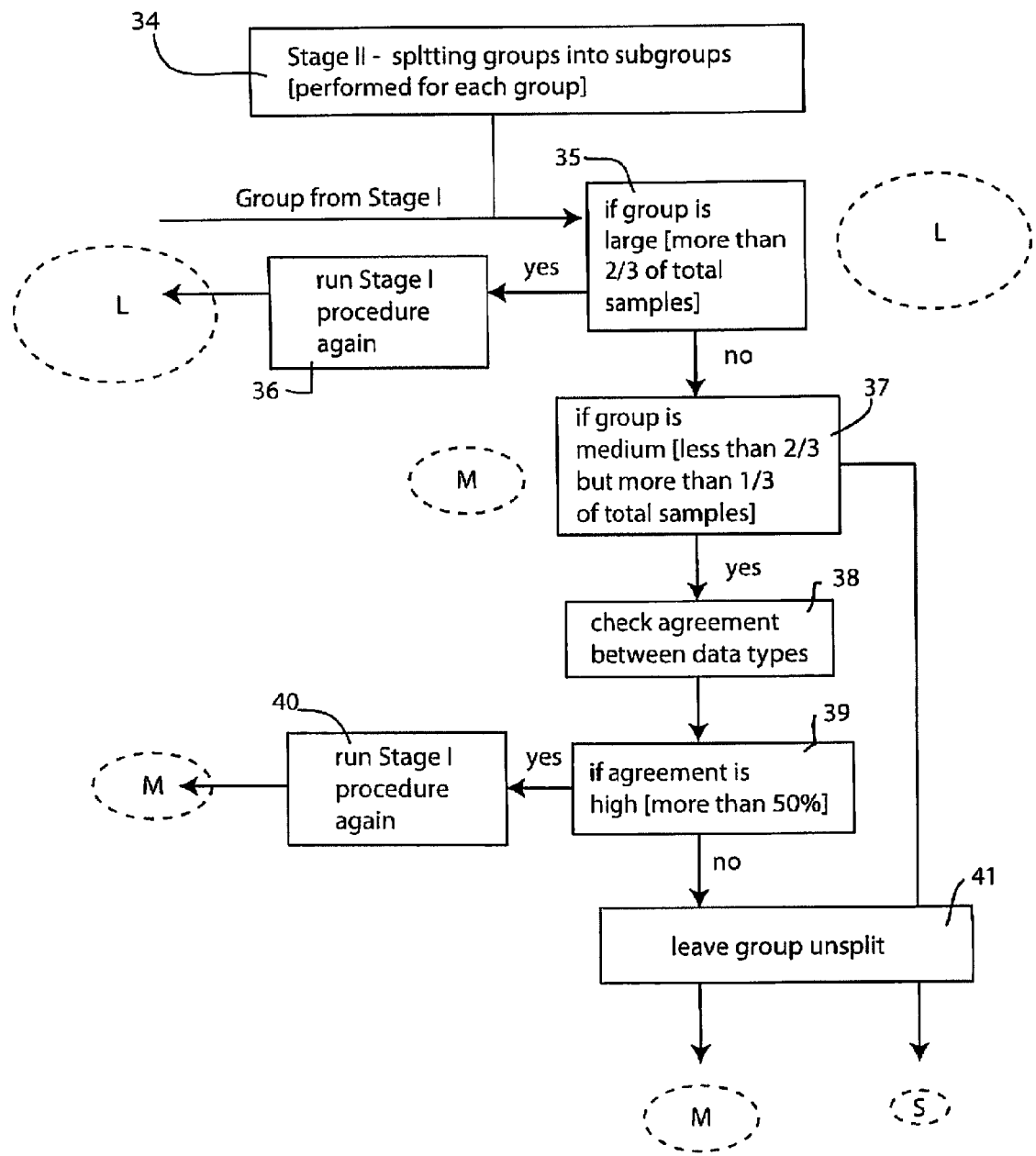

The above-described computer-implemented algorithm for subtyping multi-omics data will now be summarized with reference to FIGS. 31a and 31b. FIG. 31a depicts the Stage I procedure detailed above; FIG. 31b depicts the Stage II procedure detailed above. Referring first to FIG. 31a, the Stage I procedure begins as 22. The original connectivity matrix 23, comprising original connectivity matrices for each of the plural data types, are averaged as at 24 using Equation (9) detailed above. This produces the original similarity matrix 25. The State I algorithm examines this original similarity matrix to determine if there is strong agreement among the plural data types. While any numeric measure of strong agreement can be used, the preferred embodiment determines agreement to be strong if there is agreement among more than 50% among the data types. If the data shows strong agreement, a hierarchical clustering algorithm is applied to the data as at 27. This produces a hierarchical cluster "tree" which is then cut as at 28 for maximum separation. The result of such clustering is then passed on to Stage II.

If at step 26 there is not strong agreement, the algorithm applies plural different clustering algorithms, as indicated diagrammatically at 29. These plural algorithms are effectively run in parallel. While a number of different clustering algorithms may be utilized, for purposes of explaining the technique, FIG. 31a illustrates three clustering algorithms: hierarchical clustering 30, partitioning around medoids 31 and dynamic tree cut 32. The results of each of these plural clustering algorithms are individually examined at 33, to measure the degree of agreement between each clustering partition and the data types. Agreement is assessed essentially the same as in step 26, using Equation (10) detailed above. The output of the clustering algorithm that produces the highest agreement is selected to be passed on to Stage II.

Referring now to FIG. 31b, the Stage II algorithm begins at 34. The algorithm is performed for each cluster group passed to it from Stage I. Thus each group is examined for size. If the size is deemed large as at 35, it is sent back to Stage I at step 36 to be subdivided. While any suitable size metric can be used, the current embodiment considers a group to be large if it contains more than two-thirds of the total samples. A group is considered to be of medium size if it contains more than one-third of the total samples, but less than two-thirds thereof.

If the group is deemed to be of medium size, at step 37, some additional processing is performed. However, if the group is already below the medium size (e.g., less than one-third of the total samples, it will be retained as-is, without requiring further subdividing, as indicated at 41. However if the group is of medium size, the algorithm checks at step 38 to check agreement among data types. If agreement among data types is high (e.g., greater than 50% agreement), as detected at 39, the group is eligible to be further subdivided. Thus at step 40, the group is sent back to be further subdivided. On the other hand, if agreement among data types is not high the group is left un-split as at 41.

III. EXPERIMENTAL STUDIES

Our experimental studies include a wide range of cancers using a single data type as well as using multi-omics data. To evaluate the perturbation clustering (stage I) using a single data type, we download 8 gene expression datasets with known classes (subtypes) from Gene Expression Omnibus and Broad Institute websites. The performance of each clustering method is assessed by comparing their partitionings against the true classes of each dataset. To evaluate the data integration (stage II) of multi-omics data, we download mRNA, methylation, and miRNA data of 6 different cancers from The Cancer Genome Atlas (TCGA) website. The performance of the clustering methods are assessed by comparing the survival of the patients.

A. Experimental Studies Using Gene Expression Data

In this section we assess the performance of PINS in clustering a single data type (stage I). Details of the 8 gene expression datasets are described in Table I. The 5 datasets GSE10245, GSE19188, GSE43580, GSE15061, and GSE14924 were downloaded from Gene Expression Omnibus (http://www.ncbi.nlm.nih.gov/geo/). The 3 datasets Lung2001 (http://www.broadinstitute.org/mpr/lung/), AML2004 (http://www.broadinstitute.org/cancer/pub/nmf), and Brain2002 (http://www.broadinstitute.org/MPR/CNS/) were downloaded from the corresponding websites of Broad Institute.

TABLE I

Description of 8 Gene Expression Datasets Used in Experimental Studies

| Datasets | Class Number | Sample Number | Component Number | Chip Type | Sample Description |
|---|---|---|---|---|---|
| GSE10245 | 2 | 58 | 19851 | hgu133plus2 | 40 adenocarcinomas and 18 squamous cell carcinomas |
| GSE19188 | 3 | 91 | 19851 | hgu133plus2 | 45 adenocarcinomas, 19 large cell carcinomas, and 27 squamous cell carcinomas |
| GSE43580 | 2 | 150 | 19851 | hgu133plus2 | 77 adenocarcinomas and 73 squamous cell carcinomas |
| GSE14924 | 2 | 20 | 19851 | hgu133plus2 | 10 acute myeloid leukemia CD4 T cell and 10 CD8 T cell |
| AML2004 | 3 | 38 | 5000 | hgu6800 | 11 acute myeloid leukemia, 19 acute lymphoblastic leukemia B cell, and 8 T cell |
| GSE15061 | 2 | 366 | 19851 | hgu133plus2 | 202 acute myeloid leukemia samples and 164 myelodyplastic syndrome samples |
| Lung2001 | 4 | 237 | 8641 | hgu95a | 190 adenocarcinomas, 21 squamous cell carcinomas, 20 carcinoid, and 6 small-cell lung carcinomas |
| Brain2002 | 5 | 42 | 5299 | hgu6800 | 10 medulloblastomas, 10 malignant gliolas, 10 atypical teratoid/rhaboid tumors, 4 normal cerebellums, and 8 primitive neuroectodermal tumors |

We compare the performance of PINS with the performance of the other 2 state-of-the-art clustering algorithms, Consensus Clustering (CC), and Similarity Network Fusion (SNF). The range of the number of clusters k is set to [2 . . . 10] for all 3 clustering algorithms. A suitable computer implementation of Consensus Clustering is found in the R statistical software package (ConsensusClusterPlus version 1.18.0). The code for CC is run according to get the change in area under the curve $\Delta(k)$ when the number of clusters k increases. We choose the number of clusters k where the CDF levels off and the corresponding $\Delta(\hat{k})$ gets close to zero, according to the classical CC manuscript.

Regarding Similarity Network Fusion (SNF), although SNF focuses on the data integration, it also provides an option to cluster a single data type. The R package of SNFtool version 2.1 were downloaded from Bioconductor website. The code is run according to the description of the software. We calculate the number of clusters for SNF using the function estimateNumberOfClustersGivenGraph with the range set to [2 . . . 10]. This function returns 4 possible choices. We use the first one as the number of clusters in this study.

For all the 8 gene expression datasets, we know the true labels (subtypes) of each sample. Therefore, we use Rand Index (RI) and adjusted Rand Index (ARI) as the metrics to assess the agreement between the clustering and the ground truth (true classes of the elements). Briefly, Rand Index of 2 partitionings the number of pairs that agree divided by the total number of pairs. In short, $$RI = \frac{a+b}{\binom{N}{2}}$$

where a is the number of pairs that are clustered together in both partitionings, b is the number of pairs that are separated in both partitionings, and $$\binom{N}{2}$$

is the total possible pairs from N elements. The adjusted Rand index (ARI) is the corrected-for-chance version of the Rand index (Appendix A). The clustering results are calculated using all genes without filtering. However, for illustration purpose, the clustering results will be displayed only in the first 2 principal components.

Figure 10A:
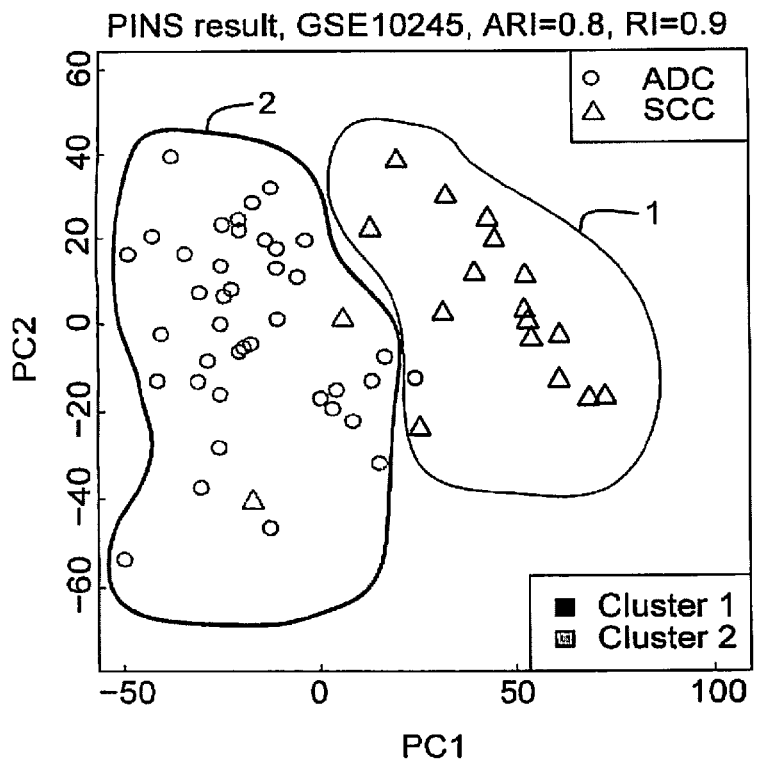
FIGS. 10A-10C (collectively referred to as FIG. 10) are cluster diagrams for dataset GSE10245, comparing the presently disclosed PINS technique (FIG. 10A) with the SNF technique (FIG. 10B) and the CC technique (FIG. 9C)
Figure 10B:
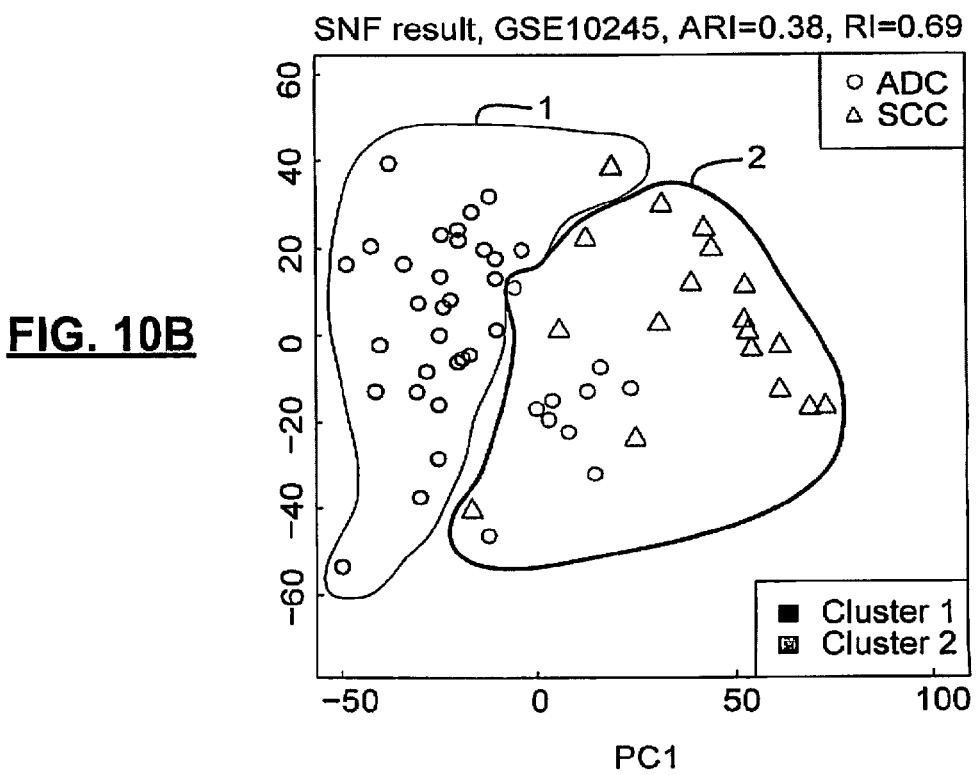
Figure 10C:
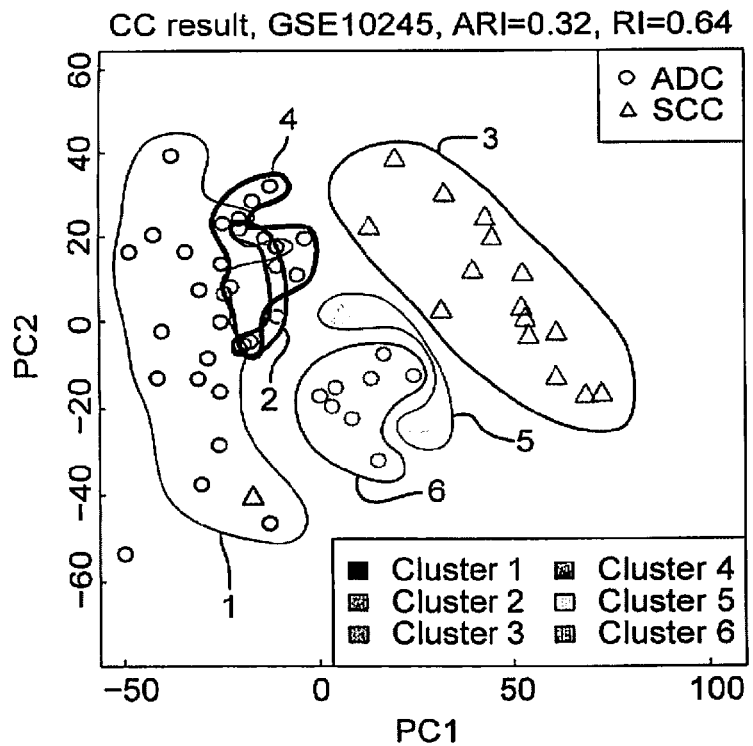

FIG. 10 displays the clustering results of the dataset GSE10245. The dataset consists of 58 non-small cell lung cancer samples of 2 classes: 40 adenocarcinomas (ADC), and 18 squamous cell carcinomas (SCC). From left to right are the results of PINS, Similarity Network Fusion (SNF), and Consensus Clustering (CC) in the first 2 principal components. Different shapes of the points represent different classes while different colors represent different clusters in the results. Visually, the classes are separable with an exception of only some samples. Using perturbing the data, PINS recognizes that the clustering is the most stable with $\hat{k}=2$ and then correctly separate most of the samples. Using eigen-gaps, SNF correctly identifies the number of classes but misclassifies many ADC samples. Using sub-sampling, CC identifies the stability at $\hat{k}=6$ and then splits the 2 classes to smaller groups of samples. In summary, PINS achieves the best performance among the clustering methods (with ARI 0.08 compared to 0.38 and 0.32 of SNF and CC)

Figure 11A:
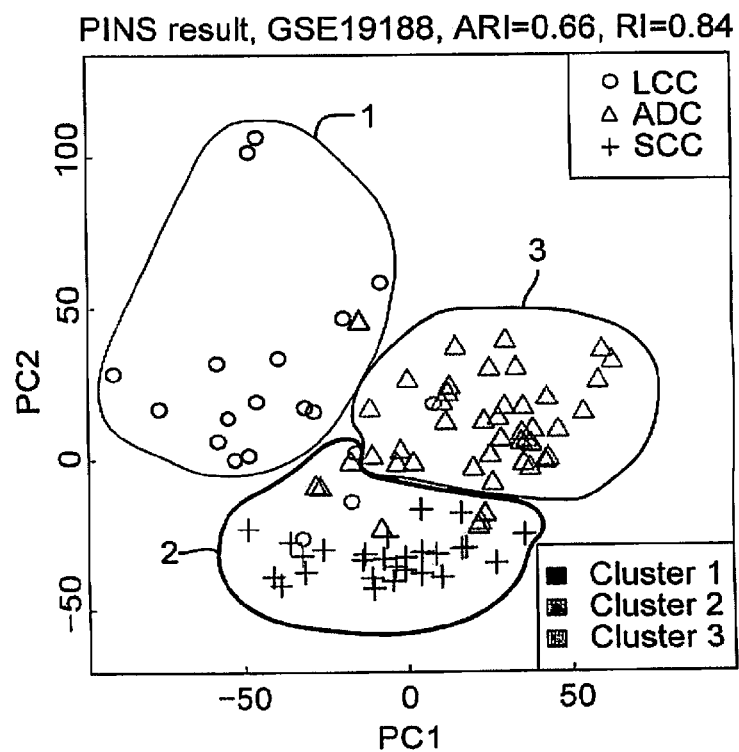
FIGS. 11A-11C (collectively referred to as FIG. 11) are cluster diagrams for dataset GSE19188, comparing the presently disclosed PINS technique (FIG. 11A) with the SNF technique (FIG. 11B) and the CC technique (FIG. 11C)
Figure 11B:
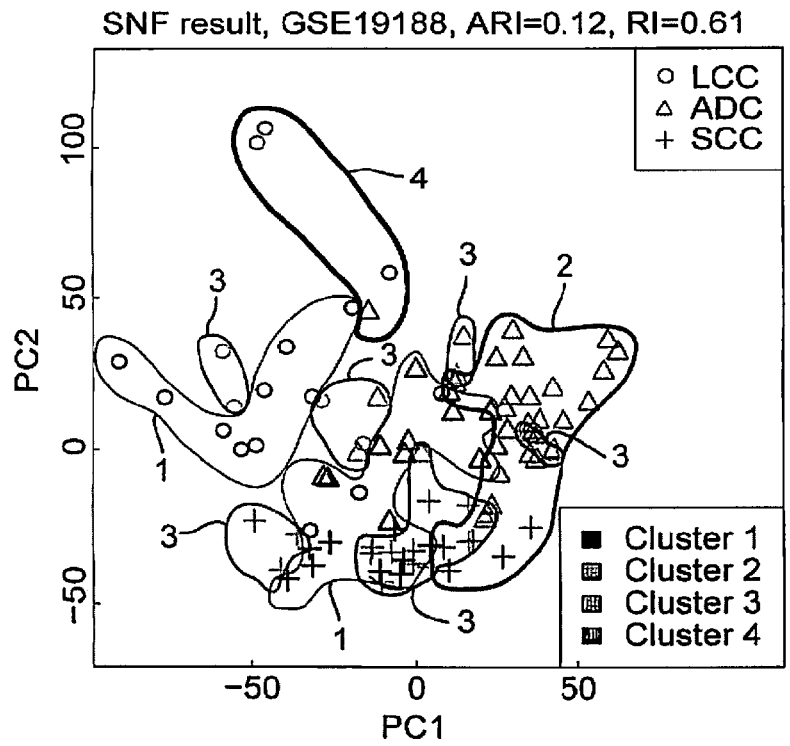
Figure 11C:
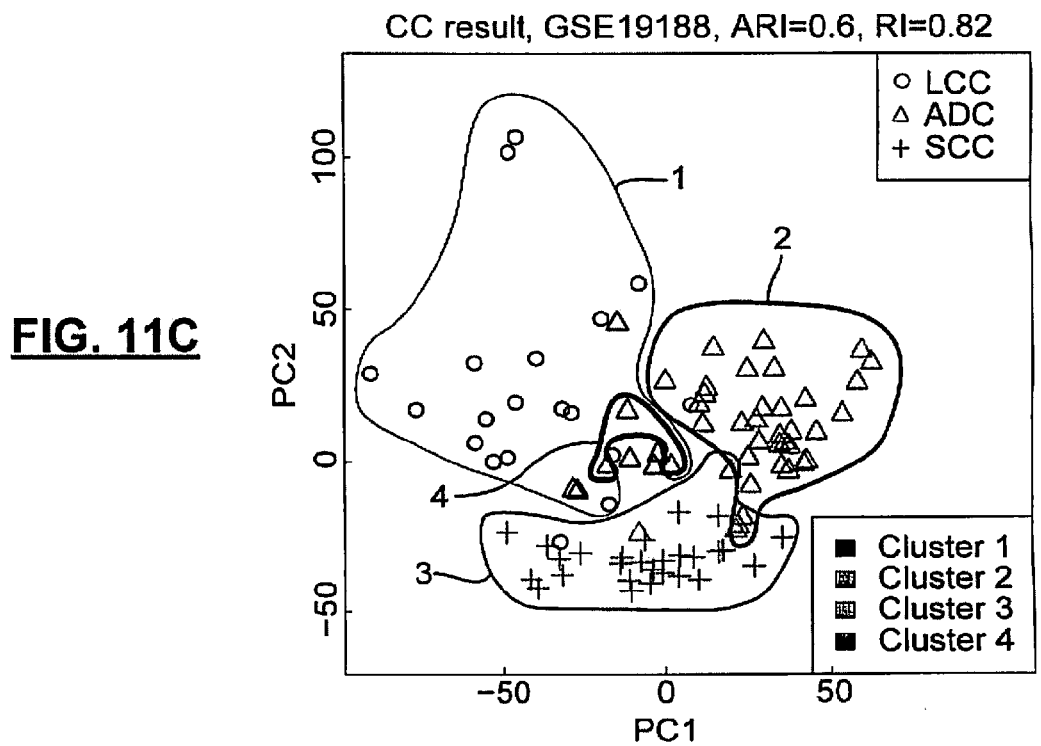

FIG. 11 displays the clustering results of the dataset GSE19188. The dataset consists of 91 non-small cell lung cancer samples of 3 classes: 45 adenocarcinomas (ADC), 19 large cell carcinomas (LCC), and 27 squamous cell carcinomas (SCC). From left to right are the results of PINS, SNF, and CC in the first 2 principal components. Different shapes of the points represent different classes while different colors represent different clusters in the results. PINS correctly recognizes that the clustering is the most stable against data perturbation when ($\hat{k}=3$). Both SNF and CC divides the samples into 4 clusters but CC has a much higher ARI than SNF. In overall, PINS has the highest adjusted Rand index (ARI), which is 0.66 compared to 0.12 and 0.6 of SNF and CC.

Figure 12A:
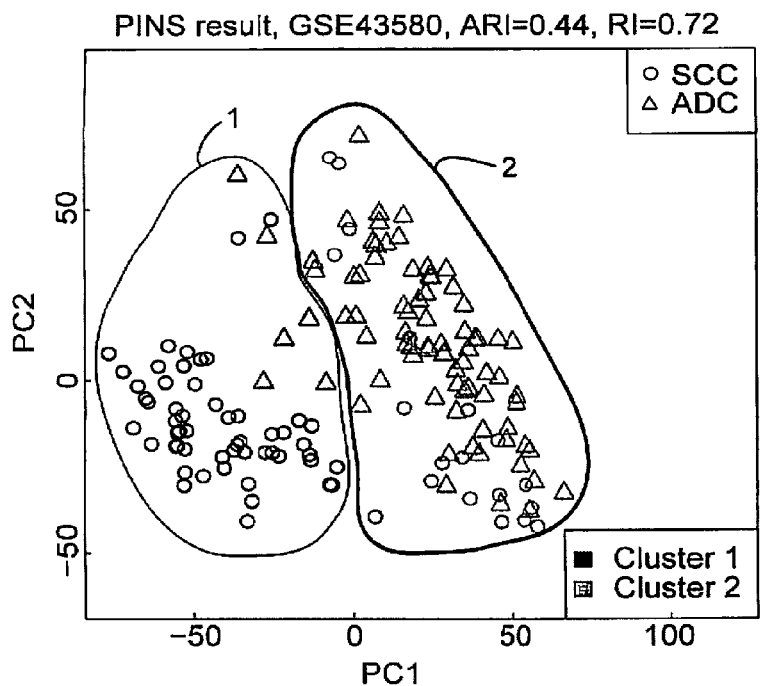
FIGS. 12A-12C (collectively referred to as FIG. 12) are cluster diagrams for dataset GSE43580, comparing the presently disclosed PINS technique (FIG. 12A) with the SNF technique (FIG. 12B) and the CC technique (FIG. 12C)
Figure 12B:
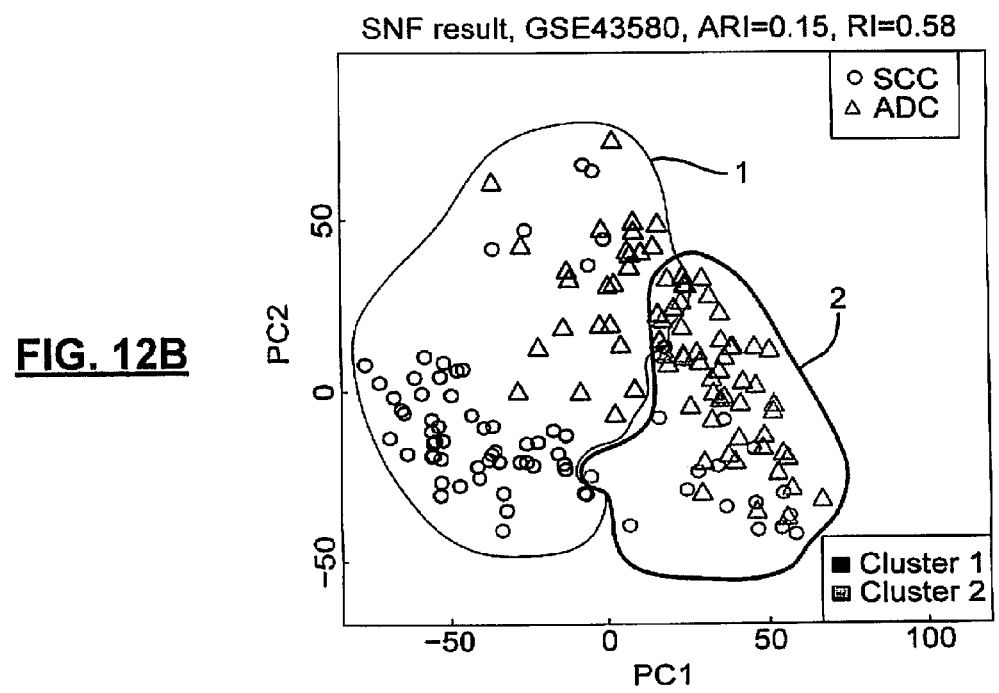
Figure 12C:
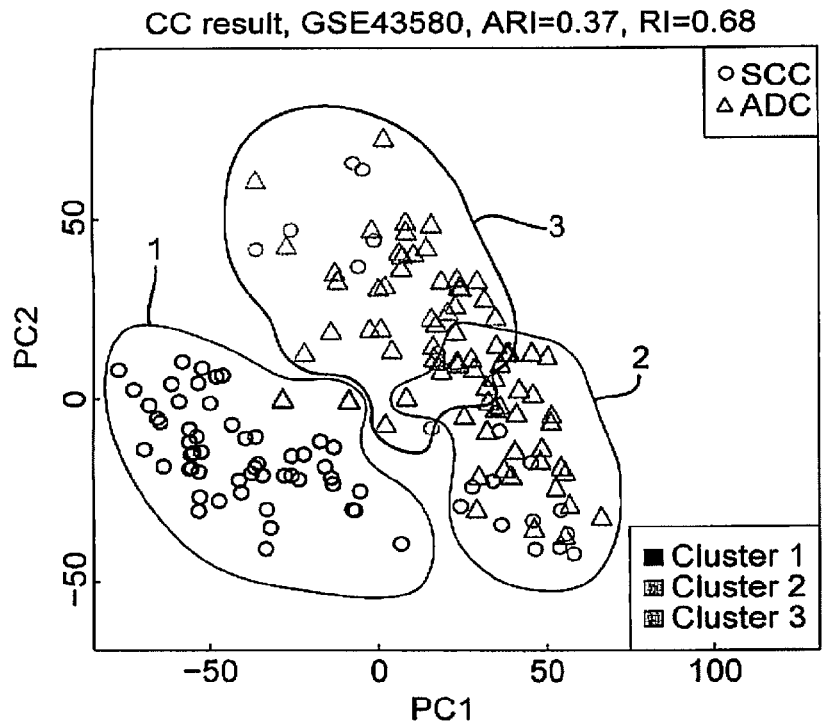

FIG. 12 displays the clustering results of the dataset GSE43580. The dataset consists of 150 non-small cell lung cancer samples: 77 adenocarcinomas (ADC) and 73 squamous cell carcinomas (SCC). From left to right are the results of PINS, SNF, and CC in the first 2 principal components. Different shapes of the points represent different classes while different colors represent different clusters in the results. Both PINS and SNF correctly identify the number of classes while CC divides the samples into 3 clusters. Due to the complex nature of the data, all 3 clustering methods fail to separate the samples of different classes, resulted in low ARI. In overall, PINS has the highest adjusted Rand index (ARI), which is 0.44 compared to 0.15 and 0.37 of SNF and CC.

Figure 13A:
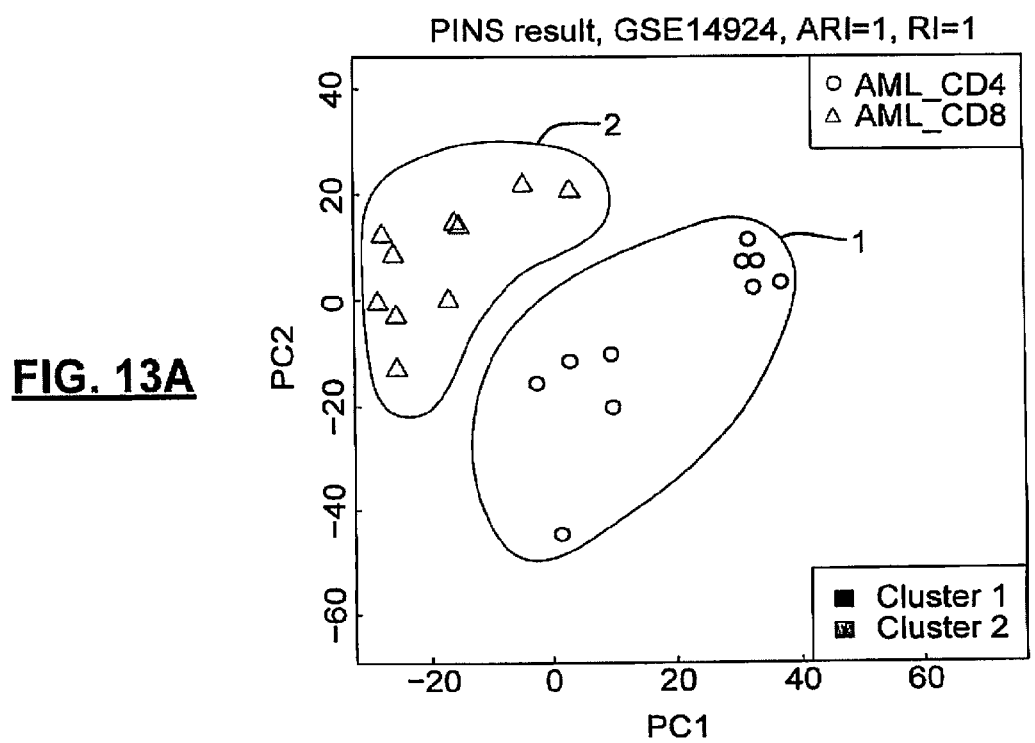
FIGS. 13A-13C (collectively referred to as FIG. 13) are cluster diagrams for dataset GSE14924, comparing the presently disclosed PINS technique (FIG. 13A) with the SNF technique (FIG. 13B) and the CC technique (FIG. 13C)
Figure 13B:
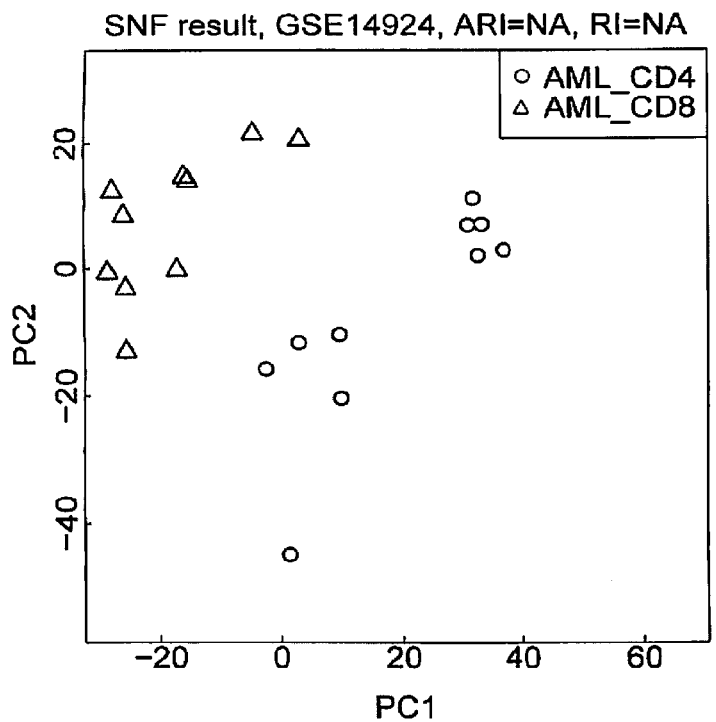
Figure 13C:
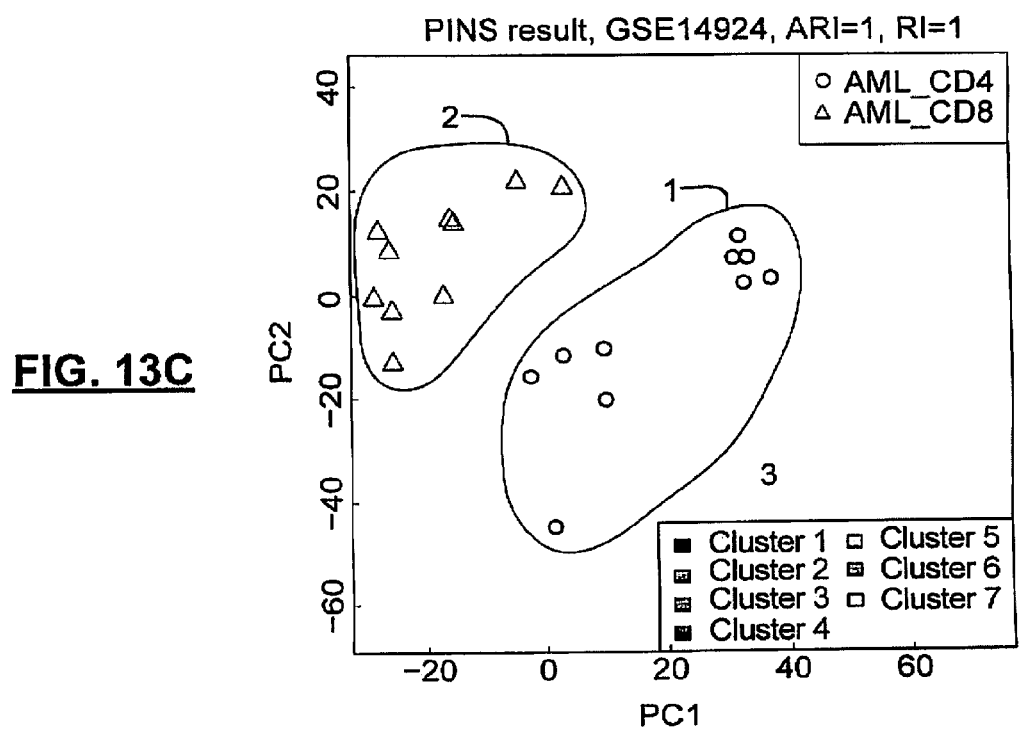

FIG. 13 displays the clustering results of the dataset GSE14924. The dataset consists of 2 classes: 10 acute myeloid leukemia CD4 T cells and 4 CD8 T cells. From left to right are the results of PINS, SNF, and CC in the first 2 principal components. Different shapes of the points represent different classes while different colors represent different clusters in the results. PINS correctly identifies the number of classes and perfectly separate the samples with ARI=1. SNF returns an error message without any clustering result. CC divides the samples into 7 clusters, which is much higher than the real number of classes.

Figure 14A:
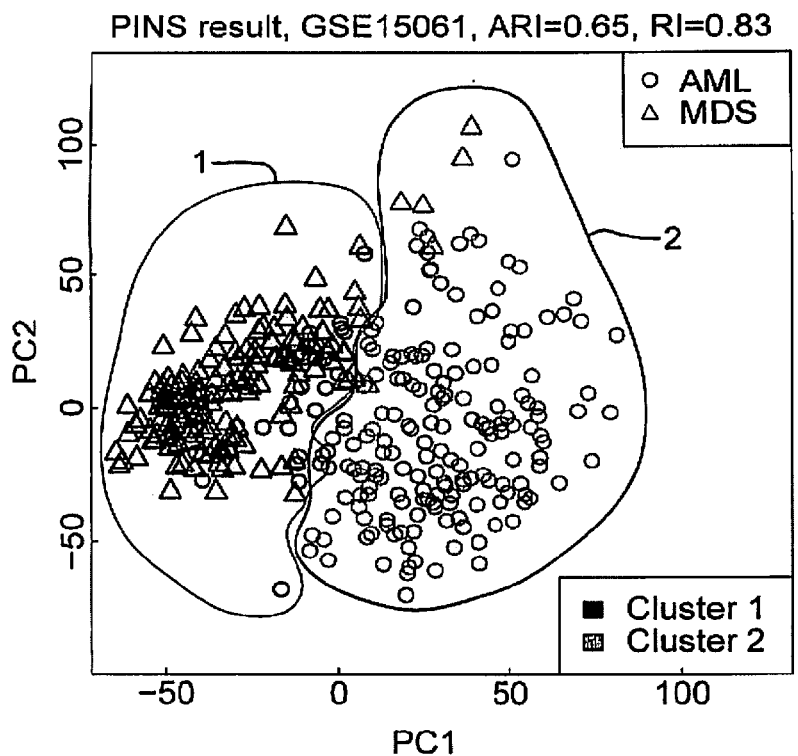
FIGS. 14A-14C (collectively referred to as FIG. 14) are cluster diagrams for dataset GSE15061, comparing the presently disclosed PINS technique (FIG. 14A) with the SNF technique (FIG. 14B) and the CC technique (FIG. 14C)
Figure 14B:
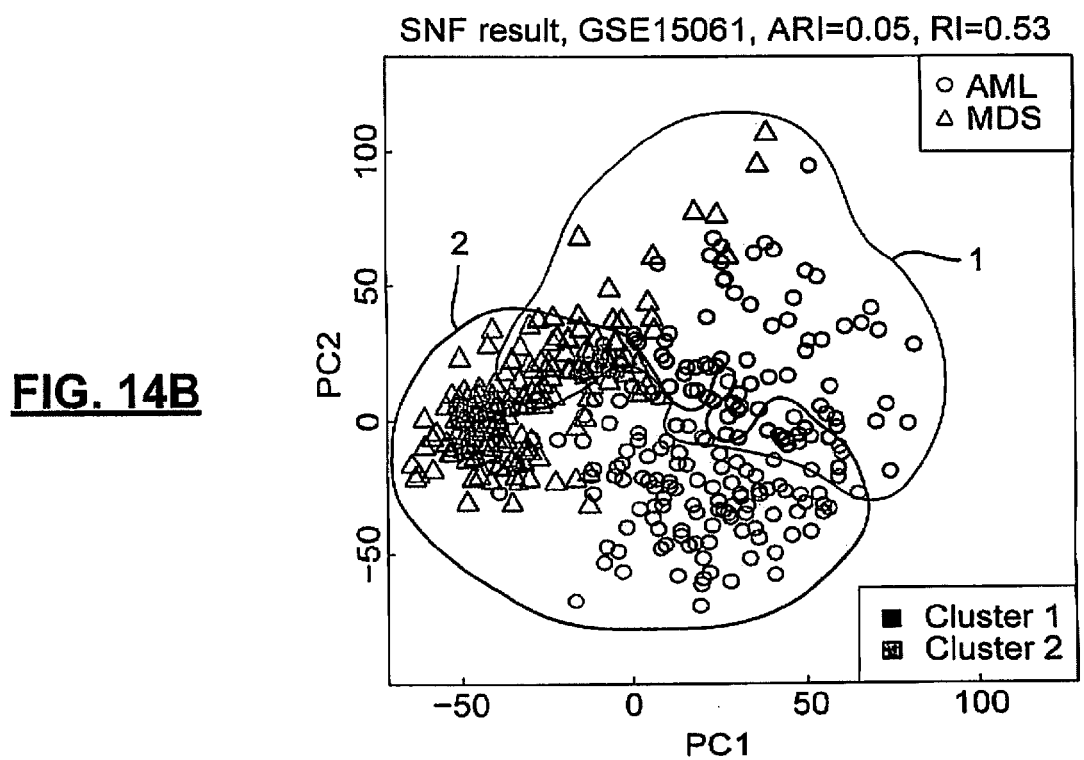
Figure 14C:
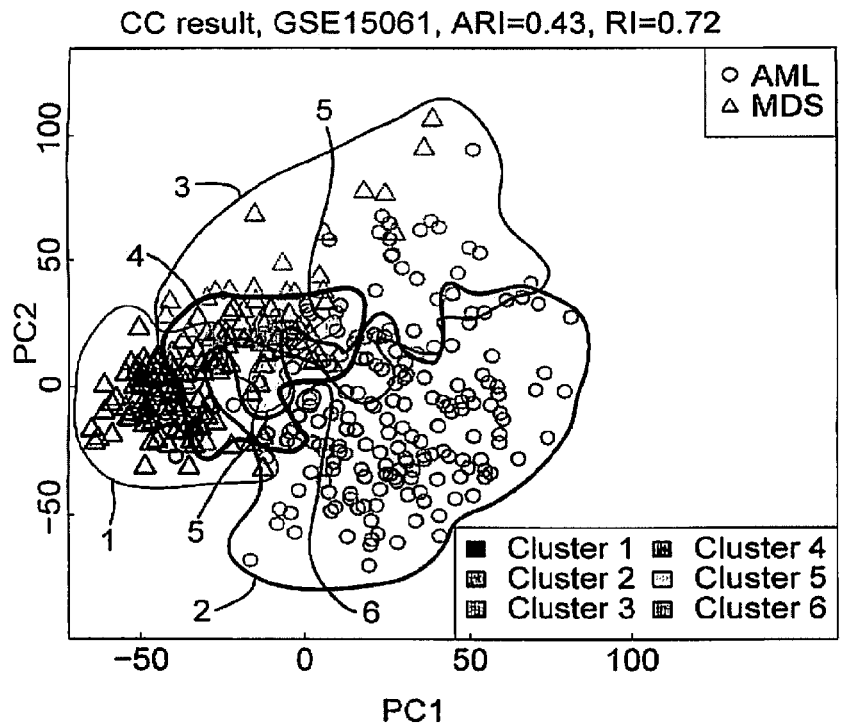

FIG. 14 displays the clustering results of the dataset GSE15061. The dataset consists of 366 leukemia samples of 2 classes: 202 acute myeloid leukemia samples and 164 myelodyplastic syndrome samples. Both PINS and SNF correctly identify the number of classes but PINS has much higher ARI than that of SNF. CC divides the samples into 7 clusters, which is much higher than the true number of classes. PINS has the highest adjusted Rand index (ARI), which is 0.65 compared to 0.05 and 0.43 of SNF and CC.

Figure 15A:
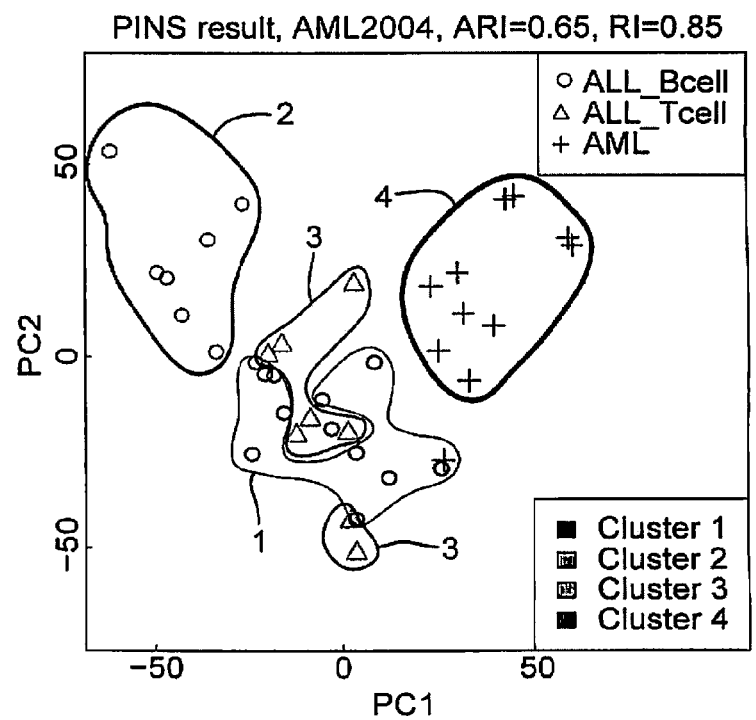
FIGS. 15A-15C (collectively referred to as FIG. 15) are cluster diagrams for dataset AML2004, comparing the presently disclosed PINS technique (FIG. 15A) with the SNF technique (FIG. 15B) and the CC technique (FIG. 15C)
Figure 15B:
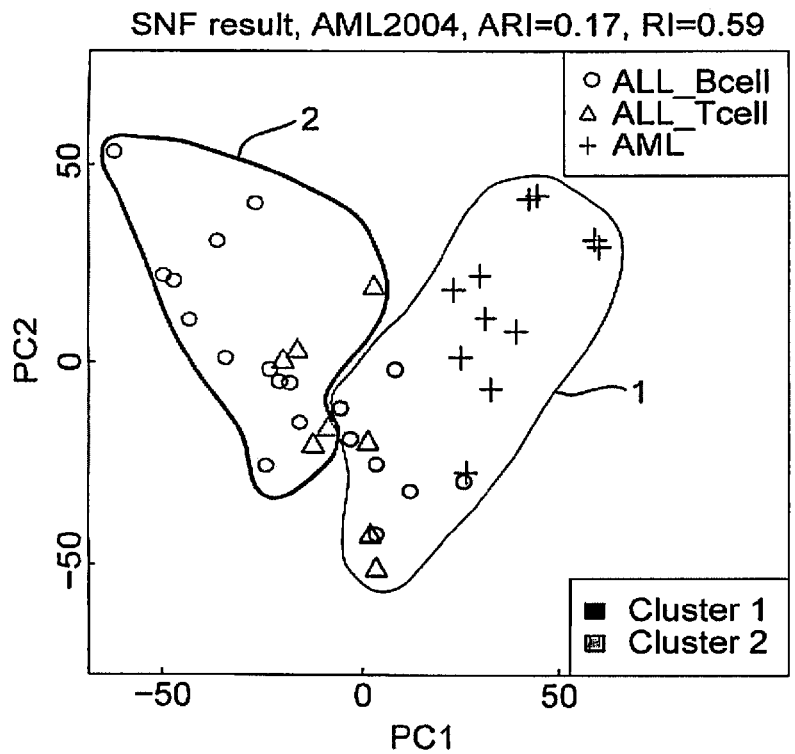
Figure 15C:
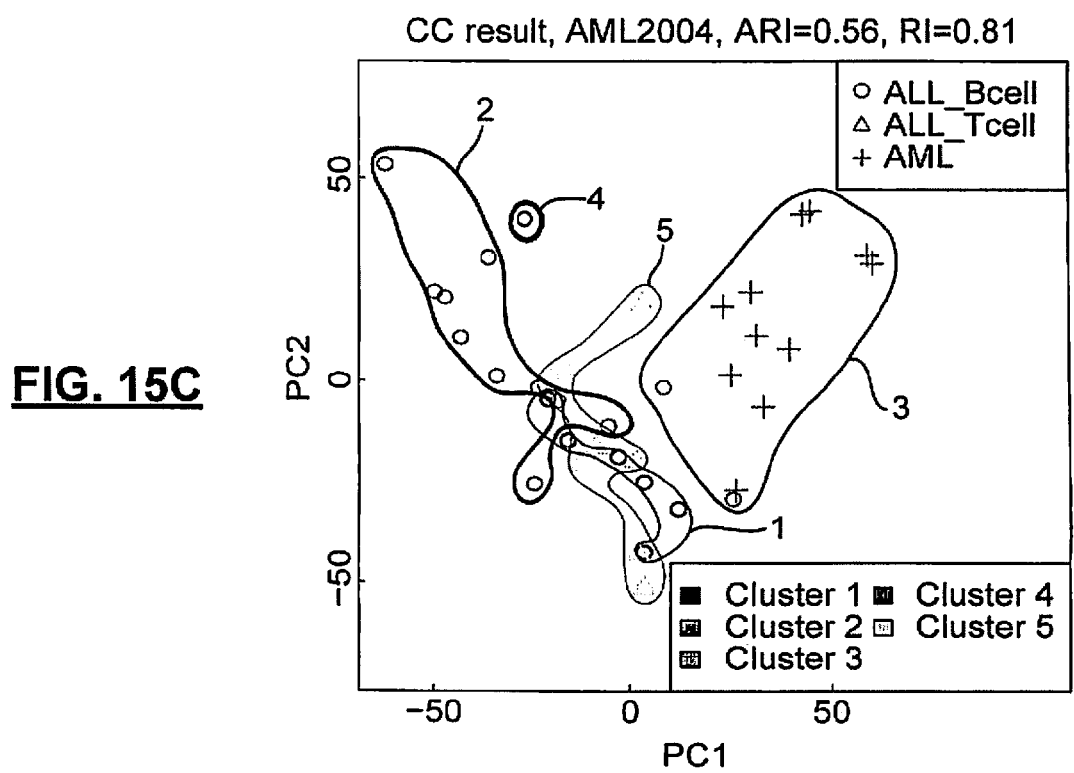

FIG. 15 displays the clustering results of the dataset AML2004. The dataset consists of 38 samples of 3 classes: 11 acute myeloid leukemia (AML), 19 acute lymphoblastic leukemia B cells (ALL_Bcell), and 8 T cells (ALL_Tcell). From left to right are the results of PINS, SNF, and CC in the first 2 principal components. Different shapes of the points represent different classes while different colors represent different clusters in the results. In the first 2 principal components, the AML samples can be separated from the rest with an exception one AML sample that is coordinated very close to ALL_Bcell samples. The samples classes ALL_Tcell and ALL_Bcell stay close to each other and hard to be separated. None of the mentioned methods discovers the number of classes in the this dataset. PINS recognizes that the clustering is the most stable with $\hat{k}=4$. It separates the AML and ALL_Tcell classes accordingly, but also splits the ALL_Tcell class into 2 clusters. SNF divides the dataset into 2 clusters, resulted in the lowest ARI. Similar to PINS, CC separate the AML and ALL_Tcell classes well but also splits the ALL_Bcell into 3 clusters. In overall, PINS has the highest adjusted Rand index (ARI), which is 0.65 compared to 0.17 and 0.56 of SNF and CC.

Figure 16A:
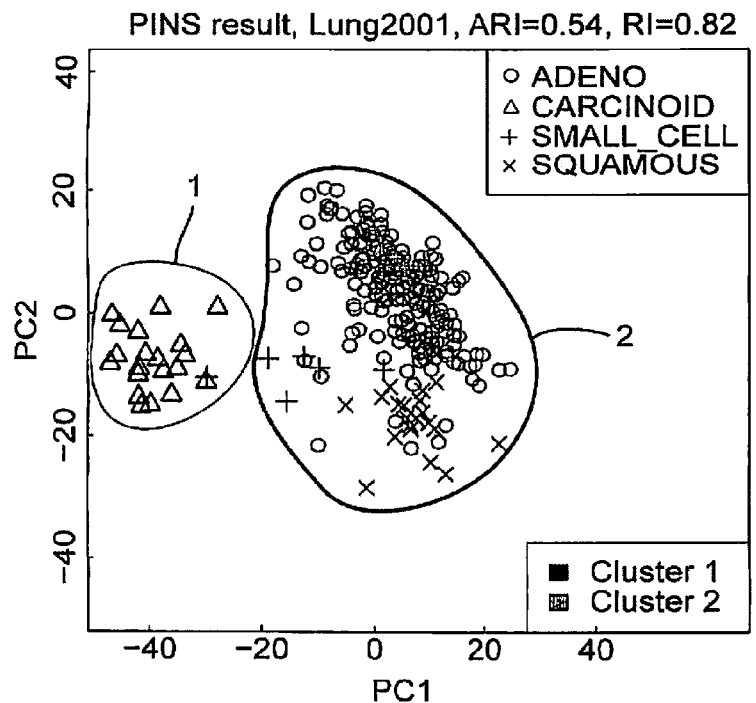
FIGS. 16A-16C (collectively referred to as FIG. 16) are cluster diagrams for dataset Lung2001, comparing the presently disclosed PINS technique (FIG. 16A) with the SNF technique (FIG. 16B) and the CC technique (FIG. 16C)
Figure 16B:
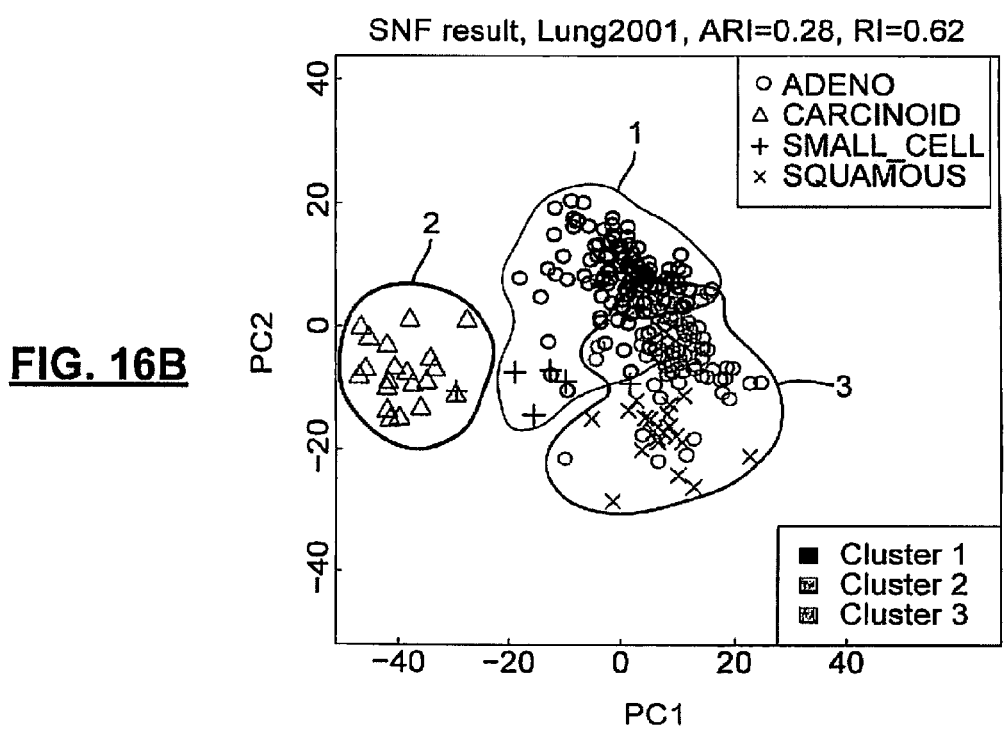
Figure 16C:
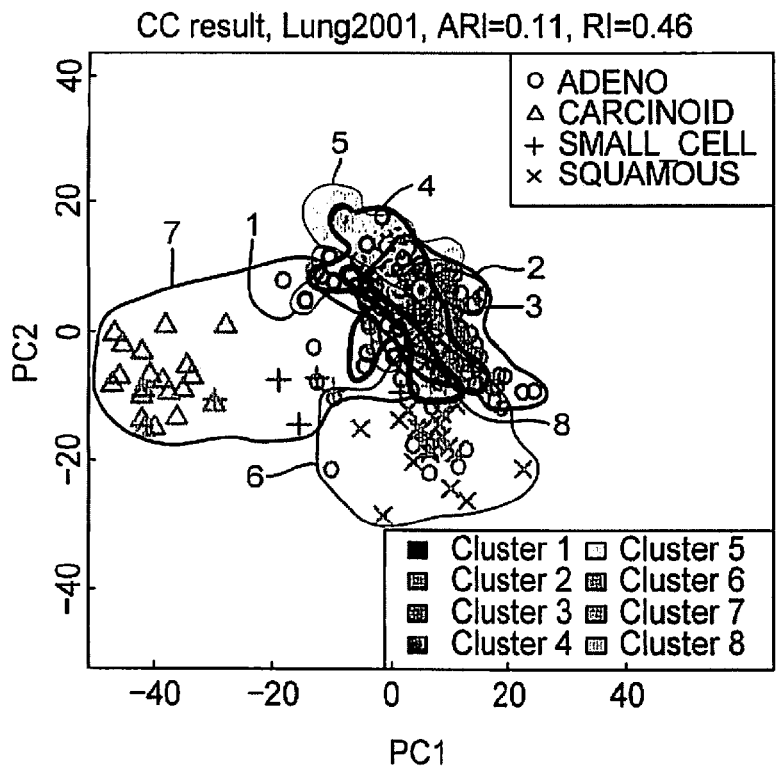

FIG. 16 displays the clustering results of the dataset Lung2001. The dataset consists of 237 samples of 4 classes: 190 adenocarcinomas (ADENO), 21 squamous cell carcinomas (SQUAMOUS), 20 carcinoids (CARCINOID), and 6 small-cell lung carcinomas (SMALL_CELL). From left to right are the results of PINS, SNF, and CC in the first 2 principal components. Different shapes of the points represent different classes while different colors represent different clusters in the results. The CARCINOID class stands out from the rest, but the other 3 are mixed together and hard to separate. PINS recognizes the stability when the partitioning has 2 clusters, one consists of the CARCINOID samples while the another one consists of all other samples. SNF separates the CARCINOID samples and split the rest into 2 clusters. However, each of these 2 clusters consists of a mixture of ADENO, SMALL_CELL, and SQUAMOUS, resulting in a lower ARI. CC splits the samples into 8 clusters, which is much higher than the number of classes. In addition, each of the cluster consists of a mixture of some classes. In overall, PINS has the highest adjusted Rand index (ARI), which is 0.54 compared to 0.28 and 0.11 of SNF and CC.

Figure 17A:
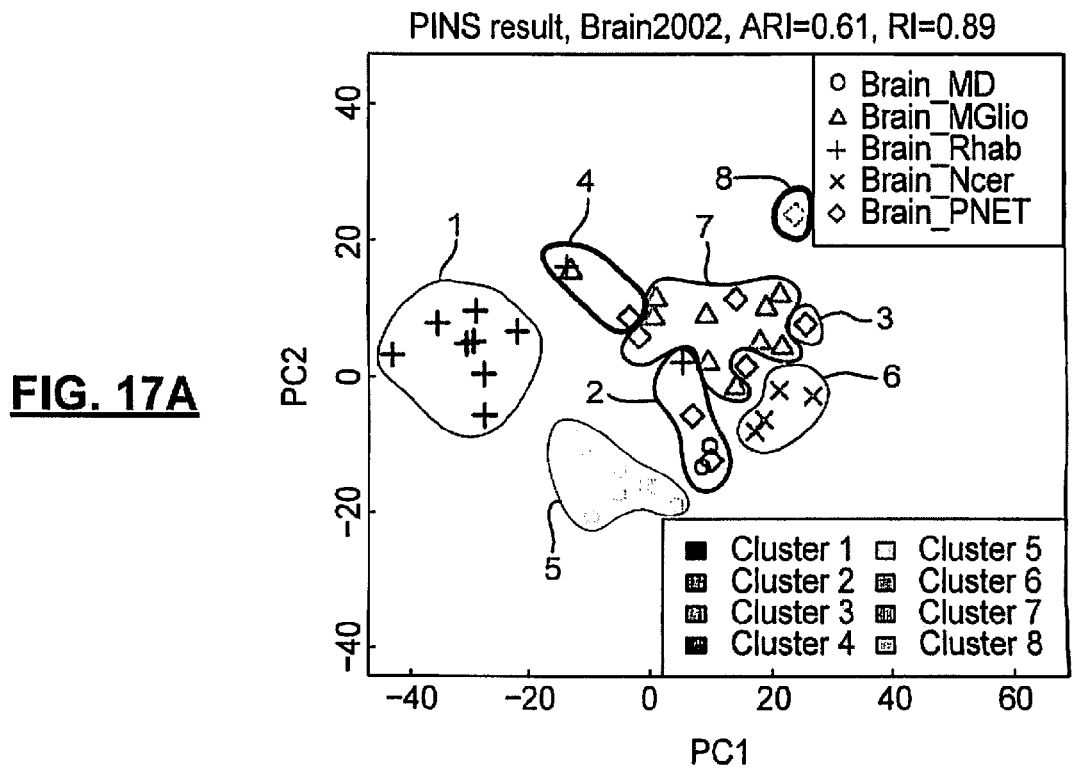
FIGS. 17A-17C (collectively referred to as FIG. 17) are cluster diagrams for dataset Brain2002, comparing the presently disclosed PINS technique (FIG. 17A) with the SNF technique (FIG. 17B) and the CC technique (FIG. 17C)
Figure 17B:
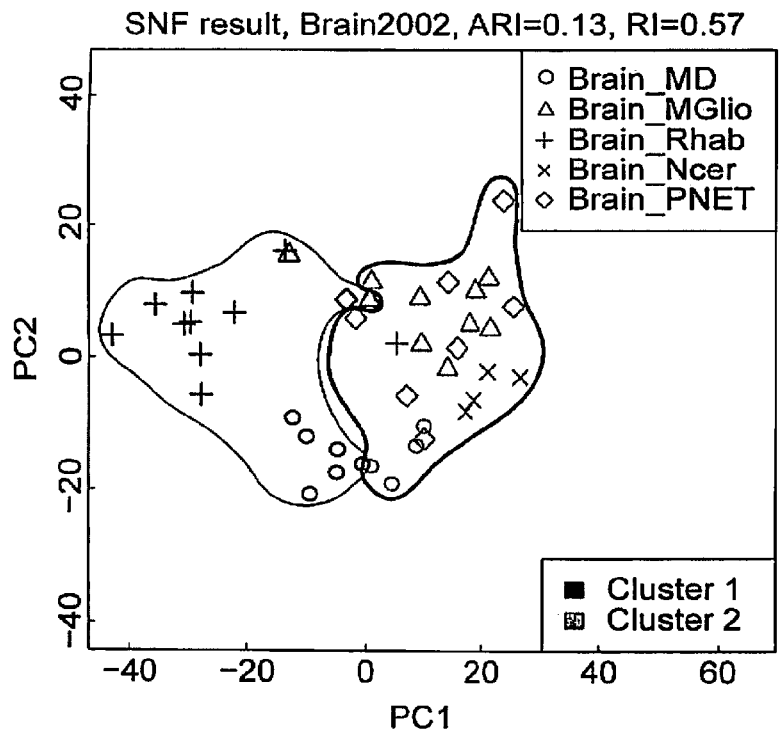
Figure 17C:
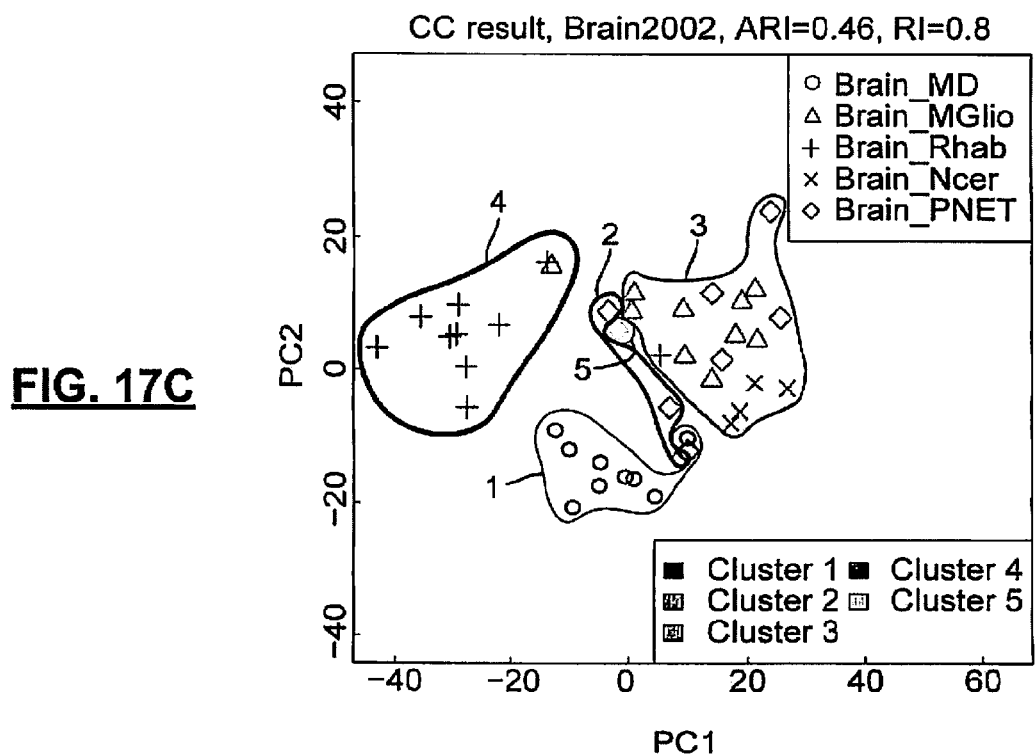

FIG. 17 displays the clustering result for the dataset Brain2002. The dataset consists of 42 samples of 5 classes: 10 medulloblastomas (Brain_MD), 10 malignant gliolas (Brain_Mglio), 10 atypical teratoid/rhaboid tumors (Brain_Rhab), 4 normal cerebellums (Brain_Ncer), and 8 primitive neuroectodermal tumors (Brain PNET). From left to right are the results of PINS, SNF, and CC in the first 2 principal components. Different shapes of the points represent different classes while different colors represent different clusters in the results. PINS recognizes stability with $\hat{k}=8$, which is more than the number of classes. It successfully separates the most of samples from classes Brain_MD, Brain_Rhab, Brain_Ncer, and Brain_Mglio but splits the rest to many clusters. SNF divides all the samples into 2 clusters for each of which is a mixture of many classes. CC discovers the number of classes. It separates the most samples of classes Brain_Rhab and Brain_MD but fail to separate the rest of the samples from the remaining 3 classes. In overall, PINS has the highest adjusted Rand index (ARI), which is 0.61 compared to 0.13 and 0.46 of SNF and CC.

The summary of all results is shown in Table II. The first 3 columns in the table show the names, sample numbers, and true class numbers of the data sets. The next 3 columns show the number of clusters, RI, and ARI for the clustering results of PINS. The last 6 columns show those of CC and SNF. For each dataset (row), cells highlighted in green have the highest RI and ARI. We put NA in the result of SNF for dataset GSE14924 because it returns an error message without a result. For all the 8 datasets, PINS achieves higher clustering performance than SNF and CC.

Since the Consensus Clustering (CC) does not have the functionality to integrate multiple data types, we compare

TABLE II

Performance of PINS, Consensus Clustering (CC), and Similarity Network Fusion (SNF) Using Gene Expression Datasets

| Dataset | | | PINS | | | SNF | | | CC | | |
|---|---|---|---|---|---|---|---|---|---|---|---|
| Name | #Sample | #Class | #Cluster | RI | ARI | #Cluster | RI | ARI | #Cluster | RI | ARI |
| GSE10245 | 58 | 2 | 2 | 0.90 | 0.80 | 2 | 0.67 | 0.33 | 6 | 0.64 | 0.32 |
| GSE19188 | 91 | 3 | 3 | 0.84 | 0.66 | 2 | 0.58 | 0.16 | 4 | 0.82 | 0.60 |
| GSE43580 | 150 | 2 | 2 | 0.72 | 0.44 | 2 | 0.57 | 0.14 | 3 | 0.68 | 0.37 |
| GSE15061 | 366 | 2 | 2 | 0.83 | 0.65 | 2 | 0.54 | 0.08 | 6 | 0.72 | 0.43 |
| GSE14924 | 20 | 2 | 2 | 1.00 | 1.00 | NA | NA | NA | 7 | 0.64 | 0.25 |
| Lung2001 | 237 | 4 | 2 | 0.82 | 0.54 | 3 | 0.62 | 0.28 | 8 | 0.44 | 0.11 |
| AML2004 | 38 | 3 | 4 | 0.85 | 0.66 | 2 | 0.59 | 0.17 | 5 | 0.81 | 0.56 |
| Brain2002 | 42 | 5 | 7 | 0.89 | 0.61 | 2 | 0.57 | 0.13 | 5 | 0.80 | 0.46 |

B. Experimental Studies Using Multi-Omics Data

1) Analysis Across a Wide Spectrum of Cancer:

We downloaded 6 different cancer datasets from The Cancer Genome Atlas (TCGA): glioblastoma multiform (GBM), lung squamous cell carcinoma (LUSC), breast invasive carcinoma (BRCA), acute myeloid leukemia (LAML), kidney renal clear cell carcinoma (KIRC), and colon adenocarcinoma (COAD). For each cancer dataset, we downloaded TCGA-curated level 3 data of mRNA expression, DNA methylation, and mRNA expression. We analyze the set of patients that have measurements across all the 3 data types. TCGA contains different platforms for each data type. We choose the platforms of each data type so that they have the largest set of common patients.

Table III displays details of the data for the 6 cancer datasets. The number of samples is the set of patients that have measurements across all the 3 data types. The number of component for a data type is the number of measurements for a patient for that data type. The expression values of DNA methylation fall between 0 and 1 and the expression values of microarray measurements (gene expression) fall between 2 and 14. We use these data as they are without processing. For sequencing data, since the values are too large (up to millions), we use their log transformation (base 2).

PINS against SNF in this section. Using the clinical data from TCGA, we calculate the Cox log-rank test p-values for the each partitioning. We note that Cox p-values were also used to assess clustering performance for SNF. We report the number of clusters and Cox p-values for each data type as well as for the integrated data in Table IV. The first 3 columns describe the data while the next 4 columns show the number of clusters and Cox p-value for PINS and SNF. The results for the integrated data are displayed in bold. The cells highlighted in green have significant p-values (cutoff 0.05). SNF gives significant p-value for only LAML while PINS gives significant p-values for KIRC, GBM, LUSC, BRCA, and LAML.

For the kidney renal clear cell carcinoma (KIRC) dataset, neither algorithm can find groups with significantly different survival using any single data type. SNF cannot find significant different groups even after data integration. In contrast, when all data types are integrated by PINS, the p-value of the obtained subtypes becomes 4 order of magnitude more significant.

Figure 18A:
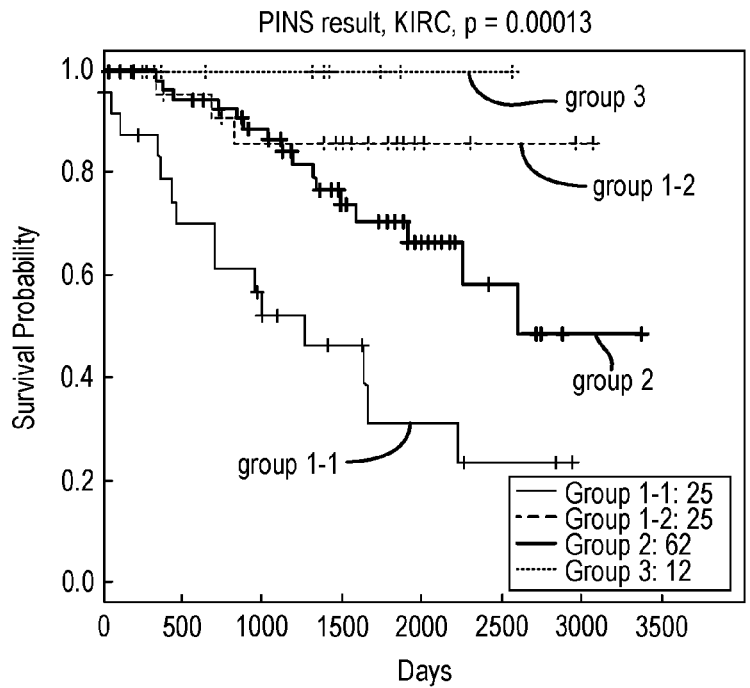
FIG. 18A-18B (collectively referred to as FIG. 18) are Kaplan-Meier survival analysis graphs for kidney renal clear cell carcinoma (KIRC), comparing the presently disclosed PINS technique (FIG. 18A) with the SNF technique (FIG. 18B)
Figure 18B:
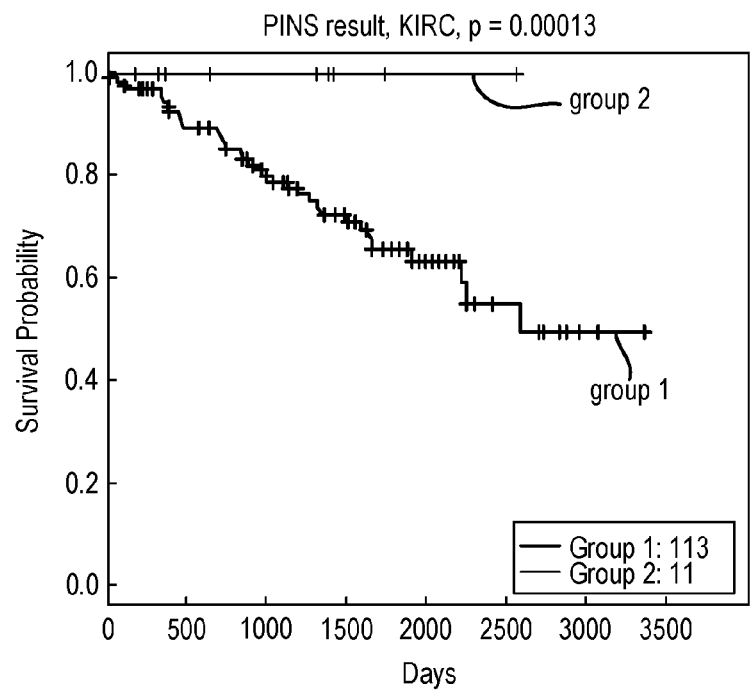

FIG. 18 displays the Kaplan-Meier analysis for KIRC. SNF finds 2 groups with no significantly different survival (p=0.138). In contrast, PINS discovers 4 different groups with very different survival profiles (p=$1.3 \times 10^{-4}$). In phase 1, PINS finds 3 groups of patients: group 1 consists of 50

TABLE III

Description of the 6 Datasets

| Dataset | #Sample | Data Type | #Components | Platform | Data Level |
|---|---|---|---|---|---|
| KIRC | 124 | mRNA | 17974 | Illumina HiSeq RNASeq | 3 |
| | | Methylation | 23165 | HumanMethylation27 | 3 |
| | | miRNA | 590 | Illumina GASeq miRNASeq | 3 |
| GBM | 273 | mRNA | 12042 | HT HG-U133A | 3 |
| | | Methylation | 22833 | HumanMethylation27 | 3 |
| | | miRNA | 534 | Illumina HiSeq miRNASeq | 3 |
| LUSC | 110 | mRNA | 12042 | HT HG-U133A | 3 |
| | | Methylation | 23348 | HumanMethylation27 | 3 |
| | | miRNA | 706 | Illumina GASeq miRNASeq | 3 |
| BRCA | 172 | mRNA | 20100 | Illumina HiSeq RNASeqV2 | 3 |
| | | Methylation | 22533 | HumanMethylation27 | 3 |
| | | miRNA | 718 | Illumina GASeq miRNASeq | 3 |
| LAML | 164 | mRNA | 16818 | Illumina GASeq RNASeq | 3 |
| | | Methylation | 22833 | HumanMethylation27 | 3 |
| | | miRNA | 552 | Illumina GASeq miRNASeq | 3 |
| COAD | 146 | mRNA | 17062 | Illumina GASeq RNASeq | 3 |
| | | Methylation | 24454 | HumanMethylation27 | 3 |
| | | miRNA | 710 | Illumina GASeq miRNASeq | 3 | patients, group 2 consists of 62 patients, and group 3 consists of 12 patients who all survive. In phase 2, only group 1 satisfy the splitting condition and is further divided into groups 1-1 (25 patients) and 1-2 (25 patients) with very different survival. Remarkably, the significantly different groups can be obtained only when the 3 data types of data are integrated and analyzed together. Table IV shows the results obtained by both PINS and SNG on each individual data type, as well as by integrating the data. Neither algorithm can find subgroups with significantly different survival for any one of the single data types: mRNA, methylation, and miRNA. SNF cannot find significant different subtypes even after data integration. However, when all types are integrated by our proposed approach, the p-value of the obtained subtypes becomes 4 orders of magnitude more significant. The clinical and mutation information associated with each group are reported in Experimental Studies section below.

1-2 (68 patients). The clinical and mutation information associated with each group are reported in the Experimental Studies section below.

Figure 20A:
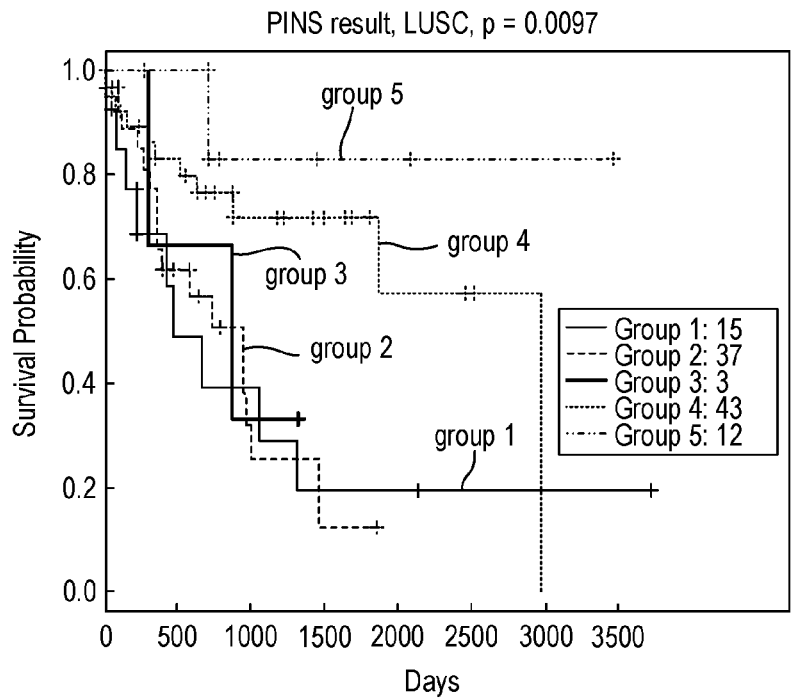
FIG. 20A-20B (collectively referred to as FIG. 20) are Kaplan-Meier survival analysis graphs for lung squamous cell carcinoma (LUSC), comparing the presently disclosed PINS technique (FIG. 20A) with the SNF technique (FIG. 20B)
Figure 20B:
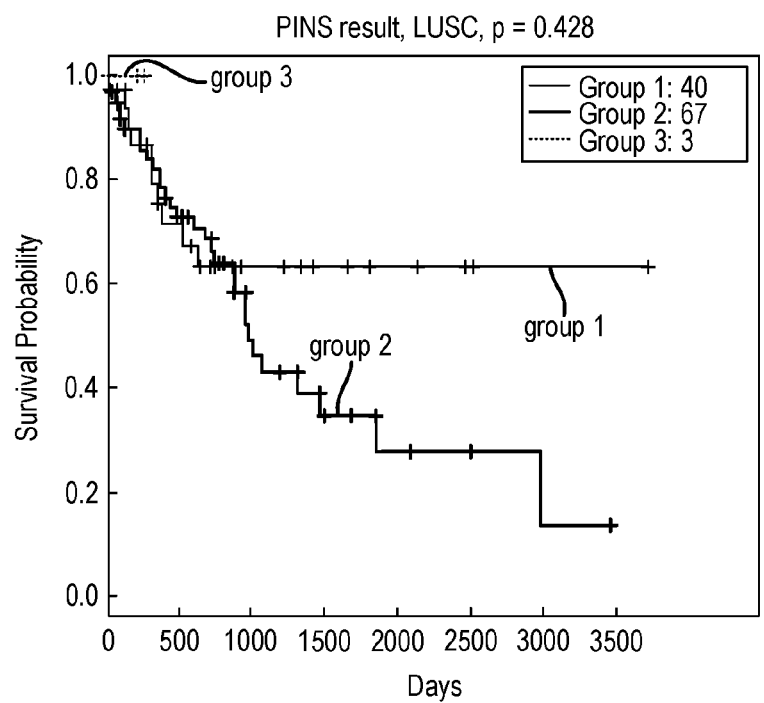

FIG. 20 displays the Kaplan-Meier analysis for LUSC. SNF finds 3 groups with no significantly different survival (p=0.428). In contrast, PINS discovers 5 different groups with different survival profiles (p=$9.7 \times 10^{-3}$). None of the groups is split further in phase 2.

Figure 21A:
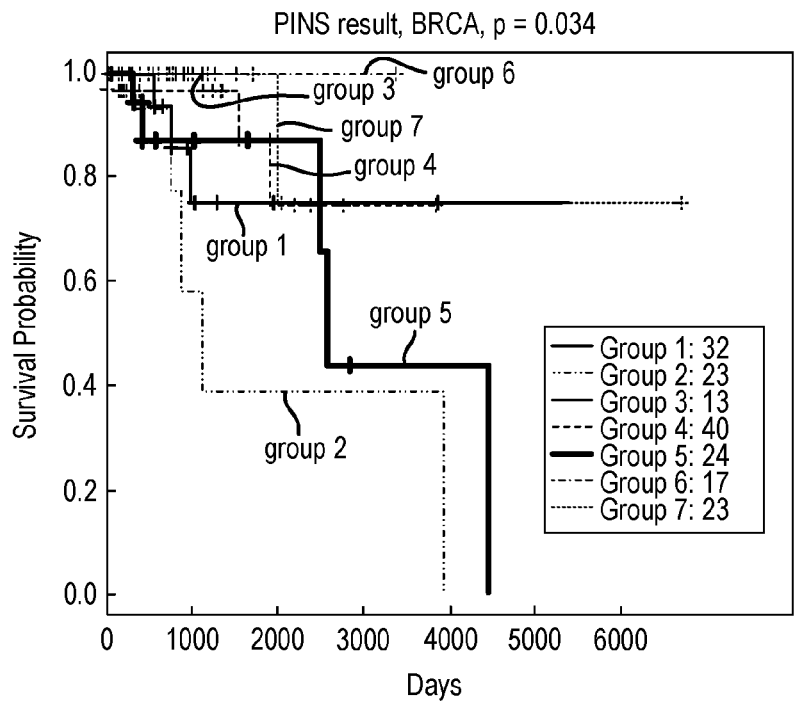
FIG. 21A-21B (collectively referred to as FIG. 21) are Kaplan-Meier survival analysis graphs for breast invasive carcinoma (BRCA), comparing the presently disclosed PINS technique (FIG. 21A) with the SNF technique (FIG. 21B)
Figure 21B:
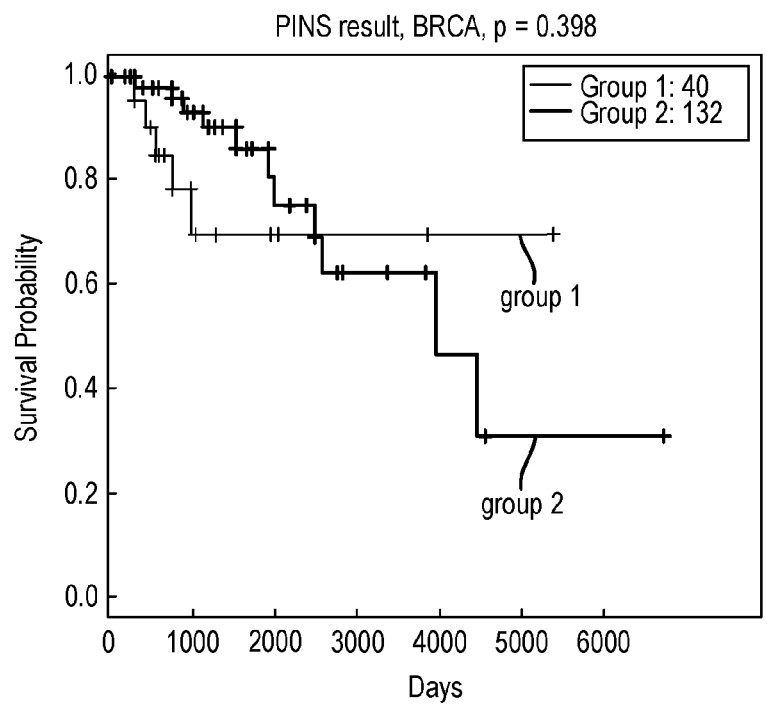

FIG. 21 displays the Kaplan-Meier analysis for BRCA. SNF finds 3 groups with no significantly different survival (p=0.428). In contrast, PINS discovers 5 different groups with different survival profiles (p=0.034).

Figure 22A:
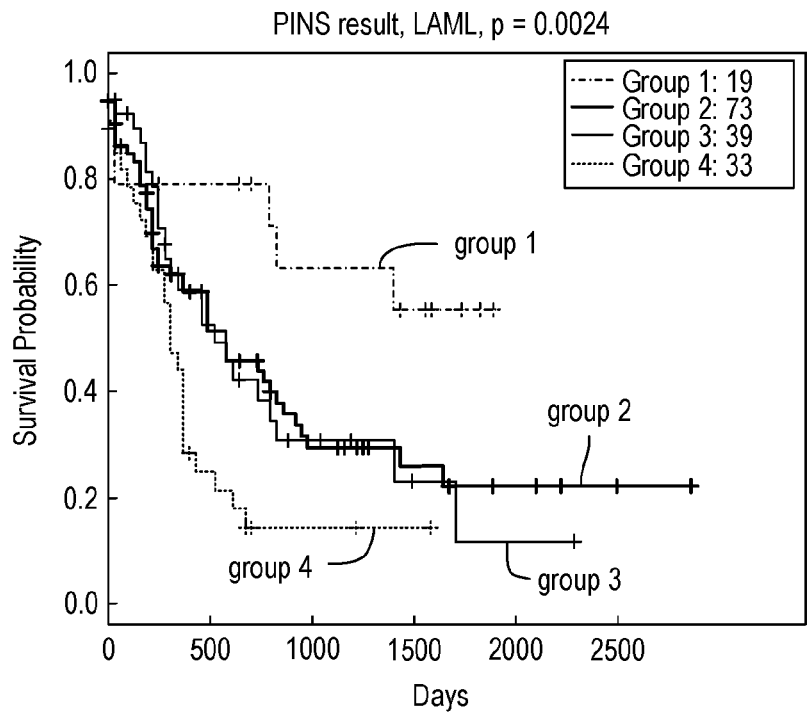
FIG. 22A-22B (collectively referred to as FIG. 22) are Kaplan-Meier survival analysis graphs for acute myeloid leukemia (LAML), comparing the presently disclosed PINS technique (FIG. 22A) with the SNF technique (FIG. 22B)
Figure 22B:
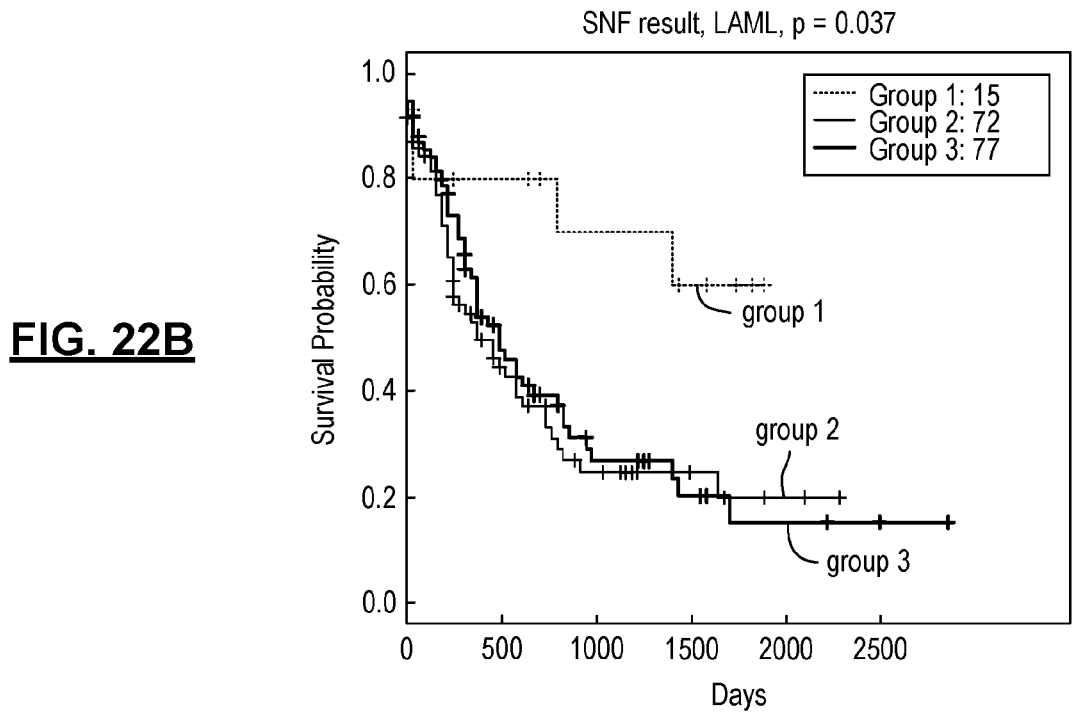

FIG. 22 displays the Kaplan-Meier analysis for LAML. SNF finds 3 groups with significantly different survival (p=0.037). PINS discovers 4 different groups with different survival profiles (p=$2.4 \times 10^{-3}$).

Figure 23A:
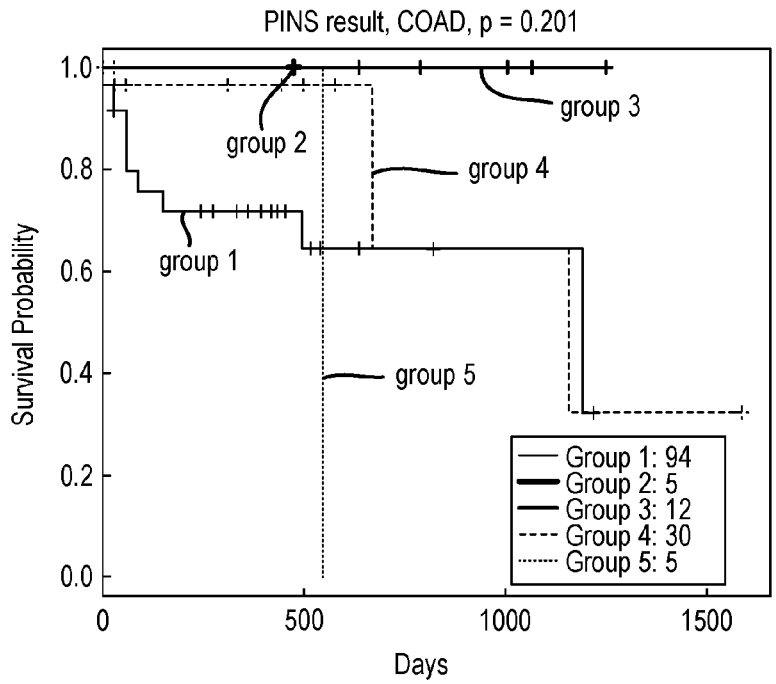
FIG. 23A-23B (collectively referred to as FIG. 23) are Kaplan-Meier survival analysis graphs for colon adenocarcinoma (COAD), comparing the presently disclosed PINS technique (FIG. 23A) with the SNF technique (FIG. 23B)
Figure 23B:
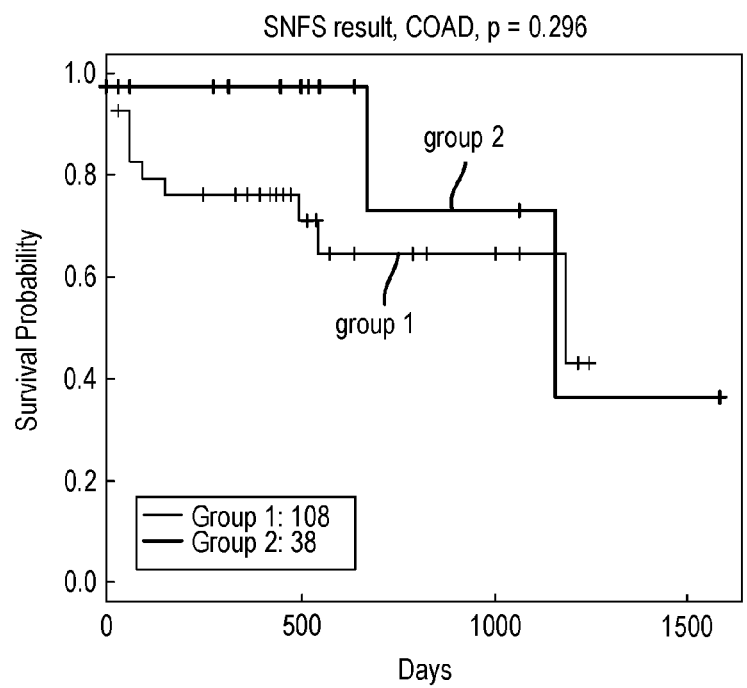

FIG. 23 displays the Kaplan-Meier analysis for COAD. SNF discovers 2 groups while PINS discovers 4 groups.

TABLE IV

Subtypes Discovered by PINS and SNF for 6 TCGA Cancer Datasets Using Individual Data Types as well as Integrated Data

| TCGA Dataset | | | PINS | | SNF | |
|---|---|---|---|---|---|---|
| Name | #Sample | Data Type | #Cluster | Cox p-value | #Cluster | Cox p-value |
| KIRC | 124 | mRNA | 2 | 0.176 | 2 | 0.219 |
| | | Methylation | 3 | 0.111 | 3 | 0.577 |
| | | miRNA | 2 | 0.138 | 2 | 0.138 |
| | | Data integration | 4 | $1.3 \times 10^{-4}$ | 2 | 0.138 |
| GBM | 273 | mRNA | 2 | 0.408 | 2 | 0.992 |
| | | Methylation | 2 | $10^{-4}$ | 2 | 0.017 |
| | | miRNA | 4 | 0.086 | 2 | 0.401 |
| | | Data integration | 3 | $8.7 \times 10^{-5}$ | 4 | 0.062 |
| LUSC | 110 | mRNA | 3 | 0.125 | 3 | 0.095 |
| | | Methylation | 8 | 0.019 | 2 | 0.376 |
| | | miRNA | 2 | 0.117 | 2 | 0.001 |
| | | Data integration | 3 | $9.7 \times 10^{-3}$ | 3 | 0.428 |
| BRCA | 172 | mRNA | 2 | 0.902 | 2 | 0.969 |
| | | Methylation | 4 | 0.048 | 5 | 0.878 |
| | | miRNA | 3 | 0.218 | 2 | 0.105 |
| | | Integration | 7 | $3.4 \times 10^{-2}$ | 2 | 0.398 |
| LAML | 164 | mRNA | 5 | 0.003 | 2 | 0.327 |
| | | Methylation | 6 | 0.239 | 2 | 0.993 |
| | | miRNA | 2 | 0.072 | 3 | 0.183 |
| | | Data integration | 4 | $2.4 \times 10^{-3}$ | 2 | $3.7 \times 10^{-2}$ |
| COAD | 146 | mRNA | 2 | 0.113 | 2 | 0.148 |
| | | Methylation | 2 | 0.741 | 2 | 0.389 |
| | | miRNA | 4 | 0.452 | 3 | 0.131 |
| | | Data integration | 5 | 0.201 | 2 | 0.296 |

For glioblastoma multiform (GBM) dataset, SNF cannot find significant different groups using mRNA or miRNA but it finds 2 significant different groups using methylation data (p=0.017). Similarly, PINS cannot find significant groups using mRNA or miRNA but finds 2 significantly different groups using methylation data (p=$10^{-4}$). SNF cannot find significant different groups after data integration despite having significantly different groups using methylation data. In contrast, data integration by PINS finds 3 groups with even more significant p-value than those of individual data types (p=$8.7 \times 10^{-5}$).

Figure 19A:
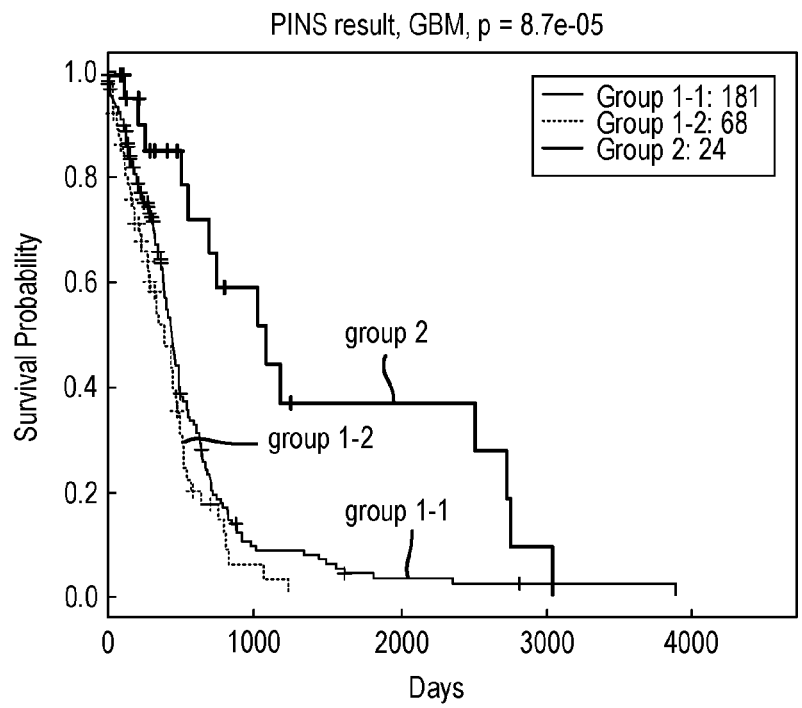
FIG. 19A-19B (collectively referred to as FIG. 19) are Kaplan-Meier survival analysis graphs for glioblastoma multiform (GMB), comparing the presently disclosed PINS technique (FIG. 19A) with the SNF technique (FIG. 19B)
Figure 19B:
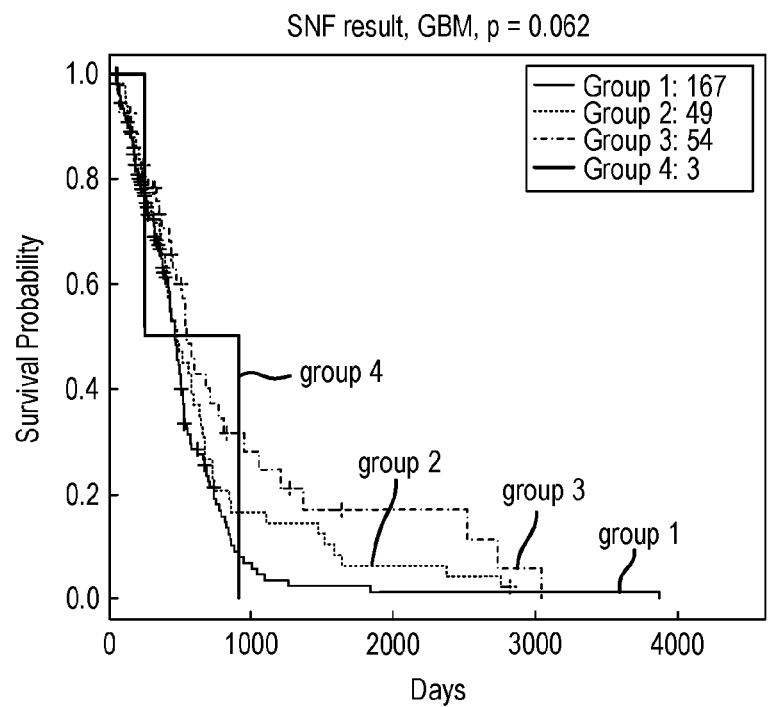

FIG. 19 displays the Kaplan-Meier analysis for GBM. SNF finds 4 groups with no significantly different survival (p=0.062). In contrast, PINS discovers 3 different groups with very different survival profiles (p=$8.7 \times 10^{-5}$). In phase 1, PINS finds 2 groups of patients: group 1 consists of 249 patients, and group 2 consists of 24 patients. In phase 2, group 1 is further divided into group 1-1 (181 patients) and Neither algorithm can find subgroups with significant different survival for any one of the single data types nor with the integrated data.

C. First Case Study—Glioblastoma Multiform (GBM)

Figure 24A:
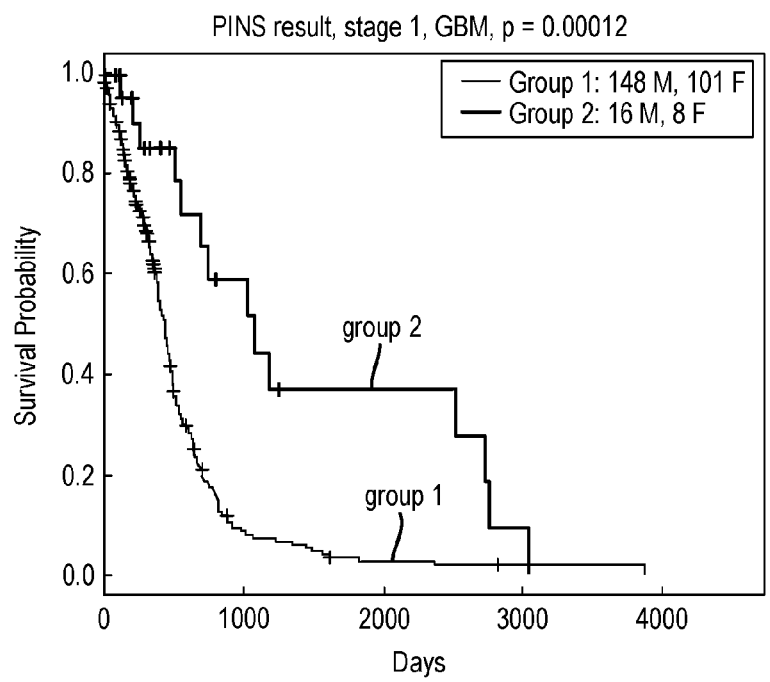
FIG. 24A-24B (collectively referred to as FIG. 24) are Kaplan-Meier survival analysis graphs for glioblastoma multiform (GMB) phase 1 (FIG. 24A) and phase 2 (FIG. 24B), applying the presently disclosed PINS technique.
Figure 24B:
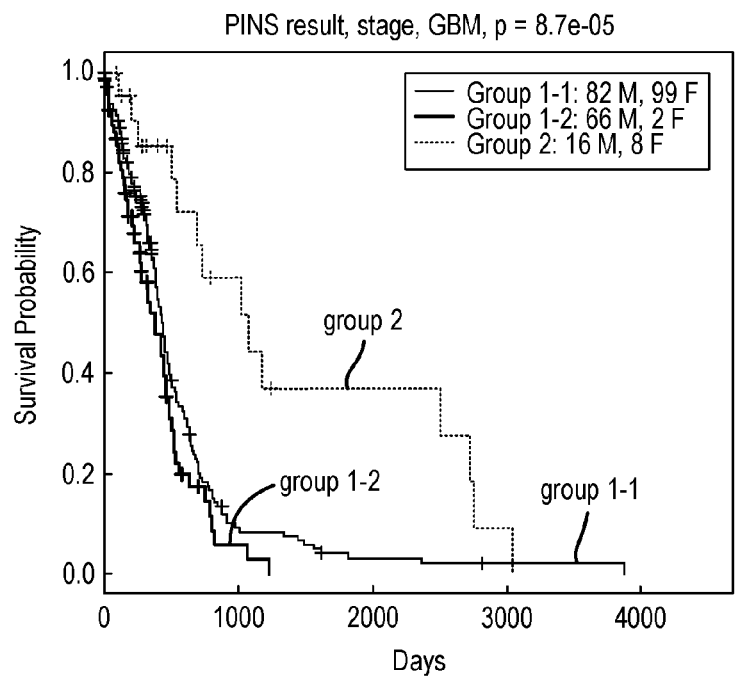
Figure 25:
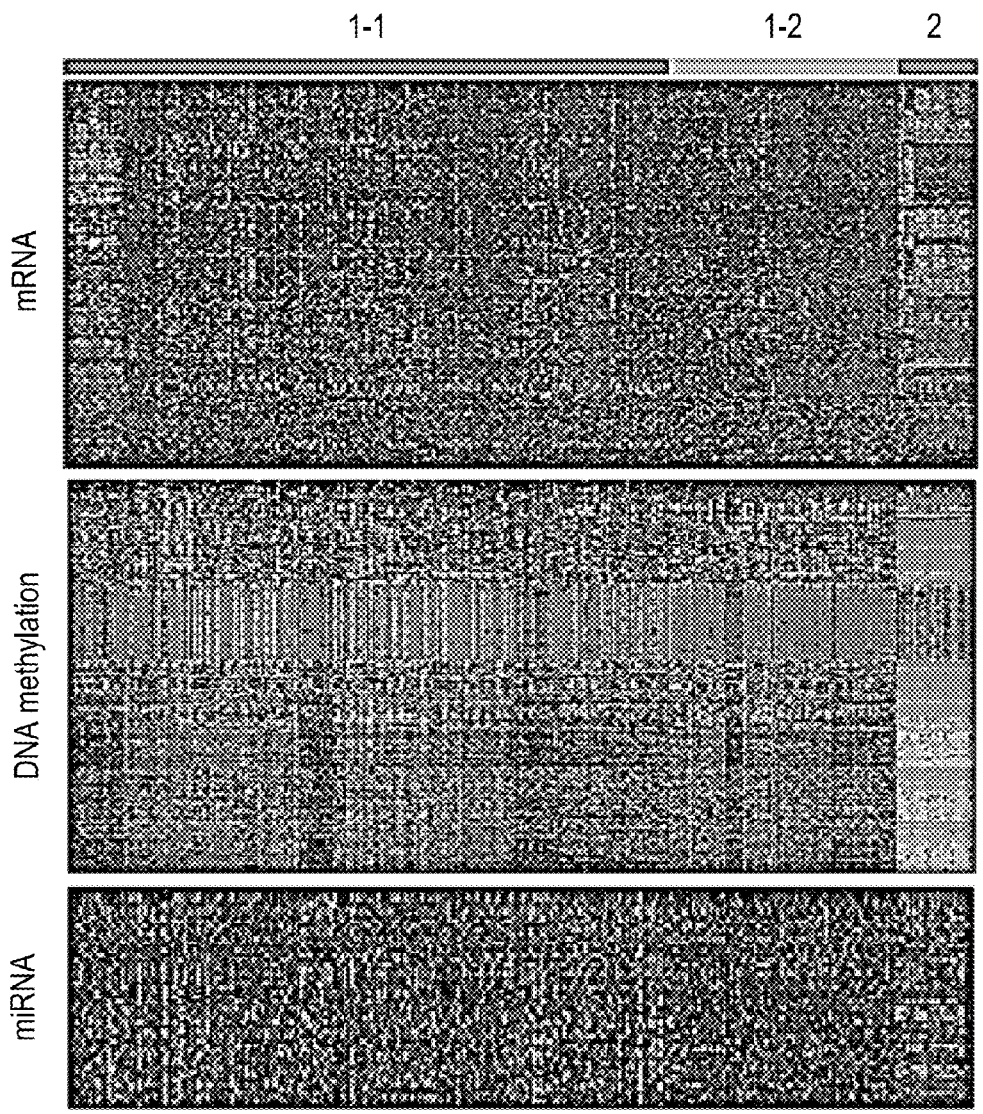
FIG. 25 is a heatmap of features differentials among glioblastoma multiform (GMB) subtypes, comparing three data types: mRNA, DNA methylation, and miRNA.
Figure 26:
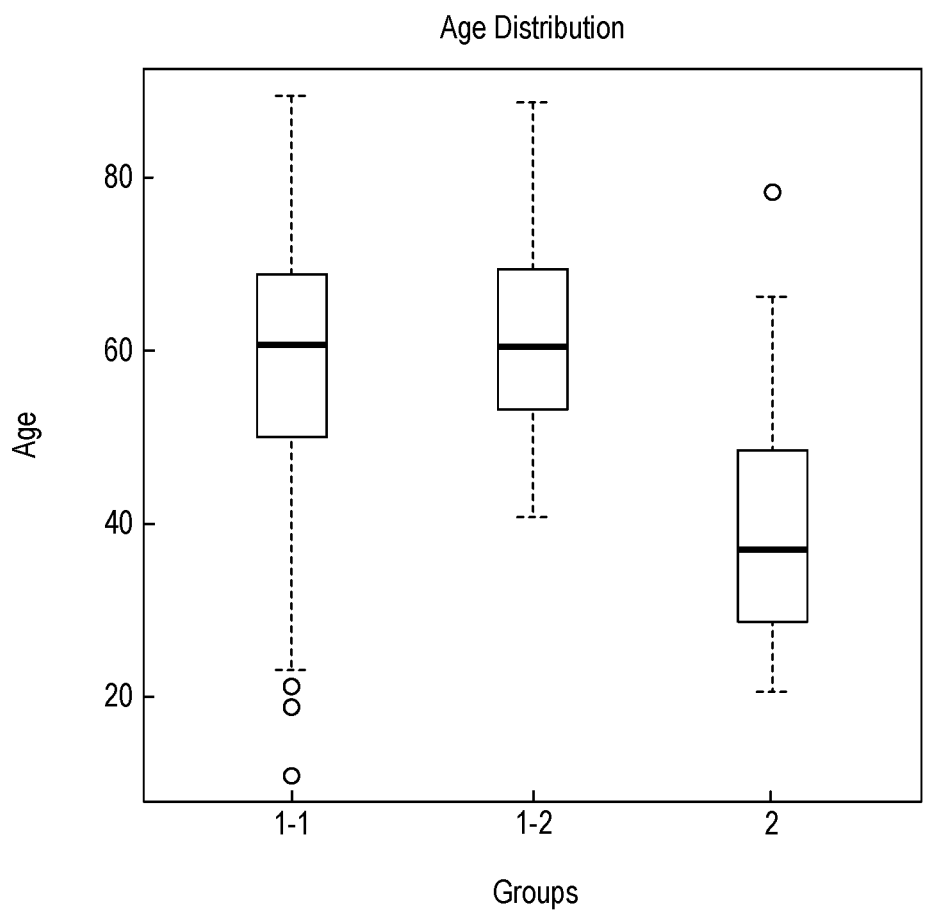
FIG. 26 is a chart showing age distribution of the discovered subtypes for glioblastoma multiform (GMB)

We use PINS to subtype multi-omics data for 273 patients with glioblastoma multiform (GBM). The data types are mRNA expression (HT HG-U133A), DNA methylation (HumanMethylation27), and miRNA expression (Illumina HiSeq miRNASeq) as shown in Table III. FIG. 24 shows the discovered subtypes. The upper panel shows the 2 subtypes discovered in stage I and the lower panel shows the 3 subtypes discovered in stage II. The horizontal axes represent the time pass after entry into the study while the vertical axes represent estimated survival percentage.

We downloaded the somatic mutation data for GBM from TCGA website. Among 273 samples, only 125 samples have somatic mutation information. Here we take into consideration a mutation (gene) if it is positive in at least 5 samples. We count the number of mutations in each subtype for each gene. We then calculate the enrichment p-value using Fisher exact test and then adjust for multiple comparison using FDR correction. Table V displays the 3 mutations that are enriched after FDR correction (at cutoff 0.01). We can see that IDH1 and ATRX mutations only appear in subtype 2 and not in other subtypes.

Here we integrate three data types (mRNA, DNA methylation, miRNA) of 131 patients (Table III). FIG. 24 displays the results of PINS.

We downloaded the somatic mutation data for the samples in GBM dataset from TCGA, and apply the same approach explained above for the samples in GBM. The genes which are mutationally enriched in each of the subtypes are shown in Table VI. Again, we observe that the subtypes found for GBM data set are significantly over-represented by samples that have at least one mutation in the genes that are mutated frequently in the samples in the different survival groups.

TABLE V

Somatic Mutation Information for Glioblastoma Multiform (GMB)

|  | Group 1-1 78 (181) | Group 1-2 38 (68) | Group 2 9 (24) | pFisher.fdr |
|---|---|---|---|---|
| IDH1 | 0 | 0 | 9 | $7 \times 10^{-12}$ |
| ATRX | 0 | 0 | 8 | $4 \times 10^{-10}$ |
| TP53 | 24 | 8 | 9 | 0.001 |

D. Second Case Study—Kidney Renal Clear Cell Carcinoma (KIRC):

Multiple integrative approaches have been applied to identify the subtypes of kidney renal clear cell carcinoma (KIRC). Depending on the data types, these analyses can lead to different conclusions.

Here we integrate three data types (mRNA, DNA methylation, miRNA) of 131 patients (Table III). FIG. 23 displays the results of PINS.

We downloaded the somatic mutation data for the samples in KIRC dataset from TCGA. Using the mutation information for the samples, which have been subtyped using the approach described above, we identify genes that are mutated frequently in the samples in the different survival groups. The significance of mutations for each gene in each subtype is assessed by the number of samples with at least one mutation in that gene in that subtype and in the whole analysis using Fisher's exact test. We apply this approach to the KIRC datasets downloaded from TCGA. The genes which are mutationally enriched in each of the subtypes are shown in Table V. We observe that the subtypes found in the analysis are significantly over-represented by samples that have at least one mutation in these genes.

Figure 27A:
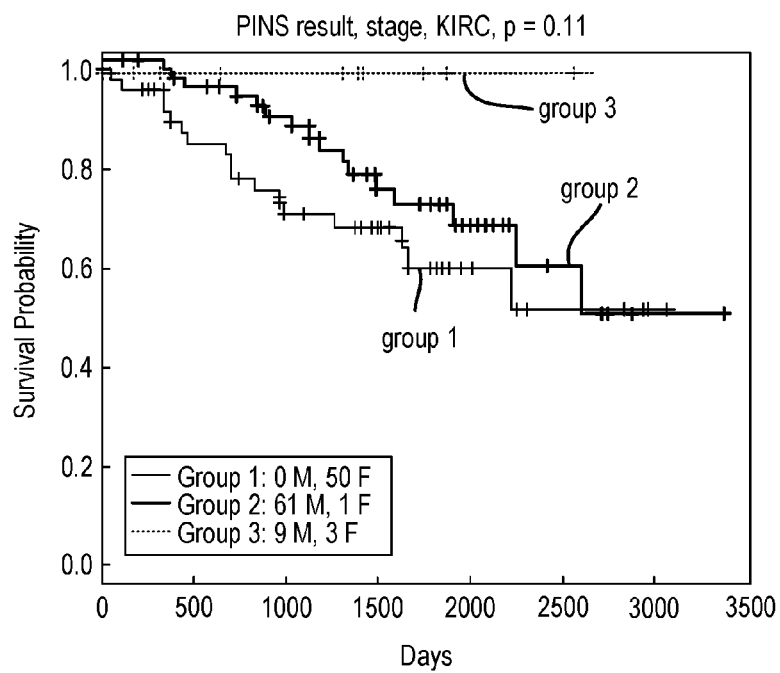
FIG. 27A-27B (collectively referred to as FIG. 27) are Kaplan-Meier survival analysis graphs for kidney renal clear cell carcinoma (KIRC) phase 1 (FIG. 27A) and phase 2 (FIG. 27B), applying the presently disclosed PINS technique.
Figure 27B:
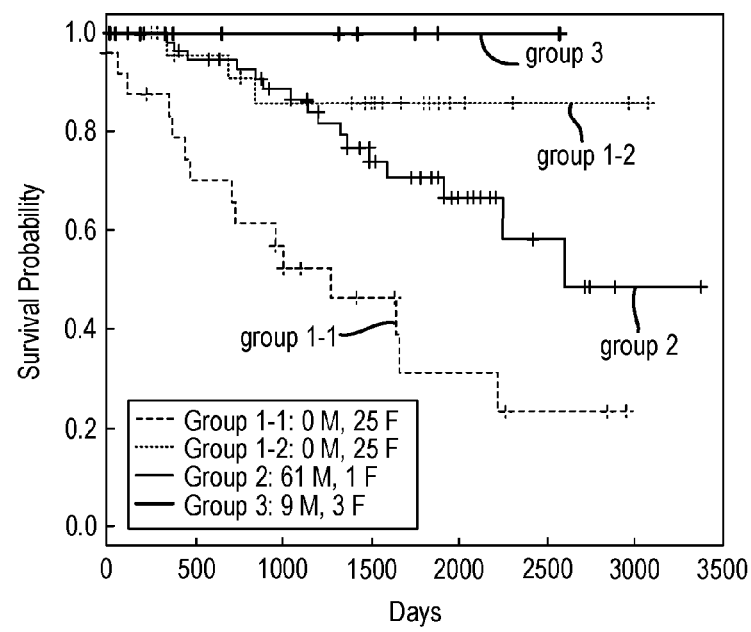

We use PINS to integrate multi-omics data for 124 patients with kidney renal clear cell carcinoma (KIRC). The data types are mRNA expression (Illumina HiSeq), DNA methylation (HumanMethylation27), and miRNA expression (Illumina GASeq) as shown in Table III. FIG. 27 shows the discovered subtypes. The upper panel shows the subtypes discovered in stage I and the lower panel shows the subtypes discovered in stage II. The horizontal axes represent the time pass after entry into the study while the vertical axes represent estimated survival percentage. In stage I, PINS discovers 3 subtypes: subtype 1 (black) consisting of 50 females, subtype 2 (red) consisting of 61 males and 1 female, and subtype 3 (green) consisting of 9 males and 3 females. The survival rate between the large male and female groups is comparable.

In stage II, subtype 1 is equally divided into 2 subgroups with very different survival rates. Subtype 3 is not considered in stage II because it consists two few samples. Subtype 2 is not divided in stage II because the 3 data types give very contradictory signals for this group. In summary, PINS discovers 4 different subtypes with very different survival profiles ($p=1.3\times10^{-4}$). The significant different subtypes can be obtained only when the 3 data types are integrated and analyzed together. Although the subtype discovery was done on molecular data alone, with no use of clinical information, the 4 groups identified have significantly different clinical profiles: group 1-1 contains short-term survival women, group 1-2 contains longer-term survival women, group 2 contains only men, and group 3 contains survivors (all patients were still alive at the end of the study).

Figure 28:
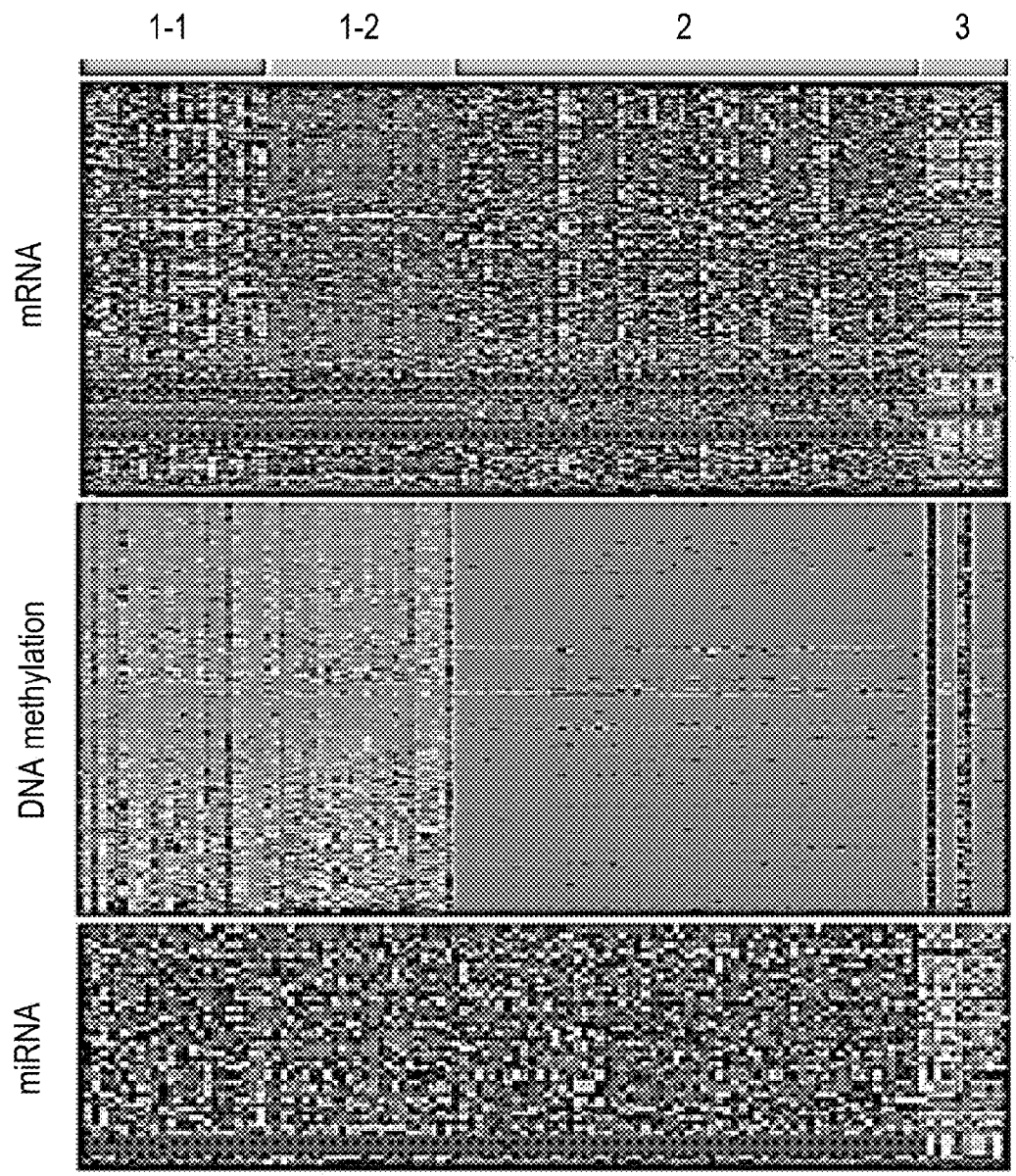
FIG. 28 is a heatmap of features differentials among kidney renal clear cell carcinoma (KIRC) subtypes, comparing three data types: mRNA, DNA methylation, and miRNA.
Figure 29:
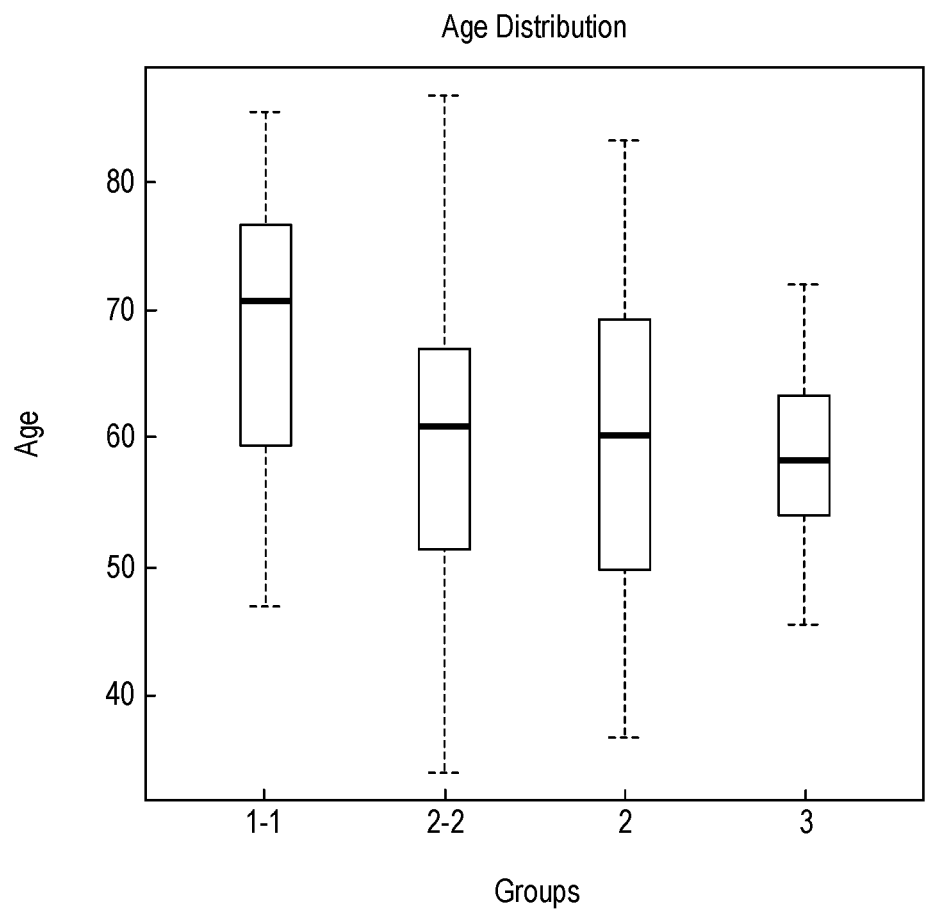
FIG. 29 is a chart showing age distribution of the discovered subtypes for kidney renal clear cell carcinoma (KIRC)

FIG. 28 displays the heatmap of features differential among kidney recall clear cell carcinoma (KIRC) subtypes. The panels display the expression of the three data types: top panel—mRNA expression, middle panel—DNA methylation, and bottom panel—miRNA expression. The color band on the top shows the 4 subtypes (1-1, 1-2, 2, and 3). The features are selected as follows: we cluster the data using each feature independently with k=4 (number of subtypes using PINS). Rand index (RI) is then calculated between the resulted clustering and PINS found subtypes. We then order all the RI values and show those that are ranked highest for each data type. We show top 100 features for mRNA (out of 17; 974), 100 features for DNA methylation (out of 23; 165), and 30 features for miRNA (out of 590). mRNA and miRNA provide a clear signal between subtype 3 (highest survival) and the rest. The expression values for those features are either much lower (red) or much higher (green) than the rest. DNA methylation gives a clear distinction between males and females and thus helps to separate subtype 2 from subtype 1 (the union of 1-1 and 1-2). mRNA helps to separate subtype 1-1 from 1-2.

1) KIRC Clinical Parameters:

Enrichment for different clinical characteristics was analyzed for each of the four survival clusters. Table VI shows the numbers and percentages of each of the 124 patients into each of the survival clusters and clinical categories. FDR adjusted p-values were calculated for phenotype enrichment in each of the clusters versus the others, and good versus poor survivors. Using an FDR cutoff of 5%, we find that group 3 (all survivors) are typically between ages 50 and 60, with normal calcium levels, while the medium survivors are typically younger, and poor survivors tend to be over 70. Group 2 (medium survival male) tends to have low calcium and fall into grade III. Poor survivors (female group 1-1) have elevated platelets and elevated calcium, and fall into grade G4, stages III and IV. Group 1-2 (medium-good survival females) are predominantly stage I with normal hemoglobin. The two pure female clusters (1-1 and 1-2) include the majority of patients with elevated platelets. The low survivors (1-1 and 2) compared to the high survivors (groups 3 and 1-2) have low hemoglobin and high grade.

TABLE VI

Distribution of Patients in Four Survival Clusters in Each Phenotypic Category

|  |  | (A) Number in each group | | | | (B) % phenotype in each group | | | | (C) % group in each phenotype | | | |
|---|---|---|---|---|---|---|---|---|---|---|---|---|---|
| Survival Group | | 3 | 1-2 | 2 | 1-1 | 3 | 1-2 | 2 | 1-1 | 3 | 1-2 | 2 | 1-1 |
| Gender | Female | 3 | 25 | 1 | 25 | 6 | 46 | 2 | 46 | 25 | 100 | 2 | 100 |
|  | Male | 9 | 0 | 61 | 0 | 13 | 0 | 87 | 0 | 75 | 0 | 98 | 0 |
| Tumor Grade | G1 | 0 | 1 | 1 | 1 | 0 | 33 | 33 | 33 | 0 | 4 | 2 | 4 |
|  | G2 | 6 | 15 | 28 | 12 | 10 | 25 | 46 | 20 | 75 | 60 | 45 | 48 |
|  | G3 | 2 | 9 | 28 | 5 | 5 | 20 | 64 | 11 | 25 | 36 | 45 | 20 |
|  | G4 | 0 | 0 | 5 | 7 | 0 | 0 | 42 | 58 | 0 | 0 | 8 | 28 |
| AJCC pathologic tumor stage | I | 7 | 17 | 31 | 5 | 12 | 28 | 52 | 8 | 58 | 68 | 50 | 20 |
|  | II | 4 | 3 | 9 | 2 | 22 | 17 | 50 | 11 | 33 | 12 | 15 | 8 |
|  | III | 1 | 4 | 18 | 12 | 3 | 11 | 51 | 34 | 8 | 16 | 29 | 48 |
|  | IV | 0 | 1 | 4 | 6 | 0 | 9 | 36 | 55 | 0 | 4 | 6 | 24 |
| Serum Calcium Level | Low | 1 | 9 | 27 | 9 | 2 | 20 | 59 | 20 | 14 | 60 | 68 | 43 |
|  | Normal | 6 | 6 | 12 | 9 | 18 | 18 | 36 | 27 | 86 | 40 | 30 | 43 |
|  | Elevated | 0 | 0 | 1 | 3 | 0 | 0 | 25 | 75 | 0 | 0 | 3 | 14 |
| Hemoglobin Level | Low | 3 | 8 | 34 | 18 | 5 | 13 | 54 | 29 | 38 | 38 | 68 | 75 |
|  | Normal | 5 | 13 | 16 | 6 | 13 | 33 | 40 | 15 | 63 | 62 | 32 | 25 |
| Platelet Count | Normal | 7 | 17 | 42 | 16 | 9 | 21 | 51 | 20 | 88 | 81 | 88 | 67 |
|  | Elevated | 1 | 3 | 2 | 8 | 7 | 21 | 14 | 57 | 13 | 14 | 4 | 33 |
| Age | <50 | 1 | 6 | 16 | 1 | 4 | 25 | 67 | 4 | 8 | 24 | 26 | 4 |
|  | 50-60 | 7 | 4 | 15 | 6 | 22 | 13 | 47 | 19 | 58 | 16 | 24 | 24 |
|  | 60-70 | 3 | 10 | 17 | 5 | 9 | 29 | 49 | 14 | 25 | 40 | 27 | 20 |
|  | >70 | 1 | 5 | 14 | 13 | 3 | 15 | 42 | 39 | 8 | 20 | 23 | 52 |

TABLE VII

Distribution of Patients in Two Clusters and AJCC Pathologic Tumor Stage

| AJCC Pathologic Tumor Stage | female.1 (poor survival) | female.2 (good survival) | Total |
|---|---|---|---|
| Stage I | 5 (23%) | 17 (77%) | 22 |
| Stage II | 2 (40%) | 3 (60%) | 5 |
| Stage III | 12 (75%) | 4 (25%) | 16 |
| Stage IV | 6 (86%) | 1 (14%) | 7 |
| Total | 25 | 25 | |

2) KIRC Female Subgroups—Clinical Parameters:

The low survival group includes 86% of the Stage IV cases, while the high survival group includes 77% of the Stage I cases, representing an FDR corrected p-values of less than 0.5%. Other parameters that were significant at FDR<5% included tumor grade (poor survivors had a higher incidence of 'G4' tumors, FDR 2%), tumor status (poor survivors were 'with tumor', FDR 2%), hemoglobin level (poor survivors had low levels, FDR 2%), metastasis (2%).

3) KIRC Female Subgroups—Differential Gene Expression:

Based on absolute log-fold-change of 1.5 and maximum FDR adjusted p-value of 1%, there were 165 differentially expressed genes between long- and short-term survivors. Eighty percent (132) of these were down-regulated in the poor survivors. Functional analysis of all 165 genes using iPathwayGuide points to damaged proximal tubules in the nephrons of women with poor outcome. Most common renal cell carcinomas occur in the proximal tubules. Two KEGG pathways had FDRs on the order of $10^{-4}$: 'Metabolic Pathways', and 'Mineral Absorption'. Several differentially expressed solute carriers on the Mineral Absorption Pathway are located in 'brush border membrane', shown in FIG. 36. In kidney, brush border membranes are found in the proximal tubules, which carry filtrate away from the glomerulus in the nephron, and support the secretion and absorption of charged molecules into and out of the filtrate. Gene Ontology (GO) terms analyzed at 1% FDR significance support a hypothesis of damage to proximal tubule membranes. Thirteen significant Cellular Component terms were related to plasma membrane, in particular 'brush border membrane'. All 23 Biological Process terms concern known proximal tubule functions: metabolic/catabolic processes, immune response, transmembrane and ionic transport. All but one ('glucosidase activity') of 15 Molecular Function terms involve active ionic transport across a plasma membrane. These terms included many differentially expressed solute carriers. The alpha-glucosidase precursor has been localized to the proximal tubule brush border, where it is secreted into the urine.

TABLE VIII

Gene Ontology and Disease Summary

| Database | 33 up | 132 down |
|---|---|---|
| GO Biological Process | Metallothionein and metallopeptidase activity | Metabolic processes, transport |
| GO Molecular Function | Enzyme Inhibition | Transporter activity, binding |
| GO Cellular Component | Extracellular Region | Brush Border Membrane, Plasma Membrane |
| Webgestalt Disease | Cancer and Respiratory Tract Diseases | Kidney Disease |

4) KIRC Female Subgroups—MiRNAs:

iPathway Guide also outputs a ranked list of miRNAs that are up-regulated between short and long survival women. We select the top 10 miRNA and performs the t-test using miRNA expression. Two microRNAs that were significantly up-regulated (after FDR correction) in the low survival group were among the 10 miRNAs identified by iPathwayGuide with significant enrichment of down-regulated target genes: hsa-mir-497 and hsa-mir-27a dysregulation. These 2 miRNAs have been observed in multiple cancers and may be up or down regulated depending on the context (mircancer.ecu.edu).

Hsa-mir-497 is a tumor suppressor reported to be involved in antiproliferation (cell cycle—G1 arrest, p53 correlation), increased apoptosis (through WEE1), suppression of angiogenesis (through VEGFA), suppression of migration and invasion (through SMURF1), and modulation of multidrug resistance (through BCL2). Hsa-mir-497 dysregulation has been found in carcinomas (prostate, bladder, colon, pancreas, breast, lung, gastric, liver, cervical, peritoneal, . . . ), and is thought to participate in the following biological processes/pathways: cadherin, WNT, T-cell activation, cell-cycle progression, apoptosis, PI3K/AKT, and MAPK/ERK.

Hsa-mir-27a is considered to be an 'onco-miR' with potential SNP inactivation. It is associated with numerous cancers: breast (familial), cervical (HeLa), glioma, AML, ALL, renal, colorectal, prostate, gastric, ovarian, pancreatic, lung, . . . and carcinomas: oral squamous cell, hepatocellular, esophageal squamous cell, gastric adenocarcinoma, . . . . It has been implicated in promoting cellular proliferation, migration and invasion and inhibiting apoptosis (through MCPH1, FOX01 and SPRY2), control of endothelial cell repulsion and angiogenesis (through SEMA6A and VEGF), promoting metastasis by inducing epithelial to mesenchymal transition, enhanced expression of proinflammatory cytokines, and impairment of adipocyte differentiation and mitochondrial function. It is thought to participate in the following biological processes and pathways: cell adhesion and cell-cell interactions, VEGFmediated signaling, MAPK/ERK signaling, EGFR signaling, cell cycle, NF-kb signaling, proinflammatory cytokines, and basal transcription of the p53-273-H/mir-27a/EGFR pathway.

IV. EXEMPLARY EMBODIMENT

Figure 32:
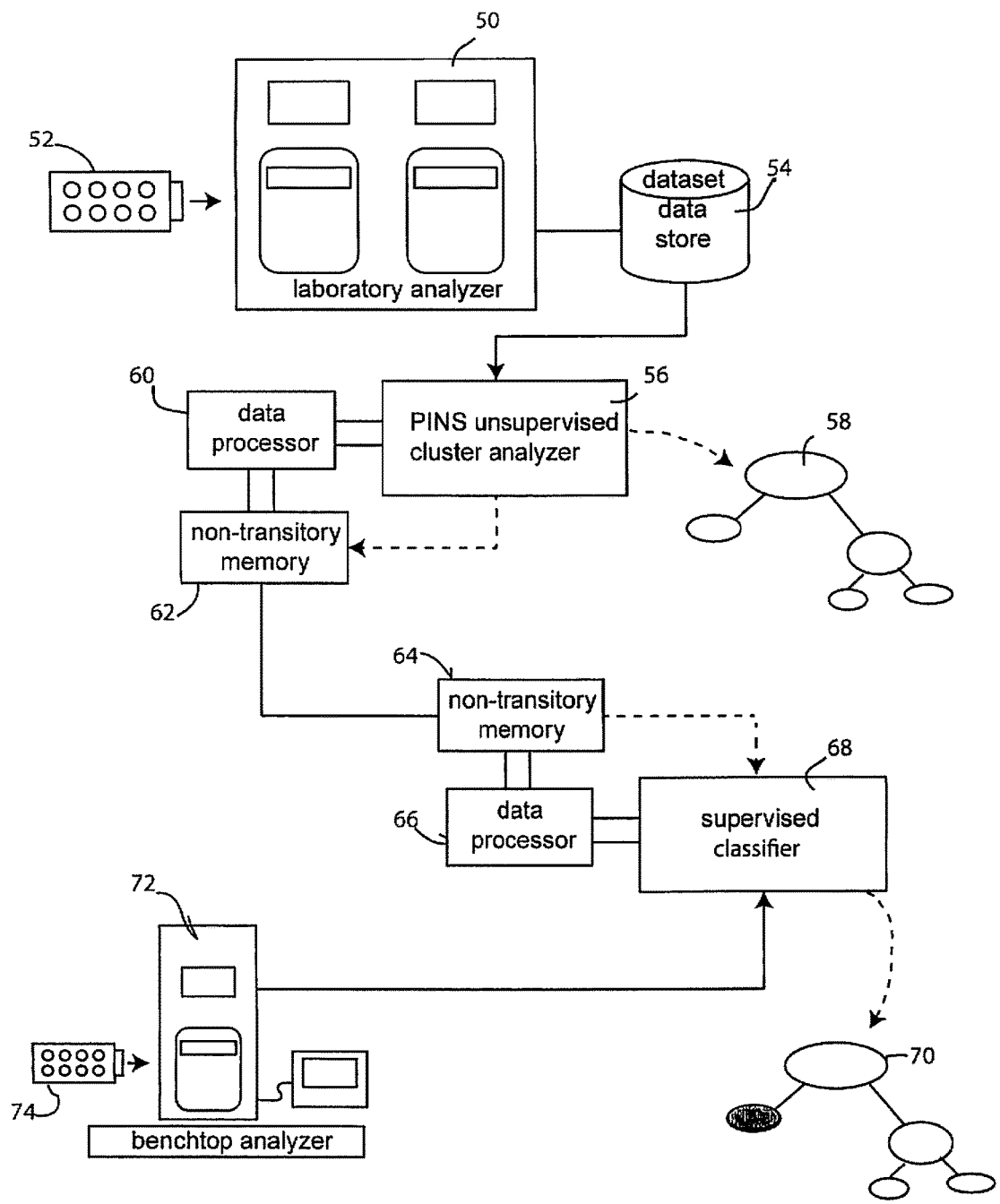
FIG. 32 is a computer system diagram illustrating one combined hardware and software embodiment of implementing the disclosed technique.

Referring now to FIG. 32, an exemplary implementation of a medical testing system utilizing the disclosed concepts will now be described. As illustrated a laboratory genetic analyzer 50 is supplied with samples 52 from a plurality of human subjects and the results are stored in data store 54 as the base dataset. Next the PINS unsupervised cluster analysis process 56, as described herein, is performed using data processor 60 and its associated non-transitory memory 62 (e.g. RAM and/or non-transitory storage) to find the optimal clusters 58 from the base dataset in data store 54. The optimal clusters so discovered are stored as cluster data in memory 62.

Thereafter, a DNA sample from an individual patient is obtained at 74 and analyzed with a benchtop analyzer 72. Essentially, the benchtop analyzer 72 is obtaining sample data from the individual patient that is identical to or of a similar character to the data collected from the plurality of human subjects as processed by the laboratory genetic analyzer 50. The output from the benchtop analyzer 72 is supplied to data processor 66. Data processor has an associated non-transitory memory 64 into which has been loaded the cluster data from memory 62, representing the previously discovered unsupervised optimal clusters. Processor 66 uses the data from the individual patient to perform a supervised classification analysis which identifies which cluster most closely represents the data from the individual patient, as shown at 70.

With the individual patient now assigned to the optimal cluster that most closely corresponds to that patient's actual genetically analyzed data, the treating physician selects the treatment regimen that is best suited to that patient's needs. As noted above, without this knowledge the conventional treatment protocol might well dictate that the patient be given the "most popular" treatment, unaware that in this case that treatment will not work and thus valuable life-giving time is being wasted.

V. CONCLUSIONS

In this disclosure, we present a new approach for data integration and disease subtyping. Our contribution is twofolds. First, we proposed a novel method to efficiently cluster high-dimensional data. This approach adds noise to the input to learn the data's behavior. The algorithm then chooses the partitioning that is the most robust against data perturbation. Second, we integrate multi-omics data by combining the similarity matrices of individual data types. Our framework looks for strong connections across all data types to determine the number of clusters for the final partitioning. This makes the partitioning more stable than by looking at the partitioning of each data type alone.

The advantage of the new approach is demonstrated by extensive data analysis. We examine 8 gene expression datasets of different diseases: lung cancer, leukemia, and brain tumors. Rand Index (RI) and Adjusted Rand Index (ARI) are used as metrics to compare the performance of PINS, Consensus Clustering (CC), and Similarity Network Fusion (SNF). For all the 8 datasets, Perturbation Clustering outperforms its competitor and also correctly identifies the number of subtypes for most of the datasets.

To evaluate the new approach's ability to combine multi-omics data, we examine 6 cancers available on The Cancer Genome Atlas (TCGA): glioblastoma multiform (GBM), lung squamous cell carcinoma (LUSC), breast invasive carcinoma (BRCA), acute myeloid leukemia (LAML), kidney renal clear cell carcinoma (KIRC) and colon adenocarcinoma (COAD). Using the Cox log-rank test, we show that our framework has a clear advantage among the competing methods.

APPENDIX

Adjusted Rand Index

We use Rand index (RI) and adjusted Rand Index (ARI) as the metrics to assess the agreement between a clustering and the ground truth (true classes of the elements). Rand Index of 2 partitionings is the number of pairs that agree divided by the total number of pairs. In short, $$RI = \frac{a+b}{\binom{N}{2}}$$

where a is the number of pairs that are clustered together in both partitionings, b is the number of pairs that are separated in both partitionings, and $$\binom{N}{2}$$

is the total possible pairs from N elements

TABLE IX

Contingency Table of Two Partitionings

| Class/Cluster | $G_1$ | $G_2$ | ... | $G_g$ | Total |
|---|---|---|---|---|---|
| $C_1$ | $n_{11}$ | $n_{12}$ | ... | $n_{1g}$ | $n_{1.}$ |
| $C_2$ | $n_{21}$ | $n_{22}$ | ... | $n_{2g}$ | $n_{2.}$ |
| . | . | . |  | . | . |
| . | . | . |  | . | . |
| . | . | . |  | . | . |
| $C_r$ | $n_{r1}$ |  | ... | $n_{rg}$ | $n_{r.}$ |
| Total | $n_{.1}$ | $n_{.2}$ | ... | $n_{.g}$ | $n_{..} = n$ |

The adjusted Rand index (ARI) is the corrected-for-chance version of the Rand index. Let us consider two partitionings $\{C_1, C_2, \ldots, C_r\}$ and $\{G_1, G_2, \ldots, G_r\}$. The agreement between these two partitionings is summarized by the contingency Table IX. The adjusted Rand index (ARI) is the corrected-for-chance version of the Rand index. ARI can be calculated as follows:

$$ARI = \frac{\Sigma_{i,j}\binom{n_{ij}}{2} - \left[\Sigma_i\binom{n_{i.}}{2}\Sigma_j\binom{n_{.j}}{2}\right]/\binom{n}{2}}{\frac{1}{2}\left[\Sigma_i\binom{n_{i.}}{2} + \Sigma_j\binom{n_{.j}}{2}\right] - \left[\Sigma_i\binom{n_{i.}}{2}\Sigma_j\binom{n_{.j}}{2}\right]/\binom{n}{2}}$$

While RI falls into the interval [0,1], ARI can be negative. It can be shown that ARI has an expected value of 0 for two random partitionings.

The invention claimed is:

1. A method of conducting at least one of a drug or treatment trial, comprising:
    acquiring a first quantitative biological dataset from a population of candidates;
    processing the first quantitative biological dataset using a computer-implemented unsupervised cluster analysis process to define a plurality of clusters to partition patient data corresponding to the first quantitative biological dataset;
    storing said plurality of clusters in a data store comprising a non-transitory computer-readable memory;
    acquiring second quantitative biological data from at least one individual candidate and processing the acquired second quantitative biological data using a computer-implemented classifier, the classifier ingesting the plurality of clusters in said data store and using the plurality of clusters to find which of the plurality of clusters represents a closest match to the acquired second quantitative biological data of an individual patient;
    storing a cluster of the plurality of clusters found to represent the closest match as patient classification data in a non-transitory computer-readable memory;
    using the patient classification data in determining whether said at least one individual candidate qualifies as a suitable subject of said at least one of the drug or treatment trial; and
    administering at least one of a drug or treatment regimen to said at least one candidate that has qualified as a suitable subject of said at least one of drug or treatment trial,
    wherein the unsupervised cluster analysis process comprises:
        (a) applying a computer-implemented algorithm to the first quantitative biological dataset to construct a set of first connectivity matrices which are then stored in non-transitory computer-readable memory;
        (b) using a computer-implemented algorithm to construct and store in non-transitory computer-readable memory a perturbed dataset by introducing noise into the first quantitative biological dataset;
        (c) applying a computer-implemented algorithm to the perturbed dataset to construct a set of perturbed connectivity matrices which are then stored in non-transitory computer-readable memory;
        (d) using a computer-implemented algorithm to perform a stability assessment that reads from memory and compares the first connectivity matrices with the perturbed connectivity matrices;
        (e) using a computer-implemented algorithm to select, from among the first set of connectivity matrices, a matrix whose corresponding perturbed matrix is least affected by the introduction of noise; and
        (f) storing the selected matrix in non-transitory computer-readable memory and using a computer-implemented algorithm to construct the plurality of clusters.

* * * * *